(12) United States Patent
Bonutti

(10) Patent No.: US 6,312,448 B1
(45) Date of Patent: Nov. 6, 2001

(54) APPARATUS AND METHOD FOR USE IN POSITIONING AN ANCHOR

(76) Inventor: Peter M. Bonutti, 15167 N. Cardinal Dr., Effingham, IL (US) 62401

( * ) Notice: Subject to any disclaimer, the term of this patent is extended or adjusted under 35 U.S.C. 154(b) by 0 days.

(21) Appl. No.: 09/479,647

(22) Filed: Jan. 7, 2000

Related U.S. Application Data

(62) Division of application No. 09/343,371, filed on Jun. 30, 1999, now Pat. No. 6,033,430, which is a division of application No. 09/022,351, filed on Feb. 11, 1998, now Pat. No. 5,948,002, which is a continuation-in-part of application No. 08/752,005, filed on Nov. 15, 1996, now Pat. No. 5,814,072.

(51) Int. Cl.$^7$ .................................................. A61B 17/00
(52) U.S. Cl. .................................... 606/232; 606/104
(58) Field of Search .................................... 606/232, 104, 606/213, 72

(56) References Cited

U.S. PATENT DOCUMENTS

| | | | |
|---|---|---|---|
| 2,248,054 | 7/1941 | Becker | 606/104 |
| 4,235,238 | 11/1980 | Oglu et al. | 606/104 |
| 4,448,194 | 5/1984 | DiGiovanni et al. | 606/232 |
| 4,741,330 | 5/1988 | Hayhurst | 606/232 |
| 5,002,550 | 3/1991 | Li | 606/232 |
| 5,041,129 | 8/1991 | Hayhurst et al. | 606/232 |
| 5,100,417 | 3/1992 | Cerier et al. | 606/232 |
| 5,141,520 | 8/1992 | Goble et al. | 606/232 |
| 5,180,388 | 1/1993 | DiCarlo | 606/232 |
| 5,258,016 | 11/1993 | DiPoto et al. | 606/232 |
| 5,354,298 | 10/1994 | Lee et al. | 606/232 |
| 5,400,805 | 3/1995 | Warren | 606/232 |
| 5,403,348 | 4/1995 | Bonutti | 606/232 |
| 5,411,523 | 5/1995 | Goble | 606/232 |
| 5,464,426 | 11/1995 | Bonutti | 606/232 |
| 5,478,353 | 12/1995 | Yoon | 606/104 |
| 5,522,844 | 6/1996 | Johnson | 606/232 |
| 5,522,846 | 6/1996 | Bonutti | 606/232 |
| 5,549,630 | 8/1996 | Bonutti | 606/232 |
| 5,584,860 | 12/1996 | Goble et al. | 606/232 |
| 5,626,614 | 5/1997 | Hart | 606/232 |
| 5,662,658 | 9/1997 | Wenstrom, Jr. | 606/232 |
| 5,667,513 | 9/1997 | Torrie et al. | 606/232 |

Primary Examiner—Gary Jackson
(74) Attorney, Agent, or Firm—Tarolli, Sundheim, Covell, Tummino & Szabo L.L.P.

(57) ABSTRACT

An apparatus for use in positioning an anchor includes a tubular outer member and an inner or pusher member. During use of the apparatus, a slot facilitates visualization of the position of the anchor relative to body tissue. An anchor retainer may be provided at one end of the tubular outer member to grip the anchor and hold the anchor in place during assembly. The anchor retainer also holds the anchor during movement of the apparatus from an assembly location to an operating room or other location where the apparatus is to be used. Indicia may be provided on the inner member to indicate the position of the anchor relative to body tissue. The tubular outer member may be utilized to guide a drill during formation of an opening in body tissue and may be subsequently utilized to guide movement of an anchor into the opening in the body tissue.

169 Claims, 14 Drawing Sheets

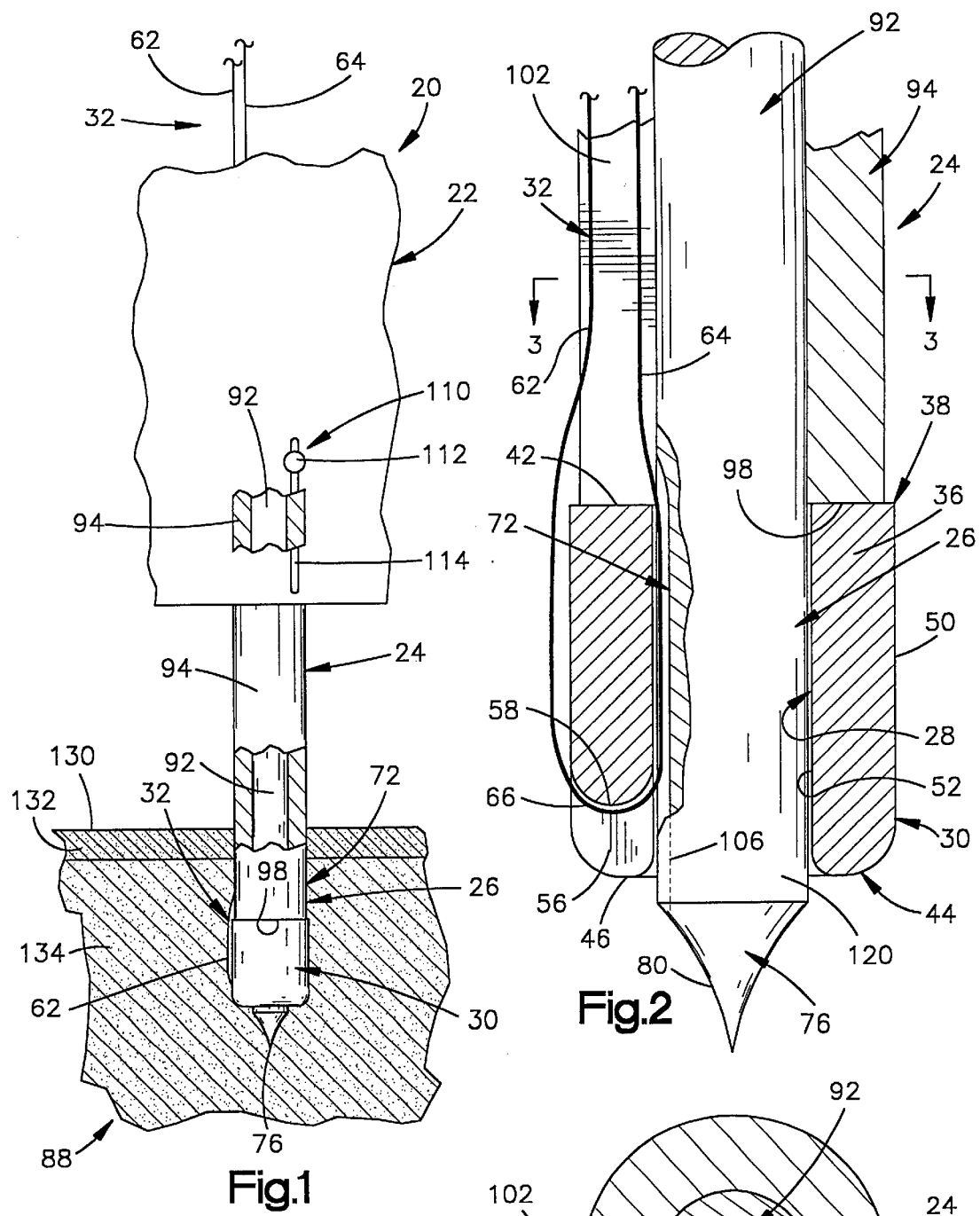
Fig.1
Fig.2
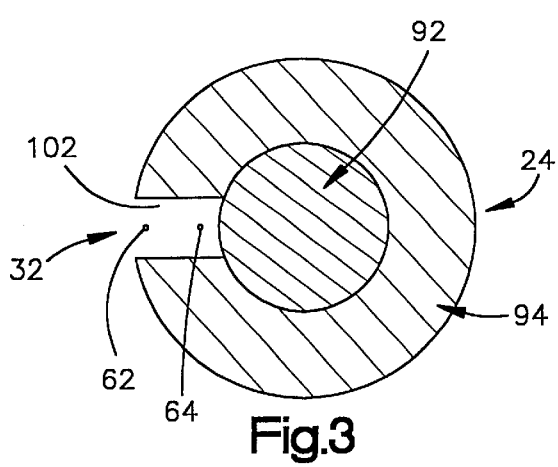
Fig.3

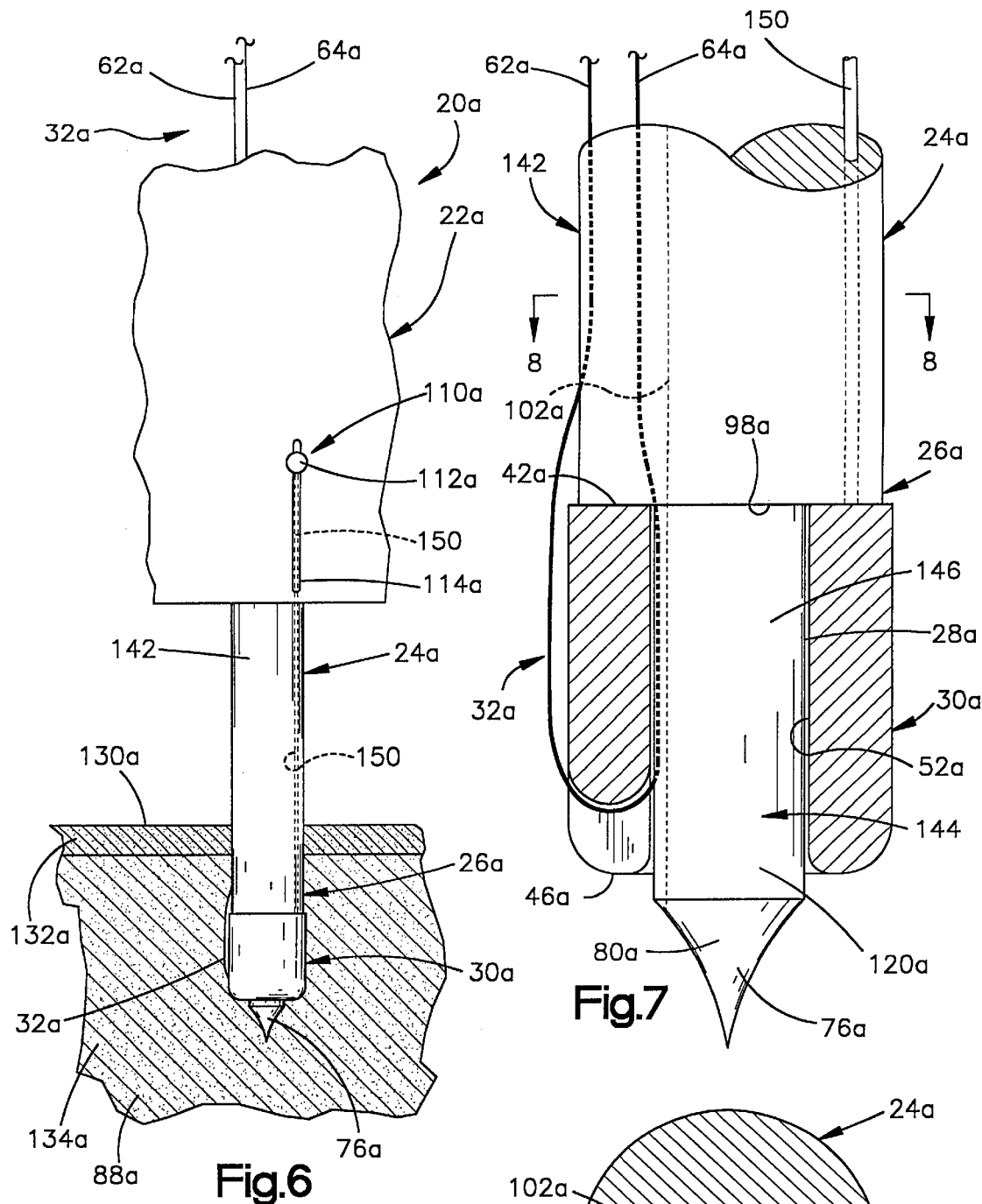

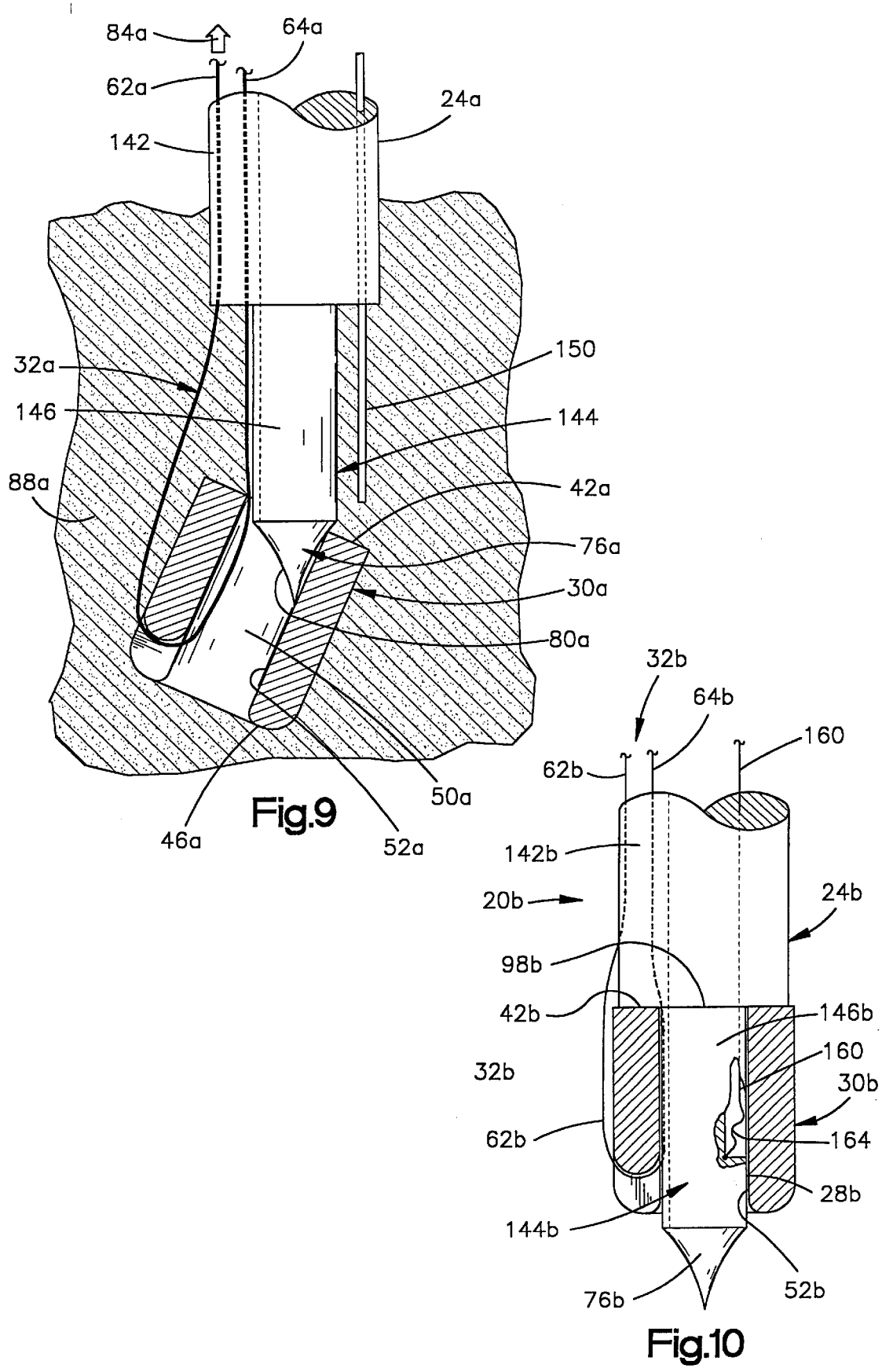

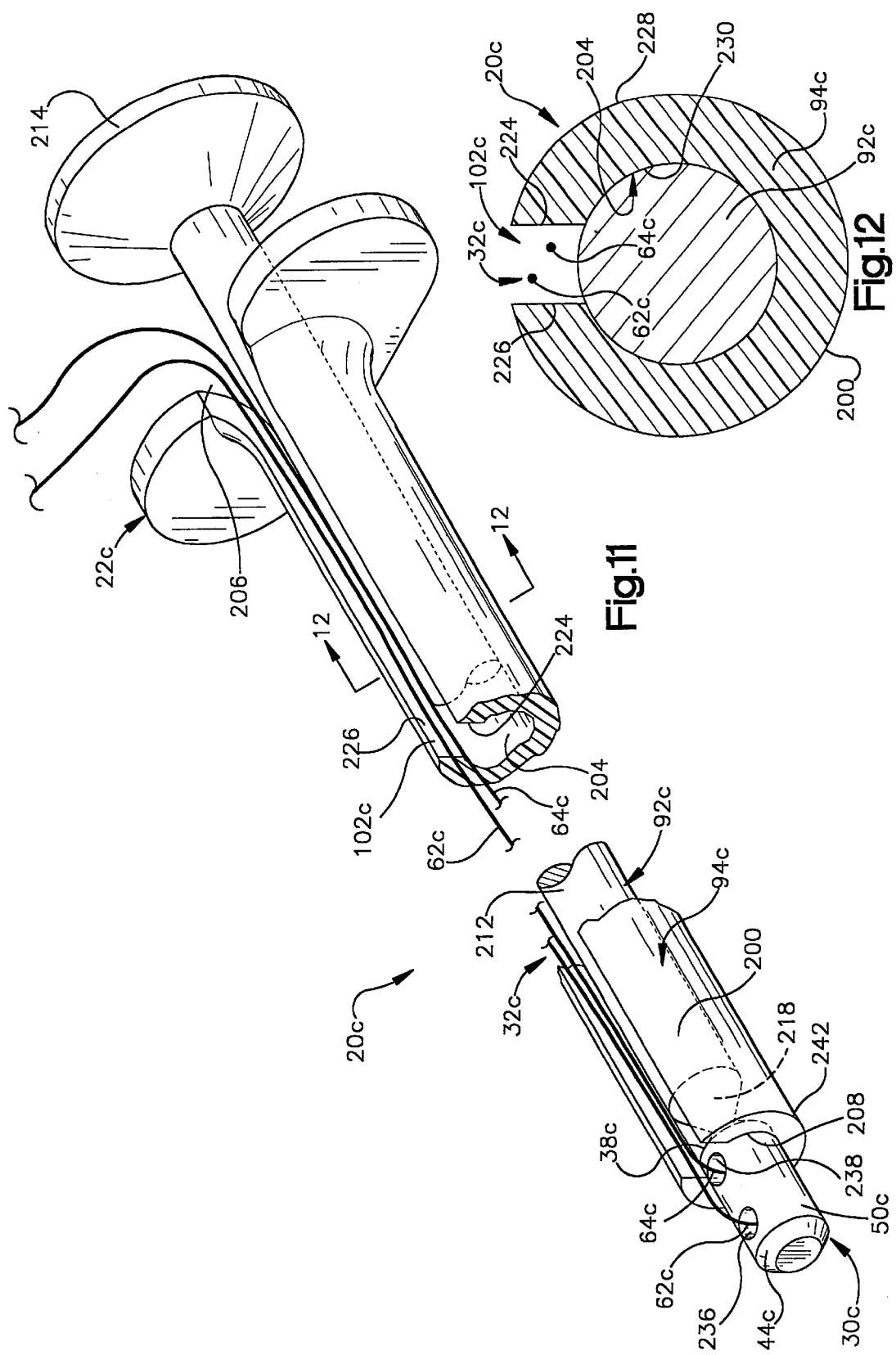

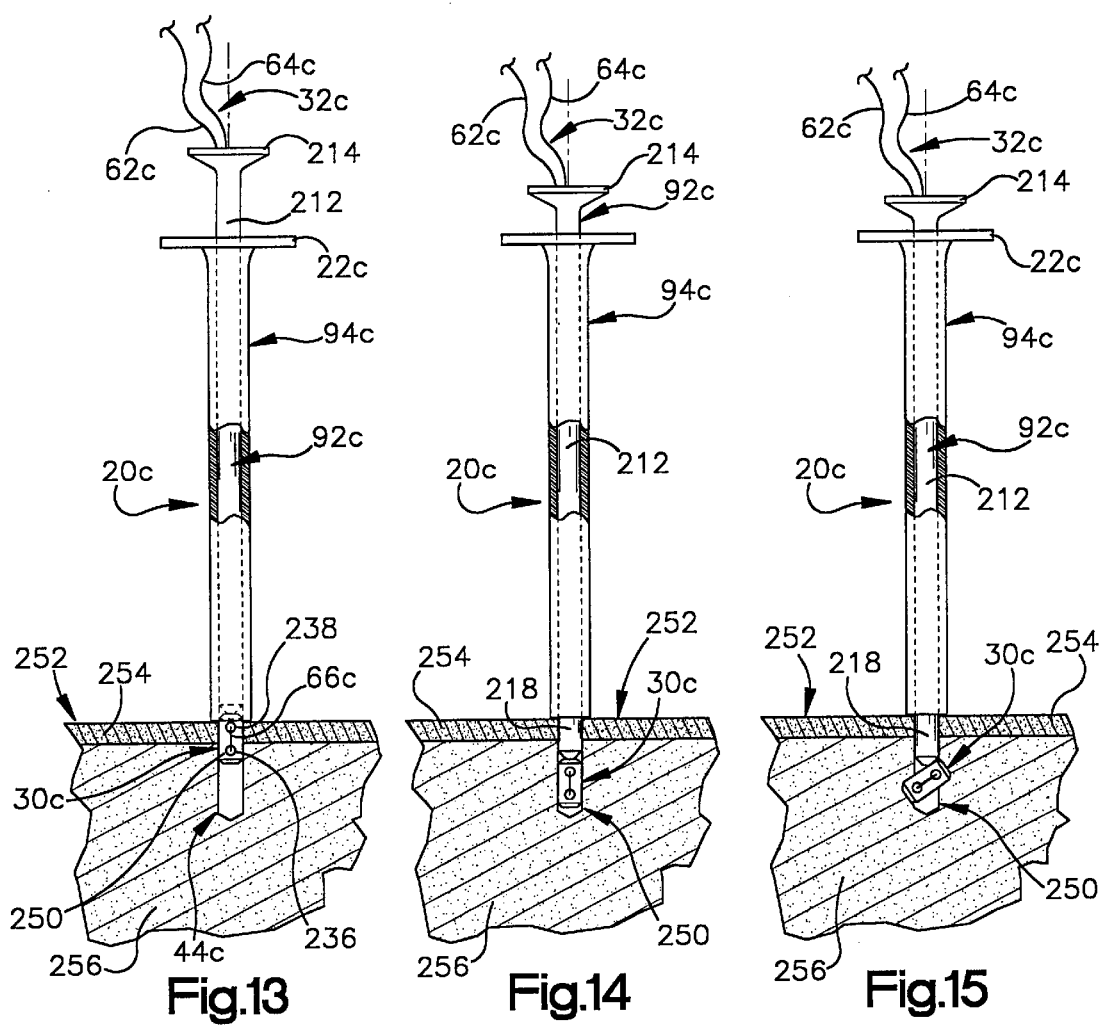

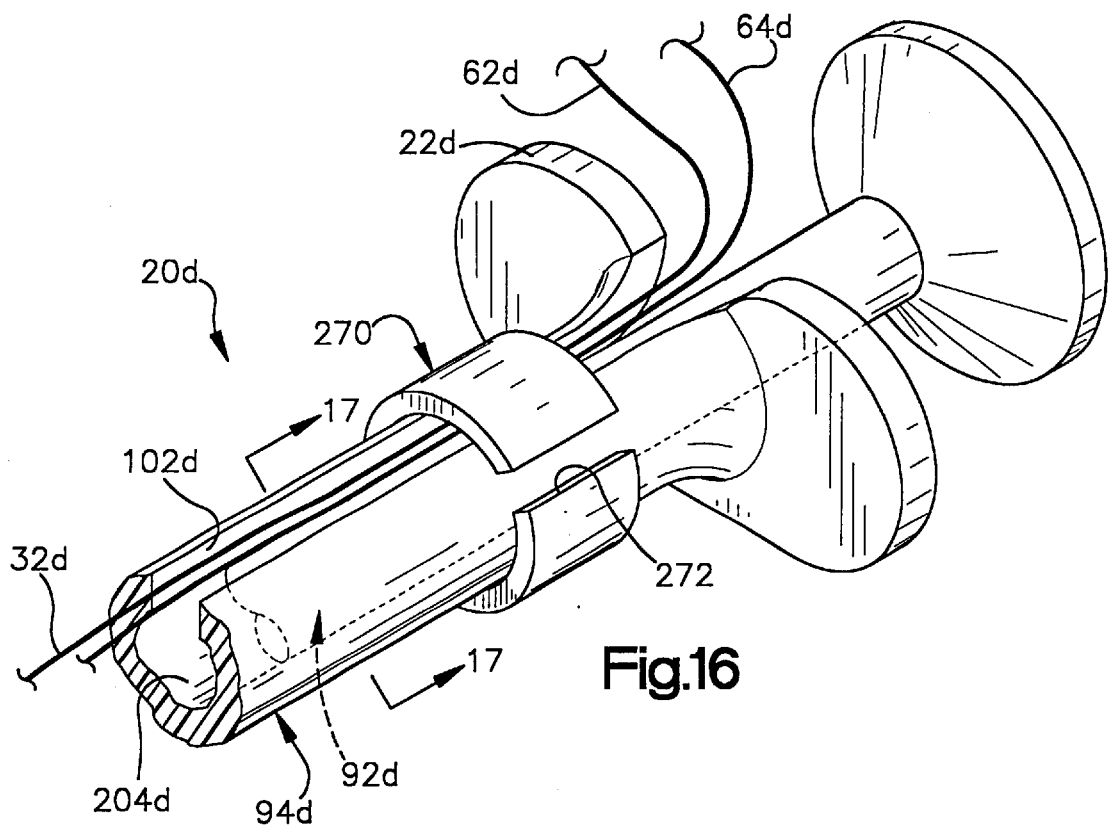
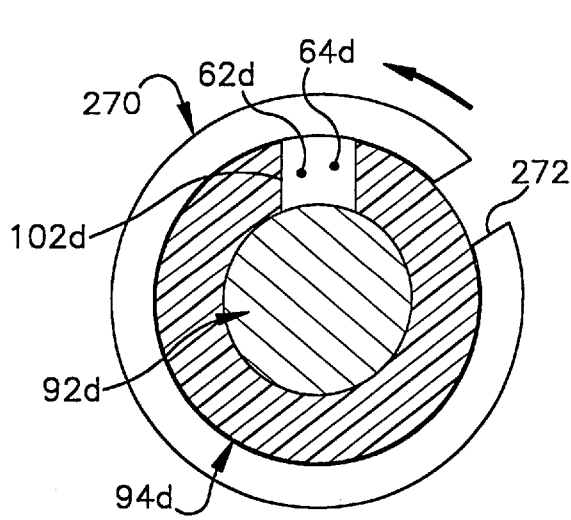 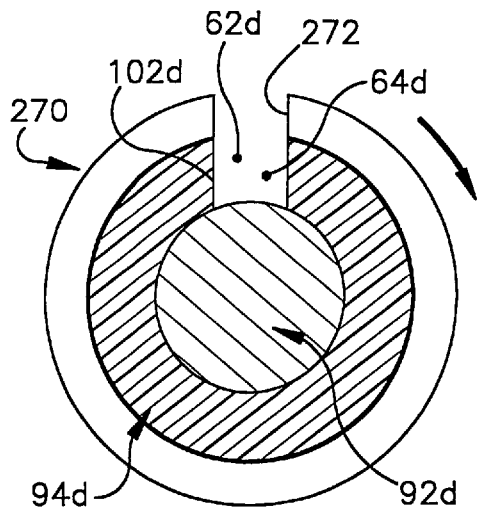

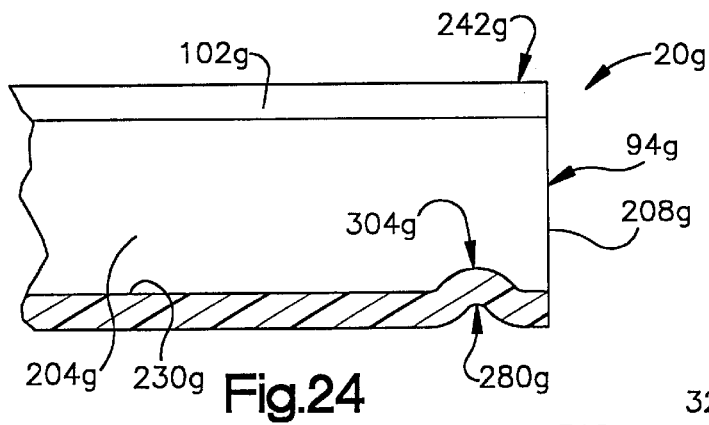
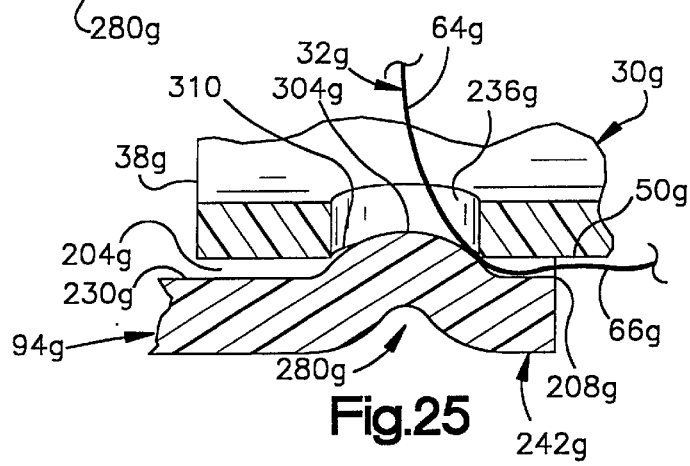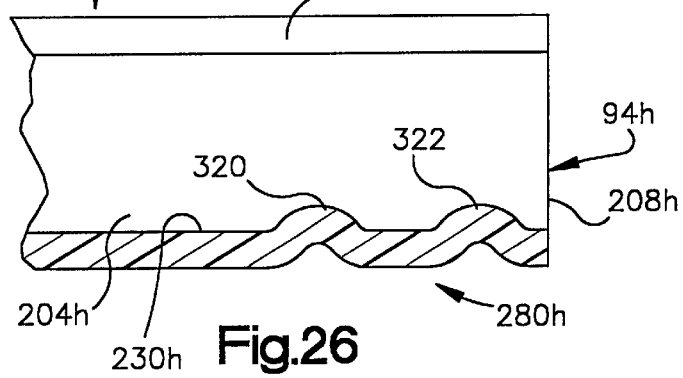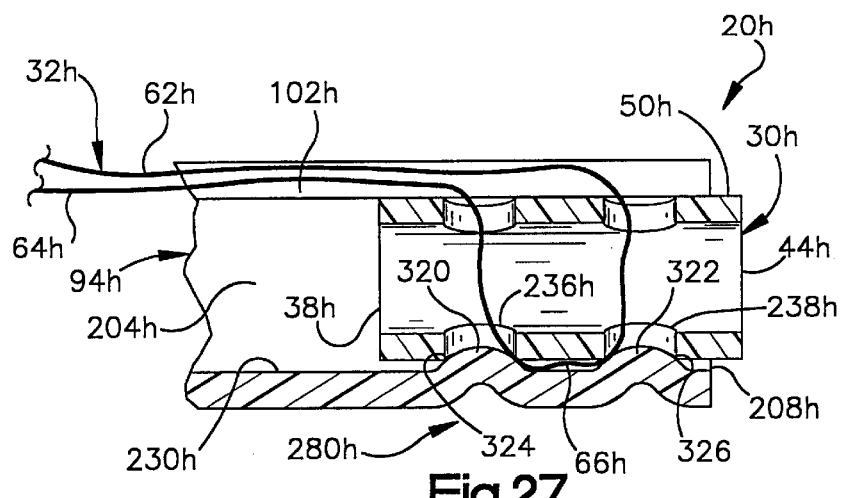

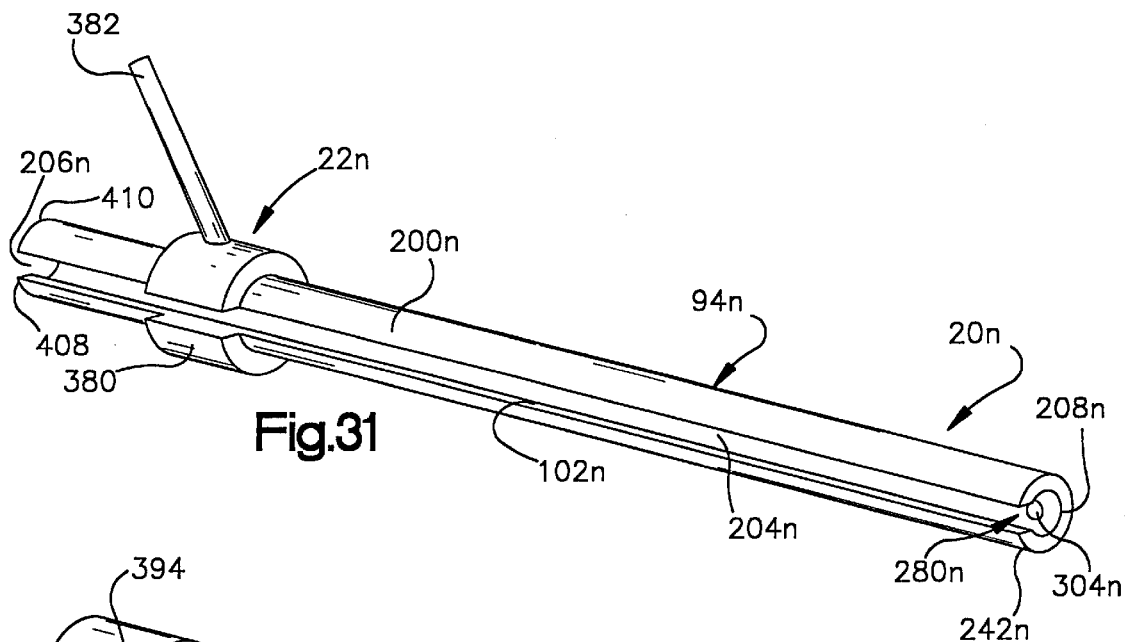
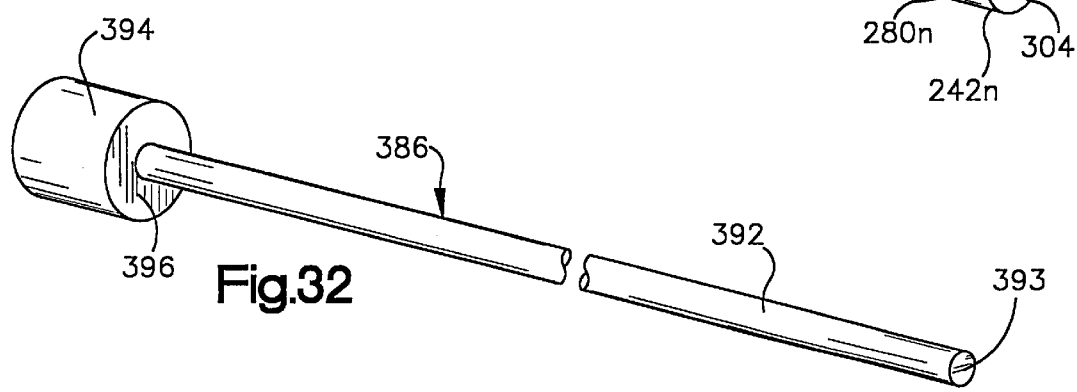
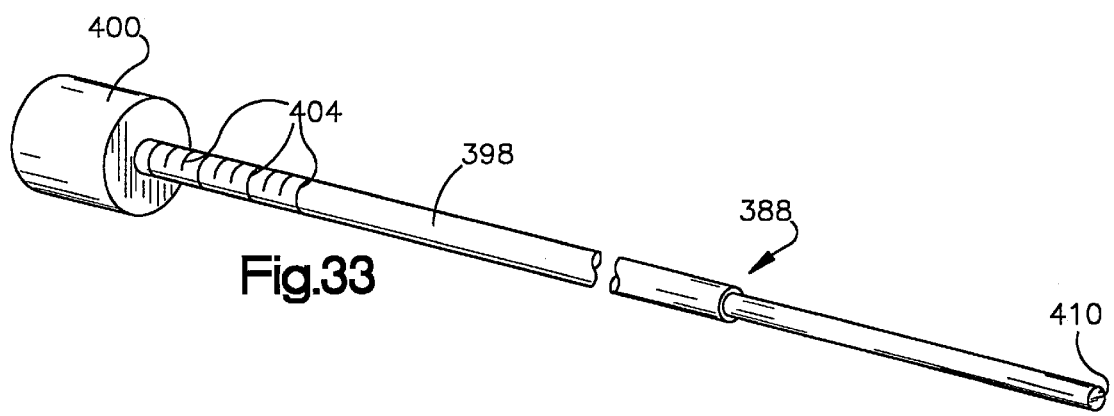

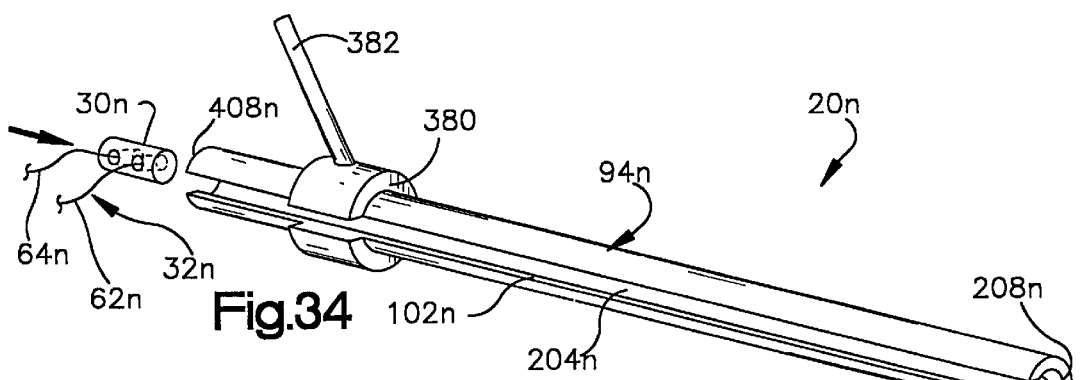
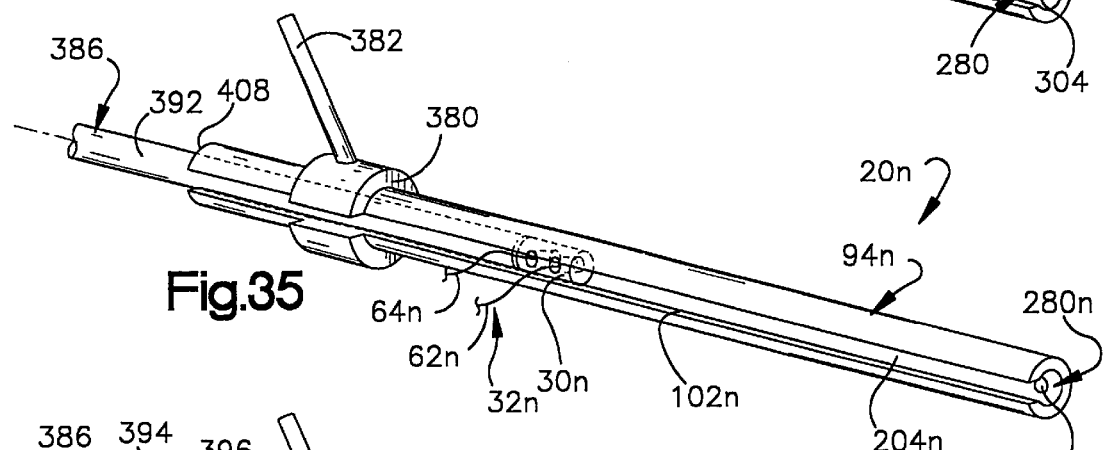
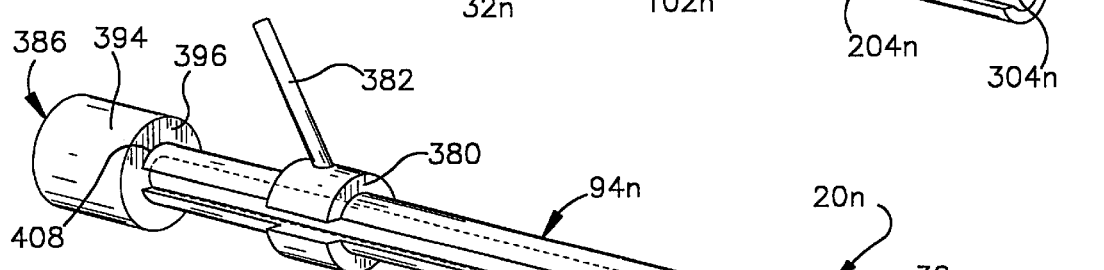
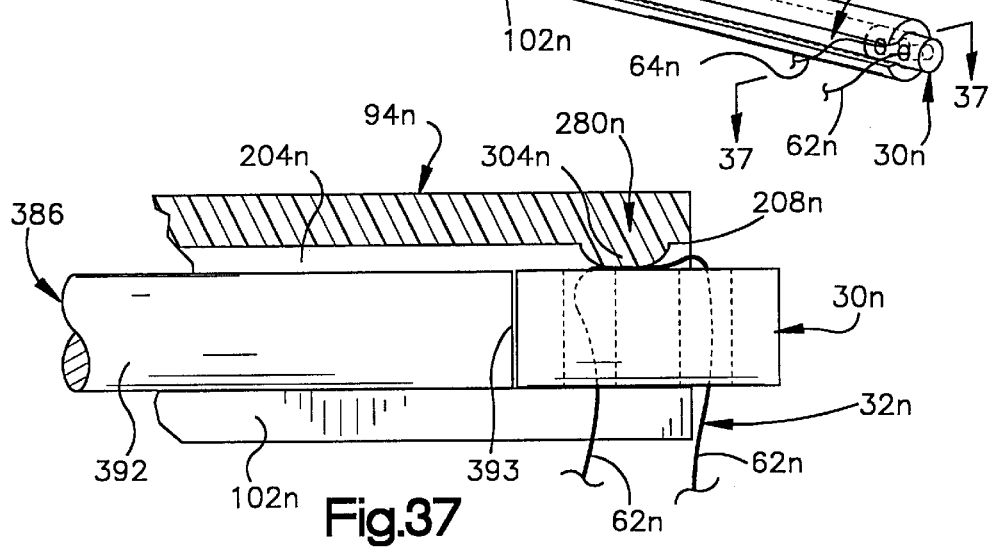

APPARATUS AND METHOD FOR USE IN POSITIONING AN ANCHOR

RELATED APPLICATION

This application is a divisional of U.S. patent application Ser. No. 09/343,371 filed Jun. 30, 1999, now U.S. Pat. No. 6,033,430. The aforementioned application Ser. No. 09/343,371 is itself a divisional of U.S. patent application Ser. No. 09/022,351 file Feb. 11, 1998, now U.S. Pat. No. 5,948,002. The aforementioned application Ser. No. 09/022,351 is itself a continuation-in-part of U.S. patent application Ser. No. 08/752,005 filed Nov. 15, 1996, now U.S. Pat. No. 5,814,072. The benefit of the earlier filing dates of the aforementioned U.S. Patent Applications has been and hereby is claimed.

BACKGROUND OF THE INVENTION

The present invention relates to a new and improved method and apparatus for use in positioning an anchor, which may be a suture anchor, relative to the apparatus and/or relative to body tissue.

A known apparatus for use in positioning a suture anchor relative to body tissue includes a tubular member in which a suture anchor and a pusher member are received. During assembly of the apparatus it is necessary to position the suture anchor and a suture relative to the tubular member. Difficulty may be encountered in positioning the suture relative to the tubular member. In addition, difficulty may be encountered in retaining the suture anchor in a desired position relative to the tubular member.

When the known suture anchor inserter apparatus is to be utilized to position a suture relative to body tissue, a surgeon may encounter difficulty in visualizing the position of the suture anchor relative to the body tissue. In addition, difficulty may be encountered in disengaging the suture anchor inserter apparatus from the suture once the suture anchor has been positioned relative to the body tissue. Known apparatus for use in positioning a suture anchor relative to body tissue are disclosed in U.S. Pat. Nos. 5,258,016; 5,354,298; 5,403,348; and 5,464,426.

SUMMARY OF THE INVENTION

The present invention relates to a new and improved method and apparatus for use in positioning an anchor during assembly of the apparatus. The present invention also relates to a new and improved method and apparatus for use in positioning an anchor relative to body tissue. The apparatus includes a tubular outer member and an inner member which is received in a passage in the tubular outer member.

A slot may extend between openings at opposite ends of the tubular outer member. During positioning of the anchor relative to body tissue, the slot facilitates visualization of the anchor by a surgeon. Stop surfaces may be provided in association with the inner and outer members to facilitate moving the anchor to a desired position relative to the inner and outer members during relative movement between the inner and outer members.

In addition, the apparatus may include a retainer which holds an anchor in a desired position relative to the apparatus during assembly of the apparatus and during positioning of the anchor relative to body tissue. The retainer is deflected under the influence of force applied against the retainer by the anchor to enable the retainer to grip the anchor and hold the anchor in the desired position.

The retainer may engage a recess in the anchor. The recess may be formed by a passage in the anchor. Alternatively, the recess may be formed in an outer side surface of the anchor.

During positioning of the anchor relative to body tissue, the tubular outer member may be utilized as a guide for a drill which forms an opening in the body tissue. After the opening has been formed in the body tissue, the drill is removed from the tubular outer member and the anchor is moved along the tubular outer member into the body tissue.

BRIEF DESCRIPTION OF THE DRAWINGS

The foregoing and other features of the invention will become more apparent upon a consideration of the following description taken in connection with the accompanying drawings wherein:

FIG. 1 is a simplified schematic illustration of the manner in which one apparatus constructed in accordance with the present invention may be utilized to position an anchor, which may be a suture anchor, in body tissue;

FIG. 2 is an enlarged fragmentary sectional view further illustrating the relationship between the anchor, a tubular outer member and an inner member of the apparatus of FIG. 1;

FIG. 3 is a sectional view, taken generally along the line 3—3 of FIG. 2, illustrating the relationship between the tubular outer member and inner member of the apparatus;

FIG. 6 is a schematic illustration, generally similar to FIG. 1, illustrating a second embodiment of the apparatus;

FIG. 7 is an enlarged fragmentary sectional view illustrating the relationship between an anchor and a one-piece shaft of the apparatus of FIG. 6;

FIG. 8 is a sectional view, taken generally along the line 8—8 of FIG. 7 further illustrating the construction of the shaft of the apparatus;

FIG. 9 is a schematic illustration depicting the manner in which the orientation of the anchor may be changed in body tissue with the apparatus of FIGS. 6–8;

FIG. 10 is a schematic illustration depicting the relationship between an end portion of a shaft of a third embodiment of the apparatus and an anchor;

FIG. 11 is a fragmentary schematic pictorial illustration of one embodiment of another apparatus which is constructed and assembled in accordance with the present invention and is utilized to position an anchor, which may be a suture anchor, relative to body tissue;

FIG. 12 is a sectional view, taken generally along the line 12—12 of FIG. 11, illustrating the relationship between a tubular outer member and an inner member of the apparatus of FIG. 11;

FIG. 13 is a schematic illustration depicting the manner in which the apparatus of FIG. 11 is utilized to initially position an anchor relative to body tissue;

FIG. 14 is a schematic illustration, generally similar to FIG. 13, illustrating the manner in which the apparatus of FIG. 11 is utilized to move the anchor into an opening formed in the body tissue;

FIG. 15 is a schematic illustration depicting the manner in which the apparatus of FIG. 11 is utilized to change the orientation of the anchor relative to body tissue;

FIG. 16 is a fragmentary schematic pictorial illustration of a portion of an alternative embodiment of the apparatus of FIG. 11;

FIG. 17 is a sectional view, taken generally along the line 17—17 of FIG. 16, illustrating the manner in which a rotatable sleeve retains portion of a suture in a slot in a tubular outer member of the apparatus of FIG. 16, when the apparatus is used with an anchor which is a suture anchor;

FIG. 18 is a sectional view, generally similar to FIG. 16, illustrating the manner in which the sleeve is positioned relative to the tubular outer member to enable the suture to be moved out of the slot in the tubular outer member;

FIG. 24 is a schematic sectional view, generally similar to FIGS. 21 and 22, of a projection on an end portion of a tubular outer member of an apparatus which forms another embodiment of the invention having the same general construction as the embodiment of FIG. 11;

FIG. 25 is a schematic sectional view illustrating the manner in which the projection on the end portion of the tubular outer member of FIG. 24 engages an end portion of a passage in an anchor;

FIG. 26 is a schematic sectional view, generally similar to FIG. 24, of another embodiment of the invention, having the same general construction as the embodiment of FIG. 11, and illustrating a pair of projections on an end portion of a tubular outer member;

FIG. 27 is a schematic sectional view illustrating the manner in which the projections of FIG. 26 engage the end portions of a pair of passages in an anchor;

FIG. 31 is a schematic pictorial illustration of a tubular outer member which forms a portion of another embodiment of the invention;

FIG. 32 is a schematic pictorial illustration of an inner member which is utilized to position an anchor relative to the tubular outer member of FIG. 31;

FIG. 33 is a schematic pictorial illustration of an inner member which is used to move an anchor out of the tubular outer member of FIG. 31;

FIG. 34 is a schematic pictorial illustration depicting the manner in which an anchor is inserted into the tubular outer member of FIG. 31;

FIG. 35 is a schematic pictorial illustration depicting the manner in which the anchor is moved along a passage in the tubular outer member of FIG. 31 by the inner member of FIG. 32;

FIG. 36 is a schematic pictorial illustration depicting the manner in which the anchor is positioned relative to the tubular outer member of FIG. 31 by the inner member of FIG. 32;

FIG. 37 is a schematic sectional view, taken generally along the line 37—37 of FIG. 36, illustrating the manner in which a projection on an outer end portion of the tubular outer member of FIG. 31 engages an outer side surface of the anchor after the anchor has been positioned by the inner member of FIG. 32;

DESCRIPTION OF ONE SPECIFIC PREFERRED EMBODIMENT OF THE INVENTION

Anchor Inserter

Figure 4:
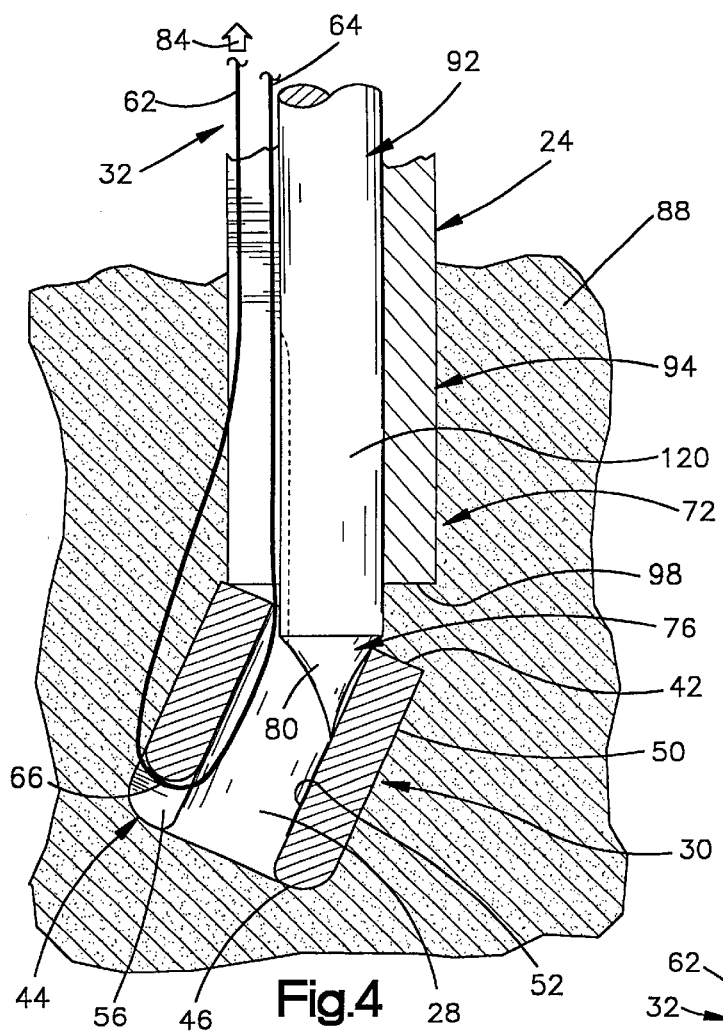
FIG. 4 is a schematic illustration depicting the manner in which the orientation of an anchor may be changed in the body tissue of FIG. 1.

An anchor inserter apparatus 20, constructed in accordance with the present invention, is illustrated in FIG. 1. The apparatus 20 includes a manually engageable handle 22 and a shaft 24 which extends from the handle. A leading end portion 26 (FIG. 2) of the apparatus 20 extends through a passage 28 in an anchor 30. The specific anchor 30 illustrated in FIG. 2 happens to be a suture anchor. A suture 32 engages the anchor 30. The anchor 30 could have a construction other than the illustrated construction. The anchor 30 could be constructed so as to be used without the suture 32.

The illustrated anchor 30 has a cylindrical tubular side wall 36 (FIG. 2). A trailing end portion 38 of the anchor 30 has a flat annular trailing end surface 42. In addition, the anchor 30 has a leading end portion 44. The leading end portion 44 of the anchor 30 has an annular leading end surface 46.

The tubular side wall 36 of the anchor 30 has a cylindrical outer side surface 50 which extends between the trailing end surface 42 and the leading end surface 46. In addition, the illustrated anchor 30 has a cylindrical inner side surface 52 which is disposed in a coaxial relationship with the outer side surface 50. The cylindrical inner side surface 52 forms the passage 28 which extends between the trailing end surface 42 and leading end surface 46 of the anchor 30.

A groove or slot 56 is formed in the leading end portion 44 of the anchor 30. The groove or slot 56 extends axially inward from the leading end surface 46 and extends radially between the outer and inner side surfaces 50 and 52 of the anchor 30. The slot or groove 56 has an arcuately curving inner side surface 58 across which the suture 32 extends. It is contemplated that the slot or groove 56 may be omitted if desired.

The suture 32, which is used with the specific anchor 30 illustrated in FIGS. 1 and 2, has an outer leg 62 which extends along the outer side surface 50 of the anchor. An inner leg 64 of the suture 32 extends through the passage 28 and along the inner side surface 52 of the anchor 30. The outer leg 62 and inner leg 64 of the suture 32 are interconnected by a connector section 66 of the suture. The connector section 66 of the suture 32 extends through the slot 56 in the side wall 36 of the anchor 30. If the anchor 30 is constructed without the slot 56, the connector section 66 of the suture 32 would extend across the leading end surface 46 of the anchor.

The anchor 30 is made of a biocompatible material, specifically, stainless steel. The anchor 30 has a length, that is, the distance between the trailing end surface 42 and leading end surface 46, of approximately two millimeters. The anchor 30 has an outside diameter, that is, the diameter of the outer side surface 50, of approximately one millimeter. The inner side surface 52 has a diameter of about one-half millimeter. It should be understood that the foregoing specific dimensions for one specific anchor 30 have been set forth herein only for purposes of clarity of description. It is contemplated that the anchor 30 will be constructed with dimensions which are different than the dimensions set forth above.

The illustrated anchor 30 has a cylindrical tubular side wall 36. It should be understood that the anchor 30 could have a different configuration. For example, the anchor 30 could have a polygonal cross sectional configuration if desired. Thus, the anchor 30 could have a polygonal configuration which is similar to the polygonal configuration of an anchor disclosed in U.S. Pat. No. 5,549,630 issued Sep. 27, 1996 to Peter M. Bonutti.

Although the anchor 30 is formed of metal, it is contemplated that the anchor 30 could be formed of other materials if desired. For example, the anchor 30 could be formed of body tissue. Alternatively, the anchor 30 could be formed of a polymeric material such as cellulose, petroylglutamic acid, collagen, or polylactide. It is believed that a ceramic as found in hydroxyapatite composites with polyethylene, polylactide or polyhydroxybutyrate may be utilized to form the anchor 30. If desired, the anchor 30 may be formed of a material which is hydrophilic and expands when exposed to body fluids.

The shaft 24 has a leading end portion 72 (FIGS. 1 and 2) which is used to penetrate human body tissue. The leading end portion 72 of the shaft extends through the anchor 30. The leading end portion 72 of the shaft 24 may have a point 76 which extends ahead of the leading end surface 46 of the anchor 30.

The illustrated point 76 on the inserter shaft 24 has a conical configuration with a central axis which is coincident with a central axis of the inserter shaft and anchor 30. However, if desired, the point 76 could have a wedge-shaped configuration. Similarly, the point 76 could be formed by a single flat plane which is skewed at an acute angle to a longitudinal central axis of the shaft 24. Alternatively, the leading end of the shaft 24 could have a rounded or even a flat configuration.

The leading end portion 72 of the shaft 24 extends through the passage 28 in the anchor 30. The point 76 on the leading end of the shaft 24 is disposed ahead of and is coaxial with the anchor 30. This enables the point 76 to pierce body tissue ahead of the anchor 30. Although it is believed that the provision of the point 76 on the leading end of the shaft 24 will facilitate the piercing of human body tissue, the cross sectional size of the leading end of the shaft may be so small as to enable the shaft to pierce body tissue with a blunt end.

By piercing the body tissue with the point 76, an opening is initially formed by the leading end portion 72 of the shaft 24. The shaft 24 moves the anchor into the opening which was initially formed by the point 76. The leading end surface 46 on the anchor 30 is sloped to form a continuation of a surface 80 on the point 76. The sloping leading end surface 46 on the anchor 30 promotes a smooth enlargement of the opening formed in the elastic material of the human body tissue by the point 76 on the leading end of the shaft 24. Although the point 76 is advantageously used to pierce soft body tissue, the inserter 20 may be used to position anchors 30 in preformed openings in hard body tissue, such as bone.

Figure 5:
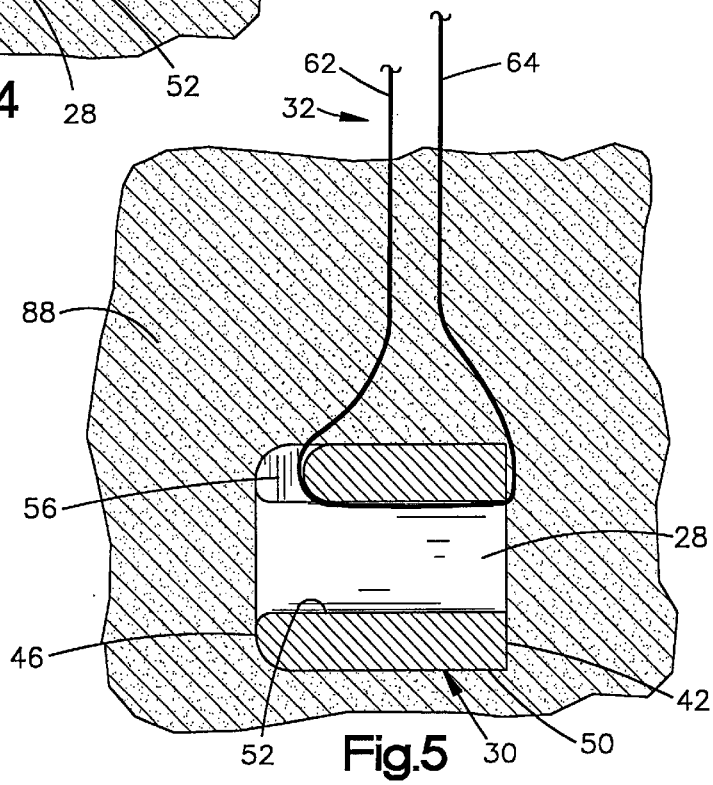
FIG. 5 is a schematic illustration depicting the suture anchor of FIG. 4 after the anchor has been moved to a desired orientation in the body tissue.

The shaft 24 may be used to promote movement of the anchor 30 in human body tissue in such a manner as to change the orientation of the anchor relative to the body tissue and the shaft 24. Thus, it may be desired to change the orientation of the anchor 30 relative to the shaft 24 from the orientation shown in FIG. 1 to the orientation shown in FIG. 5. However, it should be understood that the inserter 20 may also be used to position anchors 30 which remain in the orientation shown in FIG. 1 relative to the body tissue.

When the anchor 30 is used with a suture and it is desired to change the orientation of an anchor 30 relative to body tissue, a leg 62 of the suture 32 is tensioned in the manner indicated by an arrow 84 in FIG. 4. At the same time, the point 76 on the shaft 24 engages the inner side surface 52 of the passage 28 through the anchor 30. This results in the application of a torque to the anchor 30 tending to rotate the anchor in a clockwise direction (as viewed in FIG. 4) from the orientation shown in FIG. 1 through the orientation shown in FIG. 4, toward the orientation shown in FIG. 5.

As this occurs, the cylindrical outer side surface 50 of the anchor is pressed against the elastic material of human body tissue 88 and deforms the body tissue. Once the anchor has been moved to the orientation shown in FIG. 5, pulling out of the anchor from the body tissue 88 is resisted by the relatively large outer side surface 50 of the anchor. This enables the anchor to remain stable in the body tissue 88 even though relatively large forces are applied to the legs 62 and 64 of the suture 32. Although the foregoing description has related to the changing of the orientation of the anchor 30 in soft body tissue, the inserter 20 may be used to change the orientation of an anchor in cancellous bone tissue in the same manner as previously set forth in association with soft body tissue.

The foregoing description has been in conjunction with an anchor 30 which is used with a suture 32. However, the suture 32 could be omitted if desired. If this is done, the anchor 30 would be used to retain body tissue.

Inserter

The anchor inserter 20 (FIG. 1) includes a handle 22 having a configuration suitable for manual grasping by a surgeon. The illustrated handle 22 has a generally cylindrical configuration with circumferentially extending grooves to facilitate firm gripping of the handle. However, if desired, the handle 22 could be formed with a generally triangular cross sectional configuration in a manner similar to that disclosed in U.S. application Ser. No. 08/673,923 filed Jul. 1, 1996 and entitled "Suture Anchor Inserter Assembly and Method" by Peter M. Bonutti. The disclosure in the aforementioned application Ser. No. 08/673,923 is incorporated herein in its entirety by this reference thereto.

The shaft 24 extends axially outward from the handle 22. The shaft 24 has a generally cylindrical configuration and is disposed in a coaxial relationship with the handle 22. However, the shaft 24 could have a different configuration if desired. For example, if the passage 28 through the anchor 30 had a polygonal cross sectional configuration, the shaft 24 could have a corresponding polygonal cross sectional configuration.

In accordance with a feature of the embodiment of the inserter 20 illustrated in FIGS. 1–3, the shaft 24 includes a cylindrical inner member 92 and cylindrical outer member 94 which are movable relative to each other. The upper (as viewed in FIGS. 1 and 2) end of the solid cylindrical inner member 92 is fixedly connected with the handle 22. The point 76 is disposed on the lower (as viewed in FIGS. 1 and 2) end of the inner member 92. The point 76 extends ahead of the leading end portion 44 of the anchor 30 to initiate formation of an opening into which the anchor moves.

As was previously mentioned, the point 76 could be formed with a configuration other than the illustrated conical configuration. In fact, it is contemplated that the point 76 may be eliminated on some embodiments of the inserter. Although it is preferred to have the inner member 92 extend through the passage 28 and extend ahead of the leading end portion 44 of the anchor 30, the leading end of the inner member 92 could be disposed in the anchor if desired.

The outer member 94 has a tubular cylindrical configuration and partially encloses the solid inner member 92. The outer member 94 is axially movable relative to the inner member 92. The outer member 94 has a flat annular pusher surface 98 which engages the flat annular trailing end surface 42 of the anchor 30.

The inner and outer members 92 and 94 are both formed of metal, specifically stainless steel. However, the inner and outer members 92 and 94 could be formed of other materials if desired. For example, the inner member 92 could be formed of metal and the outer member 94 could be formed of a polymeric material.

The outer member 94 is axially movable along the inner member 92 between a retracted position, shown in FIGS. 1 and 2, and a fully extended position in which the pusher surface 98 is adjacent to the lower (as viewed in FIG. 2) end of the point 76. Thus, the outer member 94 is movable axially along the inner member 92 from the position shown in FIGS. 1 and 2 through the position shown in FIG. 4 to a position in which the annular pusher surface 98 is a short distance past the outer end of the point 76.

In accordance with one of the features of the present invention, a slot or groove 102 (FIG. 3) extends through a tubular cylindrical side wall of the outer member 94. The straight slot or groove 102 in the outer member 94 extends between opposite ends of the outer member 94 and is axially aligned with a passage, that is a slot, which extends through the handle 22. The two legs 62 and 64 of the suture 32 extend through the slot 102 and the passage in the handle 22 to a location disposed above (as viewed in FIG. 1) the handle.

The inner leg 64 of the suture 32 extends through the passage 28 (FIG. 2) in the anchor 30. The leading end portion of the inner member 92 also extends through the passage 28 in the anchor 30. In the illustrated embodiment of the inserter 20, a straight slot or groove 106 extends axially along the inner member 92 from the point 76 to a location which is disposed above (as viewed in FIG. 2), the pusher surface 98 when the outer member 94 is in the retracted position. The inner leg 64 of the suture then extends from the slot 106 in the inner member 92 into the slot 102 in the outer member 94. The slot 106 in the inner member 92 terminates at a location disposed axially above (as viewed in FIG. 2) the pusher surface 98 when the pusher surface is in the retracted position.

An actuator 110 is provided to move the outer member 94 axially along the inner member 92. The actuator 110 (FIG. 1) includes a manually engageable knob or input member 112 which is connected to the outer member 94 and extends through a slot 114 formed in the handle 22. The slot 114 has an axial extent which corresponds to the distance which the outer member 94 can be moved axially along the inner member 92. When the outer member 94 is in the fully retracted position of FIG. 1, the knob 112 is adjacent to an upper end of the slot 114.

After the anchor 30 has been moved into body tissue 88 and is to remain in the orientation shown in FIG. 1, the actuator knob 112 is moved downward (as viewed in FIG. 1) in the slot 114. As this occurs, force is transmitted between the pusher surface 98 and the trailing end surface 42 of the anchor 30. At the same time, the shaft 24 may be moved straight upward (as viewed in FIG. 1).

The relative movement between the anchor 30 and inner member 92 results in the trailing end surface 42 of the anchor 30 being moved in alignment with the base or upper end of the point 76. When this has happened, a cylindrical outer side or positioning surface 120 on the inner member 92 is disposed above (as viewed in FIG. 2) the annular trailing end surface 42 of the anchor 30. Continued relative movement between the inner and outer members 92 and 94 at least partially withdraws the point 76 from the passage 28 in the anchor 30. The handle 22 of the inserter 20 can then be moved or pulled upward away from the body tissue 88 and the point 76 of the shaft 24 moved completely out of the anchor 30. This results in the anchor 30 remaining in the orientation shown in FIG. 1 in the body tissue 88.

As the outer member 94 is moved axially downward (as viewed in FIGS. 1 and 2) to separate the anchor from the shaft 24, the extent of the telescopic relationship between the portions of the inner and outer members 92 and 94 disposed in the handle 22 is decreased. Thus, when the outer member 94 is in the fully retracted position shown in FIG. 1, the extent to which the portion of the inner member 92 disposed in the handle is enclosed by the outer member 94 is a maximum. As the actuator knob 112 is moved downward (as viewed in FIG. 1) in the slot 114, a portion of the outer member 94 moves out of the handle 22 and the extent of the telescopic relationship between the inner and outer members 92 and 94 in the handle 22 decreases.

The length of the slot 114 is great enough to enable the pusher surface 98 to move along the length of the point 76. When the actuator knob 112 has reached the lower end (as viewed in FIG. 1) of the slot 114, the upper end portion of the outer member 94 is still in the handle 22. At this time, the pusher surface 98 has moved to a location just past the point 76. Therefore, the point 76 is fully enclosed by the outer member 94.

It should be understood that a surgeon using the inserter 20 can determine the extent of relative movement between the inner and outer members 92 and 94. The surgeon may move the actuator knob 112 through only a portion of the length of the slot 114. Suitable indicia may be provided along the slot 114 to indicate the position of the pusher surface 98 relative to the point 76.

In the embodiment of the invention illustrated in FIG. 1, the actuator knob 112 is connected directly with the outer member 94 and is movable in the slot 114 in the handle 22. However, it is contemplated that the actuator knob 112 and the slot 114 could be eliminated and suitable knurling and/or projections provided on the outer member 94. The knurling or projections on the outer member 94 may be manually engaged and force transmitted directly from the hand of a surgeon to the outer member. If force is to be manually applied directly to the outer member 94, the outer member could either extend into the handle 22 or terminate short of the handle.

Insertion of Anchor

When the anchor 30 is to be inserted into body tissue 88, the optional suture 32 extends through the passage 28 in the anchor 30. The legs 62 and 64 of the suture 32 extend along the slot 102 in the outer member 94 and through the passage (not shown) in the handle 22. However, if desired, the legs 62 and 64 of the suture 32 could extend along the outside of the shaft 24 and handle 22. If desired, the suture 32 could be omitted.

The anchor 30 is then positioned on the leading end portion 26 of the inserter 20. Since the specific anchor 30 illustrated in the drawings is a suture anchor, the suture 32 extends through the passage 28 in the anchor and with the outer member 94 in the retracted position of FIGS. 1 and 2. It should be understood that the suture 32 could be connected with the anchor 30 in a manner other than by extending through the passage 28. For example, an opening could be provided in the anchor 30 at a location spaced from the passage 28. The suture 32 could extend through or be tied off at this opening.

To position the anchor 30 on the leading end portion 26 of the shaft 24, the point 76 on the inner member 92 is inserted into the passage 28 in the anchor 30. The slot 106 in the inner member 92 is aligned with the inner leg 64 of the suture. The anchor is then moved along the inner member 92 until the trailing end surface 42 on the anchor moves into abutting engagement with the pusher surface 98 on the outer member 94. At this time, the point 76 on the inner member 92 extends outward from and is coaxial with the end surface 46 of the anchor 30. The suture 32 is then tensioned to hold the anchor 30 in place.

The point 76 on the inner member 92 is then moved into engagement with an imperforate outer surface 130 (FIG. 1) on a human patient's skin 132. Manual force is applied to the handle 22 to cause the point 76 on the inner member 92 to pierce the surface 130. As this occurs, a circular opening is formed in the skin 132 by the point 76 of the inner member 92. This opening is formed directly ahead of and in axial alignment with the anchor 30.

The manual application of downward (as viewed in FIG. 1) force against the handle 122 moves the point 76 of the inner member 92 through the skin 132 into flesh 134 disposed beneath the skin. As this occurs, the leading end portion 44 of the anchor 30 moves into the opening which was initially formed by the point 76 on the inner member 92. The annular pusher surface 98 on the outer member 94 presses against the annular trailing end surface 42 of the anchor 30 to push the anchor into the body tissue.

Movement of the leading end portion 44 of the anchor 30 into the opening formed by the point 76 in the body tissue is facilitated by having at least a portion of the leading end surface 46 of the anchor 30 slope radially outward as a continuation of the surface 80 on the point 76. As the leading end 44 of the anchor 30 is pressed against the viscoelastic body tissue 88, the initial opening is elastically expanded and the anchor 30 moves into the flesh 134 disposed beneath the skin 132. The point 76 pierces the flesh 134 ahead of the anchor 30 to initiate the formation of an opening in the flesh for the anchor.

Continued application of force to the handle 22 results in the shaft 24 moving the anchor 30 to a desired depth in the body tissue 88. As this occurs, the point 76 on the inner member 92 continues to penetrate or pierce the body tissue 88 ahead of the anchor 30. This facilitates movement of the shaft 24 and anchor 30 into the body tissue 88.

The anchor 30 is moved into the body tissue 88 under the influence of force transmitted from the pusher surface 98 on the outer member 94 to the trailing end surface 42 of the anchor. Thus, as the shaft 24 and anchor 30 move into the body tissue 88, the outer member 94 is stationary relative to the inner member 92. The pusher surface 98 on the outer member 94 presses against the trailing end portion 38 of the anchor 30 with a force sufficient to move the anchor into the body tissue 88.

Once the anchor 30 has been moved into the body tissue 88, the anchor and shaft 24 are separated. When this is to be done, any tension in the legs 62 and 64 of the suture is eliminated. The actuator knob 112 is then moved downward (as viewed in FIG. 1) along the slot 114. As this occurs, relative movement between the anchor 30 and the inner member 92 results in the point 76 (FIG. 2) on the inner member being circumscribed by the tubular side wall 36 of the anchor.

When the anchor 30 is being separated from the inserter 20, the anchor may be pushed off of the end of the inner member 92 by the outer member 94 while the inner member remains stationary relative to the body tissue. Alternatively, the handle 22 and inner member 92 may be moved upwardly and the anchor 30 and outer member 94 maintained stationary relative to the body tissue. It is contemplated that, in all probability, there will be a combined movement of the anchor 30 and outer member 94 axially along the inner member 92 and withdrawal of the inner member from the body tissue as the anchor is separated from the shaft 24.

Changing Anchor Orientation

As the anchor 30 is separated from the shaft 24, it may remain in the orientation shown in FIG. 1 relative to the body tissue 88 and the shaft. Alternatively, the anchor 30 may be moved through the orientation shown in FIG. 4 to the orientation shown in FIG. 5. At least a portion of this movement of the anchor 30 occurs while the leading end portion 26 of the inserter 20 is in the passage 28 in the anchor.

During movement of the anchor 30 to a desired depth in the body tissue 88 (FIG. 1), the outer side surface 120 on the inner member 92 positions the anchor in a coaxial relationship with the inner member 92 and retains the anchor against pivotal movement. When the anchor 30 has been moved to the desired depth in the body tissue 88, the actuator 110 is manually operated. This causes relative movement between the inner and outer members 92 and 94.

As relative movement occurs between the inner and outer members 92 and 94, the point 76 on the outer member and the pusher surface 98 on the inner member move toward each other (FIG. 4). As this occurs, the positioning surface 120 on the inner member 92 almost moves out of the passage 28 in the anchor 30 (FIG. 4). This releases the anchor 30 for pivotal movement relative to the shaft 24. Although a major portion of the positioning surface 120 has been withdrawn from the anchor passage 28, the point 76 on the inner member 92 and the outermost portion of the positioning surface 120 are disposed in the passage 28 in the anchor.

Pivotal movement of the anchor 30 is then initiated by tensioning the outer leg 62 of the suture 32, as indicated by the arrow 84 in FIG. 4. The tension force applied to the leading end portion 44 of the anchor 30 causes it to rotate in a clockwise direction toward the position shown in FIG. 4. As the anchor approaches the position shown in FIG. 4, the inner side surface 52 on the anchor 30 moves into engagement with the outer side surface 80 on the point 76. This results in the transmittal of force from the outer side surface 80 of the point 76 to the inner side surface 52 of the anchor 30 in a downward (as viewed in FIG. 4) direction to further promote pivotal movement of the anchor in a clockwise direction.

As the outer member 94 continues to push downward (as viewed in FIG. 4) against the trailing end surface 42 of the anchor 30, the anchor continues to pivot relative to the shaft 24. The anchor 30 pivots about a location where the trailing end surface 42 of the anchor engages the outer member 94. In addition, the anchor 30 pivots about a location where the point 76 engages the inner side surface 52 of the anchor. This combined pivotal movement is caused by the tension in the outer leg 62 of the suture 32.

As the pusher surface 98 approaches and then moves past the base of the point 76, the point moves out of the passage 28 through the anchor 30. The anchor 30 then continues to pivot in a clockwise direction under the influence of the force applied to the anchor by the tension in the outer leg 62 of the suture 32. This force causes the anchor to move to the position shown in FIG. 5, or at least to a position closely approximating the position shown in FIG. 5. Once the anchor 30 has moved to the position shown in FIG. 5 relative to the body tissue 88, the relatively large outer side surface 50 of the anchor resists pulling out of the anchor from the body tissue. Therefore, relatively large forces can be transmitted through the suture 32 to the anchor 30 without pulling the anchor out of the body tissue.

When the anchor 30 is to be inserted into bone with the inserter 20, an opening is drilled through the hard outer layer of the bone into the soft inner material of the bone. Once this has been done, the inserter 20 is used to position the anchor 30 in the spongy cancellous tissue within the bone. The orientation of the anchor 30 may be changed, relative to the bone, in the same manner as previously explained herein.

It should be understood that it is contemplated that the inserter 20 may be used to position an anchor 30 in either hard or soft tissue at many different locations in a patient's body. The pointed end 76 of the inserter 20 may be used to pierce body tissue at locations remote from the patient's skin 132 (FIG. 1). Thus, the inserter 20 may be used to position an anchor in an organ disposed within the patient's body.

When the inserter 20 is to be used to position the anchor 30 in a preformed opening in hard body tissue, such as the hard outer or cortical layer of bone, the inner member 92 may not extend past the leading end portion 44 of the anchor 30. When the inserter 20 is to be used to position the anchor 30 in soft body tissue, the formation of an opening in the body tissue for the anchor 30 may be accomplished without piercing the body tissue with the inner member 92 and the inner member may not extend past the anchor. However, it is believed that it may be preferred to have the point 76 extend ahead of the anchor 30 even when the point is not to be used to pierce body tissue.

Inserter—Second Embodiment

In the embodiment of the inserter or apparatus illustrated in FIGS. 1–5, the shaft 24 is formed by two members, that is, the inner member 92 and the outer member 94. In the embodiment of the inserter illustrated in FIGS. 6–9, the shaft of the inserter is formed by a single member. Since the embodiment of the invention illustrated in FIGS. 6–9 is generally similar to the embodiment of the invention illustrated in FIGS. 1–5, similar numerals will be utilized to designate similar components, the suffix letter "a" being associated with the numerals of FIGS. 6–9 to avoid confusion.

An anchor inserter 20a (FIG. 6) includes a manually engageable handle 22a and a one piece shaft 24a which extends outward from the handle. A leading end portion 26a of the one piece shaft 24a extends through a passage 28a in the anchor 30a. Since the illustrated anchor 30a is a suture anchor, a suture 32a extends through the passage 28a in the anchor and along the shaft 24a. The suture 32a extends through a passage (not shown) in the handle 22a. The anchor 30a has the same construction as the anchor 30 in the embodiment of the invention illustrated in FIGS. 1–5. However, the anchor 30a could have a different construction if desired. The anchor 30a could be used without the suture 32a if desired.

The shaft 24a of the inserter 20a is formed as one piece. Thus, the shaft 24a includes a main section 142 (FIGS. 6 and 7) and a leading end section 144 (FIG. 7). The leading end section 144 includes a cylindrical positioning portion 146 which is disposed in a coaxial relationship with the cylindrical main section 142. A generally conical point 76a is formed on the leading end section 144 and has a conical outer side surface 80a.

A pusher surface 98a forms a flat annular shoulder where the cylindrical main section 142 is connected with the leading end section 144 of the shaft 24a. Since the shaft 24a is formed from a single piece of material, that is, stainless steel, the pusher surface 98a does not move relative to the point 76a of the shaft 24a. Although it is preferred to form the shaft 24a from a single piece of metal, the shaft may be formed by a solid cylindrical inner member and a cylindrical tubular outer member which is fixedly connected to the inner member. When the shaft 24a is formed by two fixedly connected members, the members may be different materials.

A slot 102a (FIGS. 7 and 8) extends from the base of the point 76a along the shaft 24a. The slot 102a extends through the handle 22a. The depth of the slot 102a is greater in the main section 142 (FIG. 7) of the one piece shaft 24a than in the leading end section 144 of the shaft. The inner and outer legs 62a and 64a of the suture 32a are received in the slot 102a (FIG. 8) when he inserter 20a is used to position a suture anchor relative to body tissue.

When the anchor 30a is to be inserted into human body tissue 88a (FIG. 6), the anchor is first positioned on the leading end section 144 of the shaft 24a with the suture 32a extending through the passage 28a in the anchor 30a. Thus, the anchor 30a is telescopically moved onto the positioning portion 146 of the leading end section 144 of the shaft 24a. As this occurs, a trailing end surface 42a on the anchor 30a is positioned in abutting engagement with the annular pusher surface 98a.

A cylindrical outer side surface 120a on the positioning portion 146 engages a cylindrical inner side surface 52a of the anchor 30a (FIG. 7). The positioning surface 120a on the leading end section 144 of the shaft 24a positions the anchor 30a in a coaxial relationship with the shaft 24a and the point 76a. When the anchor 30a is a suture anchor, the two legs 62a and 64a of the suture 32a are tensioned to hold the trailing end surface 42a of the anchor 30a in abutting engagement with the pusher surface 98a on the shaft 24a.

The point 76a on the leading end section 144 of the shaft 24a is then moved into engagement with an imperforate outer surface 130a (FIG. 6) of a human patient's skin 132a. A downward force is then manually applied to the handle 22a. This force causes the point 76a on the shaft 24a to pierce the outer side surface 130a of the skin 132a. The point 76a then moves into flesh 134a disposed beneath the skin. As this occurs, an opening is formed by the point 76a in the skin 132a.

The anchor 30a moves into the opening in the skin 132a. Force is applied against the trailing end surface 42a of the anchor 30a by the pusher surface 98a to push the anchor into the body tissue 88a. A leading end surface 46a on the anchor 30a is sloped so as to form a continuation of the outer side surface 80a of the point 76a. This results in a smooth enlargement or stretching of the circular opening which is initially formed in the skin 132a by the point 76a of the shaft 24a. As the shaft 24a and anchor 30a continue to move downward (as viewed in FIG. 6) into the flesh 134a beneath the skin 132a, the point 76a on the shaft 24a pierces the body tissue to facilitate movement of the anchor 30a into the body tissue.

Once the anchor 30a has been moved to the desired depth in the body tissue, the anchor is separated from the shaft 24a. This may be done by merely withdrawing the leading end section 144 of the shaft 24a from the anchor 30a while the anchor remains in the orientation shown in FIG. 6 in the body tissue 88a. It is contemplated that there will be relatively little friction between the outer side surface 120a on the positioning portion 146 of the shaft 24a and the inner side surface 52a. This enables the anchor to be held in position in the body tissue 88a by the resilient force applied against the anchor 30a by the body tissue as the inserter 20a is withdrawn from the anchor.

It is contemplated that it may be desired to apply force against the trailing end surface 42a of the anchor 30a to facilitate separation of the shaft 24a from the anchor 30a. If this is the case, a cylindrical pusher rod 150 (FIG. 7) may be provided in a suitable passage formed in the solid shaft 24a. An actuator 110a has a knob 112a which is connected with the pusher rod 150 and is movable along a slot 114a formed in the handle 22a.

When the shaft 24a is to be withdrawn from the anchor 30a, the actuator knob 112a is moved downward. This results in the pusher rod 150 moving downward (as viewed in FIG. 7) relative to the shaft 24a. A circular leading end surface on the pusher rod 150 applies force against the trailing end surface 42a of the anchor to facilitate separation of the shaft from the anchor. It should be understood that the pusher rod 150 is optional and may be omitted if desired.

It is believed that in certain situations at least, it will be desired to change the orientation of the anchor relative to the body tissue 88a and the shaft 24a as the shaft 24a and anchor 30a are separated. To accomplish this, the leg 62a of the suture 32a is tensioned, in the manner indicated by the arrow 84a in FIG. 9 as the shaft 24a is withdrawn from the anchor. This results in pivoting movement of the anchor relative to the shaft 24a in the same manner as previously explained in conjunction with the embodiment of the invention illustrated in FIGS. 1–5.

It is believed that the use of the pusher rod 150 to apply force against a side of the anchor 30a opposite from the suture 32a will promote pivoting movement of the anchor. In addition, pivoting movement of the anchor 30a is promoted by engagement of the outer side surface 80a on the point 76a of the shaft 24a with the inner side surface 52a of the anchor. It should be understood that the anchor 30a moves through the orientation shown in FIG. 9 to the orientation shown in FIG. 5 for the anchor 30.

It is contemplated that the point 76a may have a configuration which is different than the illustrated conical configuration. For example, the point 76a could be formed by a single flat side surface which is skewed relative to a central axis of the shaft 24 or by a plurality of skewed flat side surfaces which intersect at the central axis of the shaft. Alternatively, the end of the end section could have a blunt or flat configuration rather than the illustrated pointed configuration.

Third Embodiment of Inserter

In the embodiments of the inserter illustrated in FIGS. 1–9, the anchor is retained on the shaft of the inserter prior to insertion of the anchor into body tissue. In the embodiment of the invention illustrated in FIG. 10, the inserter includes a spring which is utilized to retain the anchor on the shaft of the inserter. Since the embodiment of the invention illustrated in FIG. 10 is generally similar to the embodiments of the invention illustrated in FIGS. 1–9, similar numerals will be utilized to designate similar components, the suffix letter "b" being associated with the numerals of FIG. 10 to avoid confusion.

An inserter 20b (FIG. 10) includes a handle (not shown) and a shaft 24b which extends outward from the handle. The shaft 24b is integrally formed from a single piece of metal, that is, stainless steel. The shaft 24b includes a relatively large diameter main section 142b and a relatively small diameter leading end section 144b. The leading end section 144b includes a positioning portion 146b on which a conical point 76b is disposed in a coaxial relationship with the main section 142b of the shaft 24b. An annular pusher surface 98b is formed at the junction between the main section 142b and positioning portion 146b of the shaft 24b.

In the illustrated embodiment of an anchor 32b the anchor is a suture anchor. A suture 32b has an outer leg 62b which extends along the outside of the anchor 30b. In addition, the suture 32b has an inner leg 64b which extends through a passage 28b in the anchor 30b. The leading end section 144b and the inner leg 62b of the suture 32b both extend through the passage 28b in the anchor 30b.

In accordance with a feature of this embodiment of the invention, a spring 160 extends through a passage in the shaft 24b. The illustrated spring 160 is formed of metal wire. However, the spring 160 could be a leaf spring formed of sheet metal if desired.

An upper end portion (not shown) of the wire spring 160 is connected with an actuator knob, corresponding to the actuator knobs 112 and 112a of the embodiments of the invention illustrated in FIGS. 1–9. The spring 160 has a bent portion 164 which engages an inner side surface 52b of the anchor 30b.

After the anchor 30b has been inserted into body tissue, in the manner described in conjunction with the embodiment of the invention illustrated in FIGS. 1–9, the spring 160 is axially tensioned. To axially tension the spring 160, the actuator knob is moved away from the leading end section 144b of the shaft 24b. The axial tension causes the bent portion 164 of the spring 160 to straighten and move out of engagement with the inner side surface 52b of the passage 28b in the anchor 30b. The shaft 24b can then be withdrawn from the anchor 30b.

It is preferred to move the bent portion 164 of the spring 160 out of engagement with the inner side surface 52b of the anchor 30b by resiliently flexing the spring. However, the tension force applied to the spring 160 may only effect a reduction in the force applied by the spring against the inner side surface 52b of the anchor 30b.

In the embodiment of the invention illustrated in FIG. 10, the anchor 30b and one-piece shaft 24b are separated by merely withdrawing the shaft from the anchor after it has been positioned in a desired location in body tissue. However, a pusher member, corresponding to the pusher rod 150 of the embodiment of the invention illustrated in FIGS. 6–9 could be utilized to promote separation of the anchor 30b from the shaft 24b if desired. Alternatively, the shaft 24b could be formed by two relatively movable members, corresponding to the inner and outer members 92 and 94 of the embodiment of the invention illustrated in FIGS. 1–5. Of course, the orientation of the anchor 30b can be changed relative to the shaft 24b by tensioning the leg 64b of the suture 32b as the point 76b of the shaft 24b moves to a location adjacent to the trailing end surface 42b of the anchor.

Inserter—Fourth Embodiment

In the embodiments of the invention illustrated in FIGS. 1–10, the outer member 94 moves relative to the inner member 92 during positioning of an anchor relative to body tissue. In the embodiment of the invention illustrated in FIGS. 11–15, the inner member may move relative to the outer member. Since the embodiment of the invention illustrated in FIGS. 11–15 is generally similar to the embodiments of the invention illustrated in FIGS. 1–10, similar numerals will be utilized to identify similar components, the suffix letter "c" being added to the numerals of FIGS. 11–15 to avoid confusion.

An anchor inserter apparatus 20c, constructed in accordance with the present invention, is illustrated in FIG. 11 and is used to position an anchor 30c relative to body tissue. The illustrated anchor 30a is a suture anchor. The apparatus 20c includes a tubular outer member 94c. The tubular outer member 94c has a cylindrical tubular body 200 and a handle 22c which are integrally formed as one piece.

An inner member 92c is disposed in a passage 204 which is formed in the tubular outer member 94c. The cylindrical passage 204 extends between a circular entrance opening 206 and a circular exit opening 208 formed in the tubular outer member 94c. The inner member 92c includes a cylindrical body 212. A circular handle 214 is integrally formed as one piece with the cylindrical body 212 of the inner member 92c. The inner member 92c has an axially tapered leading end portion 218 with a surface which applies force against a trailing end portion 48c of the suture anchor 30c.

The apparatus 20c is illustrated in FIG. 11 in a fully assembled condition prior to use of the apparatus to position the anchor 30c in either hard or soft body tissue. At this time, the trailing end portion 38c of the suture anchor 30c is disposed in the passage 204 in the tubular outer member 94c. A leading end portion 44c of the suture anchor 30c extends outward from the tubular member 94c.

In accordance with a feature of this embodiment of the invention, a slot 102c (FIGS. 11 and 12) extends between the entrance opening 206 (FIG. 11) to the cylindrical passage 204 and the exit opening 208 from the passage. The slot 102c extends through the handle 22c. The slot 102c is defined by a pair of flat parallel linear side surfaces 224 and 226 (FIGS. 11 and 12). The side surfaces 224 and 226 extend between a cylindrical outer side surface 228 (FIG. 12) on the tubular outer member 94c and a cylindrical inner side surface 230 (FIG. 12) of the passage 204 in the tubular outer member.

When the inserter 20c is used with a suture anchor, the slot 102c facilitates positioning of the anchor 30c in the passage 204 during assembly of the suture anchor inserter apparatus 20c (FIG. 11). This is because outer and inner legs 62c and 64c of the suture 32c can be readily positioned in the slot 102c during assembly of the anchor inserter apparatus 20c. The slot 102c has a straight longitudinal central axis which extends parallel to the longitudinal central axis of the passage 204 and to a longitudinal central axis of the cylindrical body 212 of the inner member 92c. The legs 62c and 64c of the suture 32c extend between axially opposite ends of the slot 102c. The slot 102c encloses the suture 32c and protects the legs 62c and 64c against being snagged by objects in the environment around the suture anchor inserter apparatus 20c.

When the anchor inserter apparatus 20c is to be assembled and used with a suture anchor, the suture 32c (FIG. 11) is inserted through a pair of passages 236 and 238 in the suture anchor 30c. The passages 236 and 238 extend diametrically through the suture anchor 30c which, except for the passages 236 and 238, is a solid piece of material. A connector section 66c (FIG. 13) of the suture extends between the passages 236 and 238. Although the illustrated anchor 30c is formed from a solid cylindrical piece of stainless steel, the anchor 30c could be formed of any one of many different materials and have any one of many different configurations, in the manner previously explained in conjunction with the embodiment of the invention illustrated in FIGS. 1–5.

Once the suture 32c (FIG. 11) has been threaded through the passages 236 and 238 in the suture anchor 30c, the suture anchor is moved through the entrance opening 206 into the passage 204. The cylindrical body 212 of the inner member 92c is then moved through the entrance opening 206 into the passage 204. The leading end portion 218 of the inner member 92c moves into engagement with the trailing end portion 38c of the anchor 30c. The inner member 92c is then used to push the anchor 30c along the passage 204. Of course, if the anchor 30c is not utilized to anchor the suture 32c, the suture would be omitted.

In the illustrated embodiment of the invention, the tubular outer member 94c is constructed with a passage 204 having an inside diameter which is less than the outside diameter of the anchor 30c. This results in interference or drag between the anchor 30c and the inner side surface 230 of the passage 204 in the tubular outer member 94c.

The slot 102c (FIG. 11) in the tubular outer member 94c facilitates resilient flexing of the tubular outer member under the influence of force applied against the inner side surface 230 of the passage 204 by the anchor 30c. The cylindrical body 212 of the inner member 92c has an outside diameter which is less than the inside diameter of the passage 204. Therefore, there is no interference between the inner member 92c and the outer member 94c as the inner member 92c is inserted into the passage 204. Of course, interference could be provided between the outer side surface on the body 212 of the inner member 92c and the inner side surface 230 of the passage 204 if desired.

As the anchor 30c moves along the passage 204 under the influence of force applied against the anchor by the inner member 92c, the outer member 94c is resiliently flexed and the width of the slot 102c increases to accommodate the interference between the anchor 30c and the inner side surface 230 of the passage 204. It should be understood that there is only a small amount interference between the anchor 30c and the inner side surface 230 of the passage 204 in the tubular outer member so that the inner member 92c can, with a relatively moderate amount of force, move the anchor 30c along the passage 204.

The anchor 30c is moved along the passage 204 to a position in which the trailing end portion of the anchor 30c is disposed in the passage and the leading end portion 44c of the suture anchor extends outward from the tubular outer member 94c (FIG. 11). When the anchor 30c moves to this position, the application of force to the inner member 92c is interrupted. The interference between the outer side surface of the anchor 30c and the inner side surface 230 of the passage 204 results in the tubular outer member 94c gripping the outer side surface of the suture anchor 30c. This gripping action enables the tubular outer member 94c to hold the anchor 30c against movement relative to the tubular outer member. This results in the anchor 30c being maintained in the position shown in FIG. 11 during handling of the anchor inserter apparatus 20c.

Once the anchor 30c has been moved to the position shown in FIG. 11, the outer and inner legs 62c and 64c of the suture 32c are moved into the slot 102c and tensioned. The taut suture legs 62c and 64c are straight and have longitudinal central axes extending parallel to the longitudinal central axis of the slot 102c and the passage 204 in the tubular outer member 94c. The legs 62c and 64c of the suture 32c extend through opposite ends of the slot 102c. The suture legs 62c and 64c extend through the portion of the slot 102c disposed in the handle 22c. A suitable retainer, such as adhesive tape, may be utilized to secure the legs 62c and 64c to the cylindrical body 312 of the inner member 92c and to retain the suture legs 62c and 64c in the slot 102c. The resiliently deflected body 200 of the tubular outer member 94c presses the cylindrical inner side surface 230 of the tubular outer member against the cylindrical outer side surface 50c of the trailing end portion 38c of the anchor 30c to hold the anchor in place.

After the apparatus 20c has been assembled, in the manner previously explained, the apparatus is transported from a remote assembly location to an operating room or other location where the apparatus is to be used to position the anchor 30c in body tissue. The manner in which the suture anchor inserter apparatus 20c is used to position the anchor 30c in a recess or opening 250 formed in bone 252 is illustrated schematically in FIGS. 13–15. The bone 252 includes a hard outer layer 254 and soft cancellous inner bone 256.

When the anchor 30c is to be positioned in the bone 252, the leading end portion 44c (FIG. 11) of the anchor 30c is inserted into the recess or opening 250. Since the leading end portion 44c of the anchor 30c extends outward from the tubular outer member 94c, aligning of the anchor 30c with the opening 254 in the bone 252 is facilitated. In addition, the presence of the slot 102c enables a surgeon to visualize the position of the leading end portion 44c of the anchor 30c relative to the outer layer 254 of the bone 252 as the leading end portion 44c of the anchor 30c is inserted into the recess or opening 250 (FIGS. 11 and 13). During initial positioning of the anchor 30c in the opening 250 in the bone 252, the tubular outer member 94c grips the anchor and holds the anchor against movement relative to the tubular outer member.

Once the leading end portion 44c of the anchor 30c has been positioned in the opening 250, in the manner illustrated schematically in FIG. 13, the tubular outer member 94c and inner member 92c are moved relative to each other to move the anchor 30c further into the opening 250. Thus, the inner member 92c is moved downward (as viewed in FIG. 13) to push the trailing end portion 38c (FIG. 11) of the anchor 30c out of the passage 204 in the tubular outer member 94c. As this occurs, the leading end portion 218 of the inner member 92c moves out of the tubular outer member 94c into the opening 250 (FIGS. 13 and 14).

When the anchor 30c is a suture anchor, the legs 62c and 64c of the suture 32c are tensioned to pivot or toggle the anchor relative to the leading end portion 218 of the inner member 92c. This results in the anchor 30c moving from an orientation in which a longitudinal central axis of the anchor 30c is aligned with the longitudinal central axis of the tubular outer member 94c (FIG. 13) to a position in which the longitudinal central axis of the anchor 30c extends transverse to the longitudinal central axis of the tubular outer member 94c. The leading end portion 318 of the inner member 92c is tapered to promote the pivotal movement of the anchor 30c in a manner similar to that disclosed in U.S. Pat. No. 5,403,348 issued Apr. 4, 1995 to Peter M. Bonutti and entitled "Suture Anchor". However, as was previously mentioned, the anchor 30c could remain in its initial orientation.

Once the anchor 30c has been pivoted to the desired orientation relative to the bone 252, the inserter apparatus 20c is withdrawn from the recess 250 and disengaged from the legs 62c and 64c of the suture 32c. Disengagement of the anchor inserter apparatus 20c from the suture 32c is facilitated by the slot 102c (FIG. 11) in the tubular outer member 94c. Thus, when the anchor inserter apparatus 20c is to be disengaged from the suture 32c, it is merely necessary move the anchor inserter apparatus 20c sidewardly away from the legs 62c and 64c of the suture 32c or to pull the legs of the suture sidewardly away from the anchor inserter apparatus 20c.

Once the tubular outer member 94c and inner member 92c have been disengaged from the suture 32c, the anchor inserter apparatus 20 is sterilized. A suture anchor 30c is then loaded into the anchor inserter apparatus 20c and suture anchor inserter apparatus reused. The slot 102c facilitates reloading of the anchor inserter apparatus 20c.

Although the anchor inserter apparatus 20c may be initially loaded or reloaded with a second anchor 30c in the manner previously explained, it is believed that it may be preferred to load the anchor inserter apparatus 20c by merely moving the trailing end portion 38c of anchor 30c through the exit opening 208 in the leading end portion 242 of the tubular outer member 94c while the tubular inner member 92c is withdrawn. The trailing end portion 38c of the anchor 30c can be manually inserted through the opening 208 in the leading end portion 242 of the tubular outer member 94c. The trailing end portion 38c of the anchor 30c is rounded or chamfered to facilitate moving the trailing end portion 38c of the anchor 30c into the passage 204 in the tubular outer member 94c.

As an anchor 30c is manually moved into the leading end portion 242 of the tubular outer member 94c, the trailing end portion 38c of the anchor 30c applies force against the exit opening 208 to resiliently deflect and expand the body 200 of the tubular outer member 94c. As the body 200 of the tubular outer member 94c is resiliently expanded, the width of the portion of the slot disposed in the leading end portion 242 of the tubular outer member 94c is increased. This results in the inner side surface 230 of the passage 204 in the tubular outer member 94c firmly gripping the trailing end portion 38c of the anchor 30c as the anchor is moved through the opening 208.

The tubular outer member 94c and inner member 92c may be formed of any desired material. For example, it is contemplated that the tubular outer member 94c and handle 22c could be fabricated from a single piece of metal sheet material. The inner member 92c and handle 214 could be fabricated from a metal rod. Alternatively, the tubular outer member 94c and handle 22c could be integrally molded as one piece of polymeric material. Similarly, the inner member 92c and handle 214 could be molded of a suitable polymeric material.

In the foregoing description of the manner in which the anchor 30c is positioned relative to the bone 252, the anchor is moved out of the passage 204 in the tubular outer member 94c by moving the inner member 92c relative to the outer member 94c. However, it is contemplated that the anchor 30c could be separated from the tubular outer member 94c by moving the tubular outer member relative to the inner member 92c. Thus, the inner member 92c could be maintained stationary and the outer member 94c moved relative to the inner member. Although FIGS. 13–15 illustrate positioning the anchor 30c relative to the bone 252, the anchor inserter apparatus 20c could be used to position the anchor relative to soft body tissue.

In the embodiment of the invention illustrated in FIG. 11, the tubular outer member 94c has a relatively simple flange-type handle 22c and the inner member 92c has a relatively simple handle 214. It is contemplated that the tubular outer member 94c and the inner member 92c could be provided with handles which are formed separately from the tubular outer member and the inner member. For example, the inner member 214 could be provided with a handle similar to the handle provided for the embodiment of the invention illustrated in FIG. 1.

Retainer

In the embodiment of the invention illustrated in FIGS. 11–15, the anchor 30c is a suture anchor and the legs 62c and 64c of the suture 32c are positioned in the open slot 102c of the suture anchor inserter apparatus 20c. In the embodiment of the invention illustrated in FIGS. 16–18, a retainer member is provided in association with the anchor inserter apparatus 20c to hold the legs of the suture in the slot when the anchor is used with a suture. Since the embodiment of the invention illustrated in FIGS. 16–18 has a construction which is similar to the construction of the embodiment of the invention illustrated in FIGS. 11–15, similar numerals will be utilized to designate similar components, the suffix letter "d" being associated with the numerals of FIGS. 16–18 to avoid confusion.

The suture anchor inserter apparatus 20d (FIG. 16) includes a tubular outer member 94d having a cylindrical passage 204d. A cylindrical inner member 92d extends into the passage 204d in the outer member 94d. A straight slot 102d is formed in the tubular outer member 94d and extends between opposite ends of the tubular outer member 94d. The slot 102d forms a passage through a handle 22d which is integrally formed as one piece with the tubular outer member 94d.

In accordance with a feature of this embodiment of the invention, a suture retainer sleeve 270 is rotatably mounted on the tubular outer member 94d. The suture retainer sleeve 370 has a generally cylindrical configuration. A slot 272 extends between axially opposite ends of the suture retainer sleeve 270. The suture retainer sleeve 270 spans the slot 102d (FIGS. 16 and 17) to retain the legs 62d and 64d of the suture 32d in the slot. Thus, the sleeve 270 holds the suture legs 62d and 64d in the slot 102d with the suture legs extending between opposite ends of the slot.

When the anchor inserter apparatus 20d is being assembled, the retainer sleeve 270 is rotated in a counterclockwise direction (as viewed in FIG. 17) relative to the tubular outer member 94d to move the slot 272 in the retainer sleeve 270 into alignment with the slot 102d of the tubular outer member 94. This enables the legs 62d and 64d of the suture 42d to be positioned in the slot 102d in the tubular outer member 94d. Once the legs 62d and 64d have been positioned in the slot 102d in the tubular outer member 94d, in the manner illustrated in FIG. 18, the suture retainer sleeve 270 is rotated in a clockwise direction to again span the slot 102d and block movement of the legs 62d and 64d of the suture 30d out of the slot (FIG. 17).

In the embodiment of the invention illustrated in FIGS. 16–18, a cylindrical suture retainer sleeve or ring 270 is rotatably mounted on the tubular outer member 94d and is movable between a closed position blocking the slot 102d and an open position providing access to the slot 102d. However, it is contemplated that any desired type of member could be mounted on the tubular outer member 94d to block the slot 102d and retain the suture 32d in the slot. In the embodiment of the invention illustrated in FIGS. 16–18, the suture retainer sleeve 270 extends along only a portion of the length of the tubular outer member 94d. If desired, the suture retainer sleeve 270 could have a substantially greater axial extent so as to span a greater axial length of the slot 102d when the suture retainer sleeve 270 is in the closed position illustrated in FIG. 17.

The suture retainer sleeve 270 has been illustrated in FIG. 16 as being mounted on a suture anchor inserter apparatus 20d having the same construction as the anchor inserter apparatus 20c of FIGS. 11–15. However, the suture retainer sleeve 270 could be utilized in conjunction with the embodiment of the invention illustrated in FIGS. 1–5 if desired. If this was done, the suture retainer sleeve 270 would be mounted on the outer member 94.

Anchor Retainer

Figure 19:
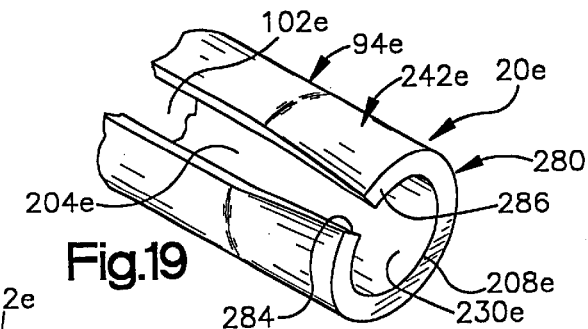
FIG. 19 is a fragmentary schematic illustration of an end portion of a tubular outer member of another embodiment of the apparatus illustrated in FIG. 11 and in which the end portion of the tubular outer member is contracted.
Figure 20:
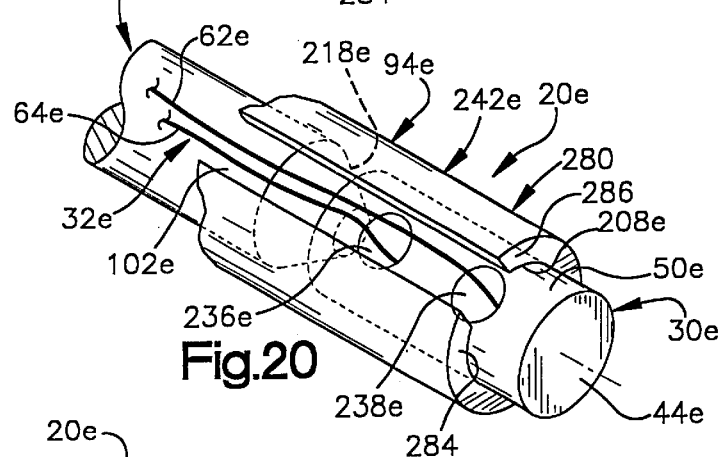
FIG. 20 is a fragmentary schematic illustration, generally similar to FIG. 19, illustrating the relationship between the end portion of the tubular outer member, an anchor, and an inner member after the end portion of the tubular outer member has been expanded and is effective to grip an outer side surface of the anchor.
Figure 21:
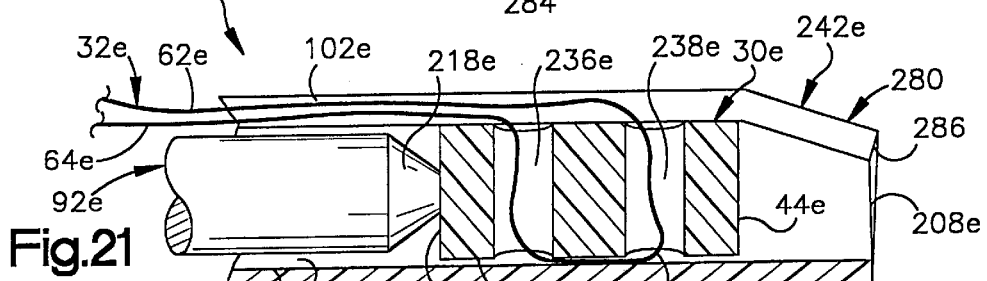
FIG. 21 is a schematic sectional view depicting the manner in which a leading end of the anchor of FIG. 20 is moved into engagement with the contracted end portion of the tubular outer member of FIG. 19.

In the embodiments of the invention illustrated in FIGS. 11–18, the anchor 30c is held against movement relative to the tubular outer member 94c due to interference between the suture anchor 30c and the inner side surface 230 of the passage 204 in the tubular outer member 94c. In the embodiment of the invention illustrated in FIGS. 19–22, there is no interference between the anchor and the inner side surface of the tubular outer member throughout a major portion of the length of the tubular member. The leading end portion 242 (FIG. 11) of the tubular outer member 94c is provided with a retainer which is effective to hold the anchor against movement. Since the embodiment of the invention illustrated in FIGS. 19–21 is generally similar to the embodiments of the invention illustrated in FIGS. 1–18, similar numerals will be utilized to designate similar components, the suffix letter "e" being associated with the numerals of FIGS. 20–22 to avoid confusion.

The anchor inserter apparatus 20e has the same general construction as the anchor inserter apparatus 20c of FIG. 11. The anchor inserter apparatus 20e (FIG. 19) includes a tubular outer member 94e having a slot 102e. The slot 102e extends between openings at axially opposite ends of the tubular outer member 94c. Thus, the slot 102e extends to an exit opening 208e in the leading end portion 242e of the tubular outer member 94e.

An inner member 92e (FIGS. 20–22) is telescopically received in a passage 204e (FIGS. 21 and 22) in the tubular outer member 94e. The cylindrical inner member 92e has a diameter which is less than the diameter of the passage 204e in the tubular outer member 94e. The inner member 92e has a leading end portion 218e (FIGS. 20–22) which is engageable with a suture anchor 30e.

The anchor 30e (FIG. 20) is a suture anchor and has a pair of parallel passages 236e and 238e which extend diametrically through the anchor 30e. A suture 32e extends through the cylindrical passages 236e and 238e in the suture anchor 30e. Thus, the suture 32e has an outer leg 62e which extends through the passage 238e in the suture anchor 30e. Similarly, the suture 32e has an inner leg 64e which extends through the passage 236e in the suture anchor 30e. A connector section 66e (FIGS. 21 and 22) of the suture 32e extends along an outer side surface of the suture anchor 30e and interconnects the two legs 62e and 64e. The suture 32e may be omitted if desired.

In accordance with a feature of this embodiment of the invention, an anchor retainer or positioner 280 is provided in the leading end portion 242e of the tubular outer member 94e to hold the anchor 30e in a desired position relative to the tubular outer member. In the embodiment of the invention illustrated in FIGS. 19–22, the anchor retainer 280 is resiliently deflectable under the influence of force applied against the anchor retainer by a leading end portion 44e of the suture anchor 30e. The anchor retainer 280 then grips a cylindrical outer side surface 50e of the anchor 30e to hold the anchor against movement relative to the tubular outer member 94e. The anchor 30e may be a suture anchor The tubular outer member 94e is initially formed so that the inner side surface 230e (FIG. 19) of the passage 204e tapers axially outward and radially inward from a relatively large diameter upstream or ahead of the leading end portion 242 of the tubular outer member to a relatively small size at the axially outer end of the tubular outer member 94e. Thus, the passage 204e in the tubular outer member 94e tapers axially toward the right (as viewed in FIG. 19) to the exit opening 208e. The exit opening 208e has a generally oval configuration formed by radially inwardly projecting end portions 284 and 286 of the tubular outer member 94e.

The passage 204e in the tubular outer member 94e has a circular cross sectional configuration, as viewed in a plane extending perpendicular to the longitudinal central axis of the passage, throughout the length of the passage ahead of the leading end portion 242e of the tubular outer member 94e. This portion of the passage 204e has a diameter which is slightly larger than the diameter of the suture anchor 30e. At the leading end portion 242e of the tubular outer member 94e, the passage 240e tapers inwardly (FIG. 21) to the opening 208e. The opening 208e has a cross sectional area, as viewed in a plane extending perpendicular to a longitudinal central axis of the passage 204e, which is smaller than the cross sectional area of the portion of the passage 204e ahead of the leading end portion 242e of the tubular outer member 94e and smaller than the cross sectional area of the anchor 30e.

The slot 102e in the tubular outer member 94e (FIG. 19) has a uniform width throughout the length of the slot ahead of the leading end portion 242e of the tubular outer member 94e. At the leading end portion 242e of the tubular outer member 94e, the width of the slot 102e decreases as the passage 240e tapers inwardly to the opening 208e. At the opening 208e, the slot 102e has a width which is smaller than the width of the slot 102e ahead of the leading end portion of the tubular outer member 94e.

Upon movement of the anchor 30e through the leading end portion 242e of the tubular outer member 94e, the leading end portion 50e of the anchor 30e applies force against the outer end portion 242e of the tubular outer member 94e to resiliently deflect the end portions 284 and 286 of the tubular member 94e radially outward. This results in the tubular outer member 94e being resiliently expanded so that the passage 204e is substantially the same size throughout the length of the passage. As the leading end portion 242e of the tubular outer member 94e is resiliently expanded, the width of the portion of the slot 102e in the leading end portion of the tubular outer member increases. This results in the slot 102e having a substantially uniform width throughout its length.

During assembly of the anchor inserter apparatus 20e, the anchor 30e is moved through an entrance opening, corresponding to the entrance opening 206 of FIG. 11, to the passage 204e. The cylindrical outer side surface 50e (FIG. 21) of the suture anchor 30e has a diameter which is less than the diameter of the passage 204e until the suture anchor moves to the leading end portion 242e of the tubular outer member 94e. Therefore, the anchor 30e can be readily moved along the passage 204e from an entrance opening to the radially inwardly tapering leading end portion 242e of the tubular member 94e under the influence of either gravity and/or force transmitted from the suture 32e to the anchor 30e.

When the leading end portion 44e of the anchor 30e encounters the inwardly tapering leading end portion 242e of the tubular outer member 94e (FIG. 21) continued movement of the anchor 30e toward the right (as viewed in FIG. 21) is impeded. The inner member 92e is then moved along the passage 204e until the axially tapered leading end portion 218e of the inner member engages a trailing end portion 38e of the anchor 30e. An axial force is then transmitted from the inner member 92e to the trailing end portion 38e of the anchor 30e. This force presses the leading end portion 44e of the anchor 30e against the inwardly sloping end portions 284 and 286 (FIG. 19) of the tubular outer member 94e at the axially tapering leading end portion of the passage 204e.

Figure 22:
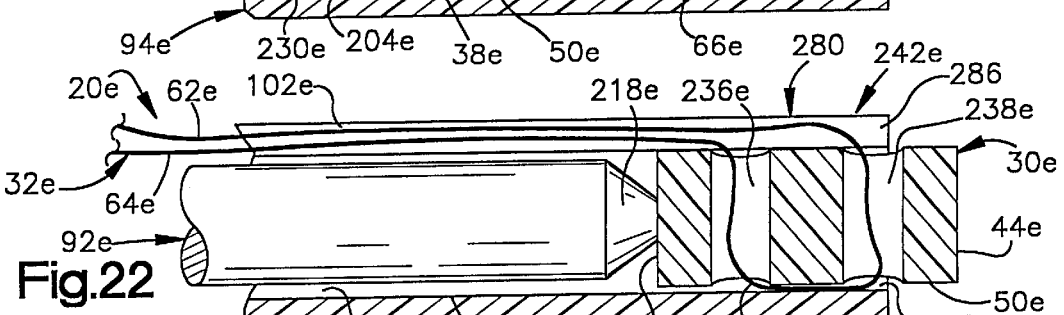
FIG. 22 is a schematic sectional view, generally similar to FIG. 21, depicting the manner in which the end portion of the tubular outer member of FIG. 19 is resiliently deflected outward by the anchor as the anchor moves to the position shown in FIG. 20.

The force applied against the inwardly projecting portions 284 and 286 of the tubular outer member 94e by the leading end portion 44e of the anchor 30e resiliently expands the tubular outer member 94e from the configuration illustrated in FIG. 21 to the configuration illustrated in FIG. 22. As this occurs, the axially tapering end portion of the passage 204e in the leading end portion 242e of the tubular outer member 94e is resiliently expanded to a cylindrical configuration (FIG. 22). Once this has occurred, the anchor 30e is gripped by the leading end portion 242e of the tubular outer member 94e.

The inner side surface 230e (FIG. 22) of the passage 204e through the tubular outer member 94e is pressed firmly against the cylindrical outer side surface 50e of the suture anchor 30e. This enables the retainer 280 to securely hold the suture anchor in the position shown in FIG. 22. At this time the trailing end portion 38e of the anchor 30e is disposed in the passage 204e and the leading end portion 44e of the anchor 30e extends outward from the tubular outer member 94e.

After the specific anchor 30e has been moved to the position shown in FIG. 22, the legs 62e and 64e of the suture 32e are tensioned and positioned in the slot 102e in the manner previously explained in conjunction with the embodiment of the invention illustrated in FIG. 11. The suture legs 62e and 64e extend through axially opposite end portions of the slot 102e. A retainer sleeve, corresponding to the retainer sleeve 270 of FIGS. 16–18, may be provided in association with the tubular outer member 94e of FIGS. 19–22 to retain the legs 62e and 64e of the suture 32e in the slot 102e in the manner previously explained in conjunction with the embodiment of the invention illustrated in FIGS. 16–18. Alternatively, a retainer, such as adhesive tape, could be used to hold the suture legs 62e and 64e in the slot 102e.

It should be understood that the tubular outer member 94e is provided with a handle, corresponding to the handle 22c of FIG. 11. The slot or passage 102e extends through the handle on the tubular outer member 94e in the same manner as previously described in conjunction with the embodiment of the invention illustrated in FIG. 11. The suture legs 62e and 64e extend through an open end of the slot 102e in the handle to enable a surgeon to manually engage the suture legs. A handle, corresponding to the handle 214 of FIG. 11, may be provided in association with the inner member 92e of FIGS. 20–22.

Once the anchor inserter apparatus 20e has been assembled, in the manner previously described, the suture anchor inserter apparatus is used to position the anchor 30e relative to body tissue. The anchor inserter apparatus 20e is used to position the anchor 30e relative to body tissue in the same manner previously explained in conjunction with the embodiment of the invention illustrated in FIGS. 11–15. Once the anchor 30e has been positioned relative to body tissue, the suture legs 62e and 64e are easily disengaged from the open slot 102e in the tubular outer member 94e.

In the embodiment of the invention illustrated in FIGS. 19–22, a single slot 102e extends throughout the axial length of the tubular outer member 94e to accommodate the legs 62e and 64e of the suture 32e. If desired, the tubular outer member 94e could be formed without the slot. If this was done, the outer end portion 242e of the tubular outer member 94e would still be axially tapered. In the absence of the slot 102e, the legs 62e and 64e of the suture 32e would be disposed in the passage 204e and would be enclosed by the tubular outer member 94e. However, the suture 32e could be omitted if desired.

It is believed that it will be preferred to provide the slot 102e in the tubular outer member 94e in order to facilitate positioning of the legs 62e and 64e of the suture 32e relative to the anchor inserter apparatus 20e during assembly of the apparatus when the anchor is a suture anchor. In addition, the slot 102e facilitates separating the anchor inserter apparatus 20e from the suture 32e after the suture anchor 30e has been positioned in body tissue in the manner previously explained. Of course, the anchor 30e could have any known construction.

In the embodiment of the invention illustrated in FIGS. 19–22, the slot 102e extends throughout the axial extent of the tubular outer member 94e. It is contemplated that one or more slots, which extend for a distance less than the axial extent of the tubular outer member 94e, could be provided in the tubular outer member. For example, three slots could be provided at equally spaced intervals about the circumference of the tubular outer member 94e. Each of these three slots may have a length which is approximately two to four times as great as the length of a suture anchor 30e. If a plurality of slots with a length which is less than the axial extent of the tubular outer member 94e are used, the portion of the tubular member between each of the slots may extend radially inward toward the central axis of the tubular outer member 94e and be resiliently deflected by engagement with the leading end portion 44e of the suture anchor 30e.

In the embodiment of the invention illustrated in FIGS. 19–22, the tubular outer member 94e is formed of metal and the anchor retainer 280 is formed by deflecting the edge portions 284 and 286 of the tubular outer member radially inward toward the central axis of the tubular outer member 94e. It should be understood that the extent of deflection of the edge portion 286 is exaggerated in FIG. 21 in order to provide a clear schematic illustration of the manner in which the edge portions 284 and 286 are deflected. It is contemplated that the extent of deflection of the edge portions 284 and 286 will be less than has been illustrated in FIG. 21.

If desired, the tubular outer member 94e could be molded as a single piece of polymeric material. If the tubular outer member 94e is molded as single piece of polymeric material, the inwardly extending edge portions 284 and 286 would be formed in the tubular outer member 94e as originally molded. The side wall of the tubular outer member 94e would have sufficient flexibility to enable the edge portions 284 and 286 to be resiliently deflected under the influence of force applied against them by the leading end portion 44e of the suture anchor 30e.

In the embodiment of the invention illustrated in FIGS. 19–22, the inner member 92e is moved toward the right (as viewed in FIGS. 21 and 22) relative to the tubular outer member 94e. The force transmitted from the inner member 92e to the anchor 30e presses the leading end portion 44e of the anchor against the deflected portions 284 and 286 of the tubular outer member 94e. This cams or forces the deflected portions 284 and 286 radially outward as the anchor 30e moves from the position shown in FIG. 21 to the position shown in FIG. 22. However, if desired, the tubular outer member 94e could be moved relative to the inner member 92e. Thus, the inner member 92e could be maintained stationary in the position shown in FIG. 21. The tubular outer member 94e would be moved toward the left (as viewed in FIG. 21) to effect relative movement between the inner and outer members 92e and 94e. As this relative movement occurs, the inwardly projecting edge portions 284 and 286 of the tubular outer member 94e would be cammed or forced radially outward. Relative movement between the inner member 92e and the tubular outer member 94e would be interrupted when the tubular outer member had moved to the position illustrated in FIG. 22 relative to the inner member.

Retainer Recess

In the embodiment of the invention illustrated in FIGS. 19–22, the tubular outer member 94e grips the cylindrical outer side surface 50e of the suture anchor 30e to hold the suture anchor in a desired position. In the embodiment of the invention illustrated in FIG. 23, the tubular outer member grips a recess formed in the suture anchor to hold the suture anchor in the desired position. Since the embodiment of the invention illustrated in FIG. 23 is generally similar to the embodiment of the invention illustrated in FIGS. 1–22, similar numerals will be utilized to designate similar components, the suffix letter "f" being associated with the numerals of FIG. 23 to avoid confusion.

Figure 23:
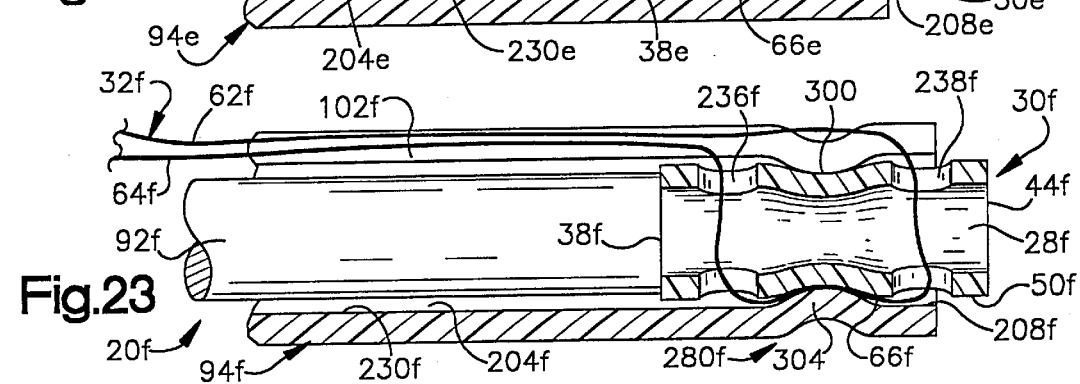
FIG. 23 is a schematic illustration, generally similar to FIG. 22, of a another embodiment of the invention, having the same general construction as the embodiment of FIG. 11, and illustrating the manner in which a projection on the end portion of a tubular outer member engages a recess in an anchor.

The anchor inserter apparatus 20f of FIG. 23 has the same general construction as the anchor inserter apparatus 20c of FIG. 11. The anchor inserter apparatus 20f (FIG. 23) includes a cylindrical tubular outer member 94f having a slot 102f. The straight slot 102f extends between openings at axially opposite ends of the tubular outer member 94f. Thus, the slot 102f extends to an exit opening 208f in the leading end portion of the tubular outer member 94f.

A cylindrical inner member 92f is telescopically received in a passage 204f in the tubular outer member 94f. The cylindrical inner member 94f has a diameter which is less than the diameter of the passage 204f in the tubular outer member 94f. The inner member 92f has a leading end portion which is engageable with the anchor 30f.

In the embodiment illustrated in FIG. 23, the anchor 30f has a tubular configuration. Thus, the anchor 30f has a longitudinally extending central passage 28f which extends between a trailing end portion 38f and a leading end portion 44f of the anchor 30f.

Although the anchor 30f could have many different constructions, the specific anchor illustrated in FIG. 23 is a suture anchor. Therefore, the anchor 30f is used with a suture 32f. The suture 32f has outer and inner legs 62f and 64f which extend through passages 236f and 238f which extend radially through the suture anchor 30f. The outer and inner legs 62f and 64f of the suture 30f are interconnected by a connector section 66f which extends along an outer side surface of the anchor 30f.

In accordance with a feature of this embodiment of the invention, the anchor 30f is provided with an annular recess or groove 300 (FIG. 23) which extends around the anchor 30f and has a central axis which is coincident with a longitudinal central axis of the suture anchor. The annular recess or groove 300 extends radially inward from a cylindrical outer side surface 50f of the anchor 30f. The recess or groove 300 is disposed midway between the radial passages 236f and 238f which extend through the anchor 30f. In the illustrated embodiment of the invention, the recess 380 has a gently curving configuration to avoid stress concentrations. However, the recess 300 could be more sharply defined if desired.

The tubular outer member 94f has an annular projection 304 which extends radially inward from an inner side surface 230f of the tubular outer member 94f. The slot 102f extends axially through the annular projection 304. The annular projection 304 has a central axis which is coincident with a longitudinal central axis of the tubular outer member 94f and extends parallel to a longitudinal central axis of the slot 102f. The portion of the passage 204f ahead of the annular projection 304 has a diameter which is larger than the diameter of the trailing and leading end portions 38f and 44f of the anchor 30f.

The annular projection 304 has an inside diameter which is less than the diameter of the trailing and leading end portions 38f and 44f of the anchor 30f. Prior to engagement with the anchor 30f, the annular projection 304 has an inside diameter which is slightly less than the outside diameter of the recess 300 in the suture anchor. This results in the annular projection 304 being deflected radially outward when the annular projection engages the recess 300 in the suture anchor 30f. Therefore, the annular projection 304 firmly grips the anchor 30f when the annular projection engages the recess 300 (FIG. 23).

When the annular projection 304 engages the recess 300, the trailing end portion 38f of the anchor 30f is disposed in a passage 204f in the tubular outer member 94f. The leading end portion 44f of the anchor 30f extends axially outward from the tubular outer member 94f. The distance which the anchor 30f extends outward from the tubular outer member 94f is determined by the location of the annular projection 304f relative to the axially outer end of the tubular outer member 94f and the location of the annular recess relative to the leading end portion 44f of the anchor 30f.

When the anchor 30f is to be moved to the position shown in FIG. 23, the anchor is positioned in the passage 204f and moved along the passage until the leading end portion 44f of anchor 30f engages the annular projection 304. The inner member 92f then applies force against the trailing end portion 38f of the anchor 30f to press the leading end portion 44f of the anchor against the annular projection 304. Force transmitted from the leading end portion 44f of the anchor 30f to the annular projection 304 causes the tubular outer member 94f to resiliently expand. This resilient expansion of the tubular member 94f increases the inside diameter of the annular projection 304.

As the anchor 30f continues to move toward the right (as viewed in FIG. 23), the annular projection 304 expands radially and moves into engagement with a cylindrical outer side surface 50f of the anchor 30f. At this time, the width of the slot 102f will have increased from an initial width to accommodate the radial expansion of the annular projection 304. Continued axial movement of the inner member 92f toward the right (as viewed in FIG. 23) moves the passage 238f through the anchor 30f past the annular projection 304. As this occurs, the annular projection 304 moves into engagement with the annular recess 300 in the suture anchor 30f.

The annular projection 304 resiliently grips the outer side surface of the suture anchor 30f. Sloping side surfaces on the projection 304 cooperate with sloping side surfaces on the recess 300 in the suture anchor 30f to cam or force the suture anchor to a position in which the annular projection is centered in the annular recess in the suture anchor 30f. As this occurs, the width of the slot 102f decreases. The rightward (as viewed in FIG. 23) force applied by the inner member 92f against the anchor 30f is interrupted when the anchor 30f has moved to the position shown in FIG. 23. At this time, the end portion 280f of the tubular outer member 94f is resiliently expanded and the slot 102f has a width which is greater than its undeflected width.

In the embodiment of the invention illustrated in FIG. 23, both the recess 300 and projection 304 have an annular configuration. Therefore, the annular projection will engage the annular recess even if the anchor 30*f* is rotated about its longitudinal central axis to a position offset from the position shown in FIG. 23. However, if desired, the recess 300 could extend for a distance less than the entire circumference of the suture anchor 30*f* and the projection 304 could extend for a distance which is less than the entire circumference of the tubular outer member 94*f*. For example, the recess 300 and the projection 304 could have a generally circular conical configuration if desired.

In the foregoing description, it has been assumed that the inner member 92*f* is moved axially relative to the outer member 94*f* to move the suture anchor 30*f* to the position shown in FIG. 23. However, if desired, the tubular outer member 94*f* could be moved relative to the inner member 92*f*. Thus, the tubular outer member 94*f* could be moved toward the left (as viewed in FIG. 23) relative to the inner member 92*f* to effect engagement of the annular recess 300 on the anchor 30*f* with the annular projection 304 on the tubular outer member 94*f*.

In addition, the foregoing description has assumed that the anchor 30*f* will be moved from the left toward the right relative to the tubular outer member 94*f* in order to engage the annular projection 304. This assumes that the anchor 30*f* will be inserted into the passage 204*f* at an opening, corresponding to the opening 206 of FIG. 11, adjacent to a handle, corresponding to the handle 22*c* of FIG. 11. However, if desired, the anchor 30*f* could be inserted into the passage 204*f* through the exit opening 208*f* in the tubular outer member 94*f*.

If the anchor 30*f* is inserted into the passage 94*f* through the exit opening 208*f*, the trailing end portion 38*f* of the anchor 30*f* would be moved through the opening 208*f* into engagement with the annular projection 304. An axially directed force would then be applied to the leading end portion 44*f* of the anchor 30*f*. This force would press the trailing end portion 38*f* of the anchor 30*f* against the annular projection 304. Force transmitted from the trailing end portion 38*f* of the anchor 30*f* would cause the annular projection 304 to expand with a resulting expansion of the slot 102*f*. As this occurs, the projection 304 would move into engagement with the outer side surface 50*f* of the anchor 30*f* adjacent to the trailing end portion 38*f* of the anchor.

The continued application of a leftward (as viewed in FIG. 23) force to the leading end portion of the anchor 30*f* would move the trailing end portion 38*f* of the suture anchor further into the passage 204*f*. As this occurs, the annular projection 304 on the tubular outer member 94*f* would move into engagement with the annular recess 300 in the anchor 30*f*.

It is believed that the foregoing front end loading, that is movement of the anchor 30*f* into the passage 204*f* through the exit opening 208*f*, may be preferred during assembly of the apparatus 20*f*. This is because the anchor 30*f* and tubular outer member 94*f* are moved through a relatively short distance relative to each other to enable the annular projection 304 to engage the recess 300 in the anchor 30*f*.

When the anchor 30*f* is to be positioned in body tissue, the leading end portion 44*f* of the anchor is inserted into the body tissue. Since the leading end portion 44*f* of the anchor 30*f* extends outward from the tubular outer member 94*f*, locating the anchor in a desired position relative to body tissue is facilitated. In addition, the slot 102*f* enables a surgeon to more easily visualize the position of the anchor 30*f* relative to the body tissue. During initial positioning of the anchor 30*f* relative to body tissue, the projection 304 grips the recess 300 to hold the anchor 30*f* against movement relative to the tubular outer member 94*f*. If desired, the suture 32*f* could be omitted.

Once the leading end portion 44*f* of the anchor 30*f* has been initially positioned relative to the body tissue by movement of the tubular outer member 94*f*, the tubular outer member and inner member 92*f* are moved relative to each other to move the anchor 30*f* to a desired depth in the body tissue. Thus, the inner member 92*f* is moved relative to the outer member 94*f* to apply force against the trailing end portion 38*f* of the anchor 30*f*. This force is effective to resiliently expand the annular projection 304 and slot 102*f* and move the anchor 30*f* out of engagement with the annular projection and into body tissue. Alternatively, the inner member 92*f* could be maintained stationary and the outer member 94*f* moved relative to the inner member to move the anchor 30*f* into the body tissue.

Once the anchor 30*f* has been separated from the tubular outer member 94*f* and moved to a desired depth in the body tissue, the orientation of the anchor may or may not be changed relative to the body tissue. When the anchor 30*f* is associated with the suture 32*f*, the legs 62*f* and 64*f* of the suture are tensioned to pivot the anchor. This results in the anchor moving from an orientation in which a longitudinal central axis of the anchor is aligned with a longitudinal central axis of the tubular outer member 94*f* to an orientation in which the longitudinal central axis of the anchor extends transverse to the longitudinal central axis of the tubular outer member 92*f*. The manner in which this is accomplished is the same as is disclosed in the aforementioned U.S. Pat. No. 5,403,348.

After the anchor 30*f* has been positioned relative to body tissue, the suture 32*f* is disengaged from the slot 102*f* in the tubular outer member 94*f* and handle (not shown). This is easily accomplished by moving the suture legs sideways out of the open slot 102*f*.

In the embodiment of the invention illustrated in FIG. 23, the slot 102*f* extends between axially opposite ends of the tubular outer member 94*f*. If desired, one or more slots which extend only part way along the length of the tubular outer member 94*f* could be provided. For example, three or four slots which extend from the exit opening 208*f* a short distance past the annular projection 304 could be provided in the tubular outer member 94*f*. These slots would enable the annular projection 304 to flex radially outward during relative movement between the suture anchor 30*f* and the annular projection 304. It is also contemplated that the annular projection 304 could be constructed so as to be radially flexible without the provision of slots in the tubular outer member 94*f*.

In the embodiment of the invention illustrated in FIG. 23, the annular projection 304 is integrally formed as one piece with the tubular outer member 94*f*. It is contemplated that the annular projection 304 could be formed separately from the tubular outer member 94*f*. For example, the annular projection 304 could be replaced by a resiliently expandable annular ring mounted in the passage 204*f* in the tubular outer member 94*f*. Alternatively, a resilient annular ring could be mounted on the outside of the tubular outer member 94*f* and extend through chordal slots formed in the tubular outer member into the passage 204*f* to engage the recess 300 in the anchor 30*f*.

Anchor Retainer

In the embodiment of the invention illustrated in FIG. 23, the anchor retainer 280*f* engages a recess 300 in the suture anchor 30f. In the embodiment of the invention illustrated in FIGS. 24 and 25, an anchor retainer engages a passage in the anchor. A suture may extend through the passage. Since the embodiment of the invention illustrated in FIGS. 24 and 25 is generally similar to the embodiment of the invention illustrated in FIGS. 1–23, similar numerals will be utilized to designate similar components, the suffix letter "g" being associated with the numerals of FIGS. 24 and 25 to avoid confusion.

An anchor inserter apparatus 20g has the same general construction as the anchor inserter apparatus 20c of FIG. 11. Thus, the anchor inserter apparatus 20g includes a tubular outer member 94g having a passage 204g which extends between an exit opening 208g at a leading end portion 242g of the tubular outer member 94g and an entrance opening (not shown) at the opposite end of the tubular outer member 94g. A straight slot 102g extends between axially opposite ends of the tubular outer member 94g. An inner member, not shown, corresponding to the inner member 92c of FIG. 11, is axially movable in the passage 204g.

In accordance with a feature of this embodiment of the invention, an anchor retainer 280g (FIG. 24) is engageable with a passage 236g which forms a recess in an anchor 30g (FIG. 25). In the illustrated embodiment of FIGS. 24 and 25, a suture 32g has an inner leg 64g which extends through the passage 236g to a connector section 66g of the suture. The anchor 30g has the same general construction as the suture anchor 30f of FIG. 23. However, the anchor 30g (FIG. 25) does not have an annular recess corresponding to the recess 300 in the anchor 30f of FIG. 23.

The retainer 280g (FIGS. 24 and 25) has a circular, generally hemispherical-shaped, projection 304g which extends radially inward from an inner side surface 230g of the passage 204g in the tubular outer member 94g. The projection 304g is formed by indenting the outside of the tubular outer member 94g. The hemispherical projection 304g has a maximum diameter which is greater than the diameter of the passage 236g (FIG. 25) which extends radially through the suture anchor 30g. The projection 304g is disposed diametrically opposite from the slot 102g (FIG. 24).

The projection 304g extends through an open end 310 (FIG. 25) of the passage 236g which forms a recess in the anchor 30g. The projection 304g engages the open end portion 310 of the passage 236g to hold the anchor 30g against axial movement relative to the tubular outer member 94g (FIG. 25). The projection 304g presses the leg 64g of the suture 32g against the open end 310 of the passage 236g to hold the suture 32g against movement relative to the anchor 30g. The projection 304g also presses a portion of a cylindrical outer side surface 50g on the anchor 30g against a portion of the inner side surface 230g of the passage 204g adjacent to the slot 102g (FIG. 24). If desired, a closed ended recess could be substituted for the open ended recess formed by the passage 236g and the suture 32g omitted.

When the anchor 30g is to be inserted into the anchor inserter apparatus 20g with the suture 32g connected with the anchor, the anchor may be moved through an entrance opening, corresponding to the entrance opening 206 of FIG. 11, and into the passage 204g. The anchor 30g is moved along the passage 204g until the leading end portion (not shown) of the anchor 30g engages the projection 304g.

An inner member, corresponding to the inner member 92c of FIG. 11, then applies an axial force against the trailing end portion 38g of the anchor 30g. This causes the leading end portion of the anchor 30g to cam or force the projection 304g radially outward. As the projection 304g is forced radially outward by the anchor 30g, the width of a portion of the slot 102g (FIG. 24) in the end portion 242g of the tubular outer member 94g increases and the end portion of the tubular outer member is resiliently expanded.

Continued rightward (as viewed in FIGS. 24 and 25) movement of the anchor 30g (FIG. 25) relative to the tubular outer member 94g moves the projection 304g into alignment with a leading passage through the anchor 30g, that is into alignment with a passage corresponding to the passage 238f in the anchor 30f of FIG. 23. If desired, the anchor 30g could be positioned relative to the tubular outer member 94g with the projection 304g engaging the leading passage, that is the passage corresponding to the passage 238f of FIG. 23, in the suture anchor 30g. However, it is believed that it will be preferred to have the anchor 30g extend further outward from the tubular outer member 94g. Therefore, the application of force against the trailing end portion 38g of the anchor 30g by the inner member, corresponding to the member 92c of FIG. 11, is continued.

The continued application of force to the trailing end portion 38g of the anchor 30g disengages the projection 304g from the leading passage through the anchor 30g. Continued rightward (as viewed in FIG. 25) axial movement of the anchor 30g moves the projection 304g into alignment with the passage 236g in the anchor 30g. When the projection 304g snaps into the open end portion 310 of the passage 236g, the application of force to the trailing end portion 38g of the anchor 30g is interrupted. At this time, the anchor 30g is held against movement relative to the tubular outer member 94g by engagement of the projection 304g with the open end portion 310 of the passage 236g.

The foregoing explanation has assumed that the anchor 30g is moved into the passage 204g at the entrance opening, corresponding to the entrance opening 206 of FIG. 11. However, the anchor 30g could be moved into the passage 204g through the exit opening 208g if desired. When the anchor 30g is inserted through the exit opening 208g, the trailing end portion 38g of the anchor 30g moves into engagement with the projection 304g. Continued leftward (as viewed in FIG. 25) movement of the anchor 30g resiliently deflects the projection 304g. As this occurs, the width of the slot 102g increases.

As the anchor 30g continues to move toward the left (as viewed in FIG. 25) relative to the projection 304g, the projection engages the outer side surface 50g of the anchor 30g and slides along the outer side surface. Continued leftward movement of the anchor 30g relative to the projection 304g results in the projection moving into engagement with the open end portion 310 of the passage 236g through the suture anchor 30g. Once this occurs, the anchor 30g is held against axial movement relative to the tubular outer member 94g.

After the anchor inserter apparatus 20g has been assembled, in the manner previously described, the apparatus is used to position the anchor 30g relative to body tissue in the same manner as previously described in conjunction with FIGS. 13–15. After the anchor 30g has been positioned relative to an opening in bone or other body tissue, in the manner illustrated in FIG. 13, the inner member is moved relative to the tubular outer member 94g. The force applied against the trailing end 38g of the anchor 30g disengages the anchor from the projection 304g.

Continued relative movement between the inner member and tubular outer member 94g moves the anchor 30g out of the passage 204g in the tubular outer member. When the anchor 30g has moved to the desired depth into the body tissue, the orientation of the anchor may be changed by tensioning the legs of the suture 32g. This pivots or toggles the anchor 30g in the same manner as previously described in conjunction with FIGS. 14 and 15.

The anchor 30g illustrated in FIG. 25 has the same tubular construction as the anchor 30f of FIG. 23. However, the anchor 30g could have the solid cylindrical construction of the suture anchor 30e of FIGS. 21 and 22 if desired. In fact, the anchor 30g could have any desired construction. For example, the anchor 30g could have a polygonal construction similar to that in the aforementioned U.S. Pat. No. 5,549,630. Alternatively, the anchor could have any one of the constructions illustrated in the aforementioned U.S. Pat. No. 5,403,348.

In the embodiment of the invention illustrated in FIGS. 24 and 25, the projection 304g is integrally formed as one piece with the tubular outer member 94g. However, it is contemplated that the projection 304g could be formed separately from the tubular outer member 94g. For example, the projection 304g could be provided by a spring loaded plunger.

The use of such a spring loaded plunger would eliminate the necessity of resiliently deflecting the tubular outer member 94b as the projection 304g moves into engagement with a anchor 30g. This would enable the slot 102g to be eliminated. However, it is believed that it will be preferred to retain the slot 102g in the tubular outer member 94g to facilitate positioning of the suture 32g relative to the tubular outer member during assembly and to facilitate disengagement of the tubular outer member 94g from the suture after the suture anchor 30g has been positioned relative to body tissue in the manner explained in conjunction with FIGS. 13 through 15. Of course, if the suture 32 is omitted, the slot 102g could be omitted.

Suture Anchor Retainer—Plural Projections

In the embodiment of the invention illustrated in FIGS. 24 and 25, the anchor retainer 280g includes a single projection 304g which engages an open end portion 310 of the passage 236g formed in the anchor 30g. In the embodiment of the invention illustrated in FIGS. 26 and 27, a plurality of projections are provided to engage the open ends of a plurality of passages or recesses in an anchor. Since the embodiment of the invention illustrated in FIGS. 26 and 27 is generally similar to the embodiment of the invention illustrated in FIGS. 1–25, similar numerals will be utilized to designate similar components, the suffix letter "h" being associated with the numerals of FIGS. 26 and 27 to avoid confusion.

An anchor insertion apparatus 20h (FIG. 26) includes a tubular outer member 94h having a passage 204h with an exit opening 208h. A slot 102h extends between axially opposite ends of the tubular outer member 94h in the same manner as previously explained in conjunction with the embodiment of the invention illustrated in FIG. 11. The anchor inserter apparatus 20h has the same general construction as the anchor inserter apparatus 20c of FIG. 11.

In accordance with a feature of this embodiment of the invention, an anchor retainer 280h includes a pair of identical projections 320 and 322. The projections 320 and 322 have the same generally hemispherical configuration as the projection 304g of FIGS. 24 and 25. The two projections 320 and 322 are disposed diametrically opposite from the slot 102h. The two projections 320 and 322 are integrally formed as one piece with the tubular outer member 94h by indenting the tubular outer member.

The two projections 320 and 322 engage open ends of passages 236h and 238h in the same manner as in which the single projection 304g of FIGS. 24 and 25 engages the open end portion 310 of the passage 236g (FIG. 25). Thus, the projection 320 engages an open end portion 324 of the passage 236h. Similarly, the projection 322 engages an open end portion 326 of the passage 238h (FIG. 27). If desired, closed ended recesses could be substituted for the open ended recesses formed by the passages 236h and 238h.

The suture 32h has outer and inner legs 62h and 64h which extend through the passages 236h and 238h. The projections 320 and 322 extend into the open end portions 324 and 326 of the passages 236h and 238h and press the suture legs 62h and 64h against the open end portions of the passages. A connector section 66h extends between the open end portions 324 and 326 of the passages 236h and 238h. The two projections 320 and 322 press a portion of an outer side surface 50h on the anchor 30h against a portion of an inner side surface 230g of the passage 204h adjacent to the slot 102h. If desired, the suture 32h could be omitted.

When the anchor inserter apparatus 20h is to be assembled, the anchor 30h may be inserted through the entrance opening, corresponding to the entrance opening 206 of FIG. 11, into the passage 204h (FIGS. 26 and 27). The anchor 30h is then moved axially along the passage 200h until a leading end portion 44h of the anchor engages the projection 320.

An inner member, corresponding to the inner member 92c of FIG. 11, applies force against a trailing end portion 38h of the anchor 30h. This force is transmitted from the leading end portion 44h of the anchor 30h to the projection 320 (FIG. 27). The force applied against the projection 320 resiliently deflects the tubular outer member 94h. As this occurs, the width of the slot 102h increases.

As the anchor 30h continues to move forward, that is toward the right as viewed in FIG. 27, the open end portion 326 of the leading passage 230h through the anchor 30h moves into alignment with the projection 320. As this occurs, the projection 320 snaps into the open end portion 326 of the passage 238h. Continued application of force to the trailing end portion 38h of the anchor 30h continues to move the anchor toward the right (as viewed in FIG. 27). As this occurs, the projection 320 becomes disengaged from the open end portion 326 of the passage 238h and the anchor moves toward the position shown in FIG. 27.

As the anchor moves into the position shown in FIG. 27, the projection 322 snaps into the open end portion 326 of the passage 238h. At the same time, the projection 320 snaps into the open end portion 324 of the passage 236h. This results in the anchor 30h being held in place by engagement of the projections 320 and 322 in the anchor 30h.

In the foregoing explanation, the anchor 30h was moved from the entrance opening rightward (as viewed in FIG. 27) toward the exit opening 208h from the passage 204h. It is contemplated that the anchor 30h could be inserted into the passage 204h in the tubular outer member 94h through the exit opening 208h. This would eliminate the necessity of moving the anchor 30h through a relatively long distance along the passage 204h.

The anchor inserter apparatus 20h is used to position the anchor 30h (FIG. 27) relative to body tissue in the same manner as previously explained in conjunction with the embodiments of the invention illustrated in FIGS. 1–25. Thus, an inner member, corresponding to the inner member 92c of FIG. 11, is moved relative to the outer member 94h. The force applied against the trailing end portion 38h of the suture anchor 30h resiliently deflects both of the projections 320 and 322 outwardly away from the slot 102f to disengage the projections from the open end portions 324 and 326 of the passages 236h and 238h. As this occurs, the width of the slot 102h increases.

As the anchor 30h moves axially outward from the position shown in FIG. 27, the suture passage 238 in the suture anchor 30h moves out of the passage 204h in the tubular outer member 94h. As this occurs, the projection 322 resiliently snaps into the open end portion 324 of the suture passage 236h in the anchor 30h. The continued application of force against the trailing end portion 38h of the anchor 30h by the inner member (not shown) again resiliently deflects the projection 322 to disengage the projection 322 from the open end portion 324 of the suture passage 236h.

Continued movement of the inner member relative to the tubular outer member 94h separates the anchor 30h from the tubular outer member. When the anchor 30h has been moved to a desired position relative to the body tissue, the suture anchor may be pivoted to change its orientation in the manner disclosed in the aforementioned U.S. Pat. No. 5,403,348. The inner member and the tubular outer member 94h are then disengaged from the body tissue. The suture legs 62h and 64h can be easily disengaged from the open slot 102h.

The foregoing description has assumed that positioning of the anchor 30h relative to body tissue is to be accomplished by moving the inner member relative to the tubular outer member 94h. However, if desired, the inner member could be held stationary relative to the body tissue and the tubular outer member 94h moved relative to the inner member to separate the anchor 30h from the tubular outer member.

Anchor Retainer Spring

In the embodiment of the invention illustrated in FIGS. 23–27, projections integrally formed with the tubular outer member have been utilized to retain the anchor in a desired position relative to the tubular outer member. In the embodiment of the invention illustrated in FIG. 28, a separate spring member is utilized to retain an anchor in a desired position relative to the tubular outer member. Since the embodiment of the invention illustrated in FIG. 28 is generally similar to the embodiment of the invention illustrated in FIGS. 11–27, similar numerals will be utilized to designate similar components, the suffix letter "j" being associated with the numerals of FIG. 28 to avoid confusion.

Figure 28:
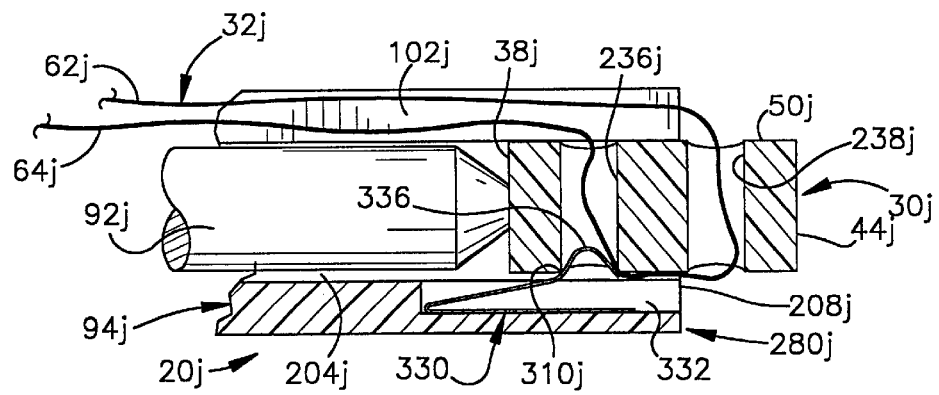
FIG. 28 is a schematic sectional view of another embodiment of the invention, having the same general construction as the embodiment of FIG. 11, and illustrating the manner in which a spring on a tubular outer member engages an end portion of a passage in an anchor.

In the embodiment of the invention illustrated in FIG. 28, the anchor inserter apparatus 20j has the same general construction as the anchor inserter apparatus 20c of FIG. 11. The anchor inserter apparatus 20j of FIG. 28 includes a cylindrical tubular outer member 94j and a cylindrical inner member 92j. An anchor retainer 280j retains an anchor 30j in a cylindrical passage 204j which extends axially through the tubular outer member 94j. The specific anchor 30j illustrated in FIG. 28 is a suture anchor.

A suture 32j is connected with the suture anchor 30j. The suture 32j has outer and inner legs 62j and 64j. The legs 62j and 64j of the suture 32j are disposed in a slot 102j which extends between axially opposite ends of the tubular outer member 94j. If the suture 32j is omitted, the slot 102j could be omitted.

In accordance with a feature of this embodiment of the invention, the anchor retainer 280j includes a spring 330 which is disposed in a recess or slot 332 formed in the tubular outer member 94j opposite from the slot 102j. The spring 330 has a projection 336 which extends through an open end portion 310j of a passage 236j in the anchor 30j. Engagement of the projection 336 on the spring 330 with the open end portion 310j of the passage 236j holds the anchor 30j against movement relative to the tubular outer member 94j. The spring 330 is fixedly connected to the tubular outer member 94j.

When the anchor 30j is to be positioned in the anchor inserter apparatus 20j, the anchor 30j is inserted through an entrance opening to the passage 204j. Thus, the anchor 30j is inserted through an opening corresponding to the opening 206 of FIG. 11 adjacent to a handle portion of the anchor inserter apparatus 20j. The anchor 30j is moved along the passage 204j until a leading end portion 44j engages the projection 236 on the spring 330.

The inner member 92j then applies force against a railing end portion 38j of the anchor 30j. Force is transmitted from the leading end portion 44j of the anchor 30j to the projection 336 to resiliently deflect the spring 330 radially outward, that is downward as viewed in FIG. 28. This results in the spring 330 being moved into the slot 332 in the tubular outer member 94j. In this embodiment of the invention, the width of the slot 102j remains constant as the anchor 30j moves into and/or out of the tubular outer member 94j.

Continued movement of the anchor 30j toward the exit opening 208j results in the projection 336 engaging a cylindrical outer side surface 50j on the anchor 30j adjacent to the leading end portion 44j of the suture anchor. As the rightward (as viewed in FIG. 28) movement of the anchor 30j continues, the projection 336 on the spring 330 snaps into an open end portion of the passage 238j in the anchor.

Continued movement of the inner member 92j and anchor 30j toward the right (as viewed in FIG. 28) relative to the tubular outer member 94j results in the spring projection 336 moving out of engagement with the passage 238j and into engagement with the cylindrical outer side surface 50j of the anchor 30j at a location between the two passages 236j and 238j. As the rightward movement of the anchor 30j continues, the spring projection 336 snaps into the passage 236j in the anchor 30j in the manner illustrated schematically in FIG. 28. When this occurs, the application of force to the inner member 92j is interrupted. This results in the anchor 30j being held in place with the trailing end portion 38j disposed in the passage 204j and the leading end portion 44j of the anchor 30j extending outward from the tubular outer member 94j.

In the embodiment of the invention illustrated in FIG. 28, the anchor 30j is formed from a solid cylindrical piece of material. The two radially extending passages 236j and 238j are formed in the solid piece of cylindrical material. However, if desired, the suture anchor 30j could be formed with the tubular configuration illustrated in FIGS. 23, 25 and 27. Rather than engaging the open end recess formed by the passage 236j, the spring 330 could engage a closed end recess formed in the suture anchor 30j at a location offset from the passages 236j and 238j. It is contemplated that the suture anchor 30j could have any desired configuration and could be used either with or without the suture 32j.

If desired, the anchor 30j could be inserted into the passage 204j through the opening 208j. this would eliminate engagement of the spring 300 with the anchor passage 238j during positioning of the anchor 30j in the suture anchor retainer 280j.

In the embodiment of the invention illustrated in FIG. 28, the slot 102j extends between axially opposite ends of the tubular outer member 94j. It is contemplated that the slot 102j could be eliminated or that the slot could extend from the exit opening 208*j* through a distance which is shorter than the axial extent of the tubular outer member 94*j*. However, it is believed that it may be preferred to have the slot 102*j* extend between axially opposite ends of the tubular outer member 94*j* to facilitate positioning of the outer and inner suture legs 62*j* and 64*j* relative to the tubular outer member 94*j*. In addition, by having the slot 102*j* extend between axially opposite ends of the outer member 94*j*, disengagement of the suture 32*j* from the tubular outer member is facilitated after the anchor 30*j* has been positioned relative to body tissue. Of course, if the suture 32*j* is omitted, the slot 102*j* could be omitted.

It is contemplated that the anchor 30*j* will be positioned relative to body tissue in the same manner illustrated schematically in FIGS. 13–15. However, it should be understood that the anchor 30*j* could be positioned relative to body tissue in a different manner if desired. It should be understood that the anchor inserter apparatus 20*j* could be utilized to position the anchor 30*j* relative to either hard body tissue, such as bone, or soft body tissue, such as a patient's skin or internal organs.

Anchor Retainer on Inner Member

Figure 29:
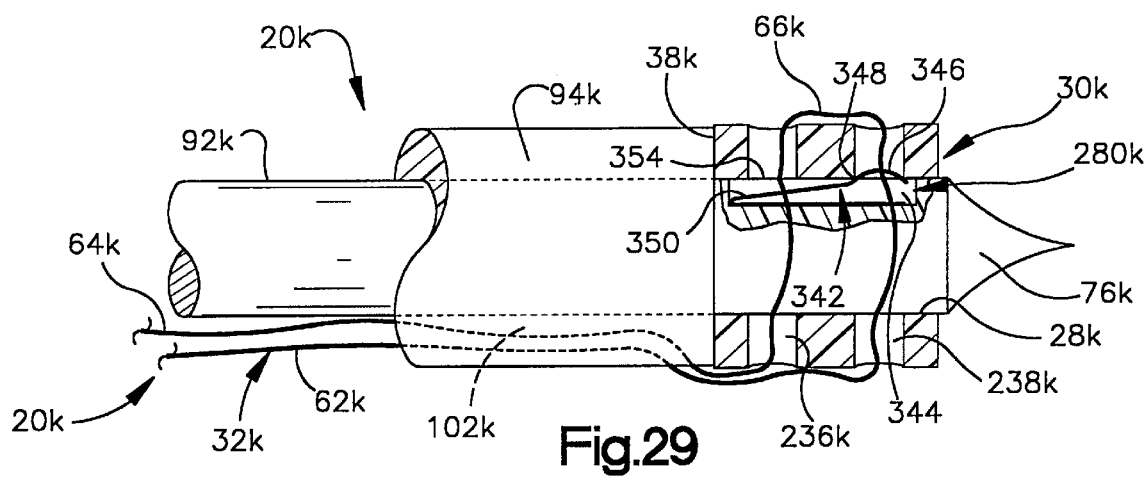
FIG. 29 is a schematic sectional view of another embodiment of the invention, having the same general construction as the embodiment of FIG. 1 and illustrating the manner in which a spring on an inner member engages an end portion of a passage in an anchor.

In the embodiment of the invention illustrated in FIGS. 19–28, an anchor retainer has been disposed on a tubular outer member to retain the anchor against relative movement relative to the tubular outer member. In the embodiment of the invention illustrated in FIG. 29, an anchor retainer is disposed on an inner member to retain the anchor against movement relative to the inner member. Since the embodiment of the invention illustrated in FIG. 29 is generally similar to the embodiment of the invention illustrated in FIGS. 1–28, similar numerals will be utilized to designate similar components, the suffix letter "k" being associated with the numerals of FIG. 29 to avoid confusion.

An anchor inserter apparatus 20*k* includes an inner member 92*k* (FIG. 29) which is fixedly connected with a handle (not shown) in the same manner as previously described in connection with the embodiment of the invention illustrated in FIGS. 1–3. A tubular outer member 94*k*, is axially slidable along the inner member 92*k*. A slot 102*k* extends between axially opposite ends of the outer member 94*k* and is axially aligned with a corresponding slot in the handle portion of the suture anchor inserter apparatus 20*k*. An anchor 30*k* is disposed on the axially outer end portion of the inner member 92*k* adjacent to a point 76*k* on the inner member 92*k*.

In accordance with a feature of this embodiment of the invention, an anchor retainer 280*k* is mounted on the inner member 92*k* to hold the anchor 30*k* in a desired position relative to the anchor inserter apparatus 20*k*. The anchor 30*k* includes a pair of radially extending passages 236*k* and 238*k* which extend diametrically through the anchor 30*k*. The passages 236*k* and 238*k* have a cylindrical configuration. The anchor 30*k* has a tubular configuration with a central passage 28*k* which is intersected by the suture passages 236*k* and 238*k*.

In accordance with a feature of the present invention, a spring 342 is mounted in a slot 344 in the inner member 92*k*. The spring 342 has a projection 346 which engages an inner end portion 348 of the passage 238*k*. The projection 346 extends into the passage 338*k* and holds the suture anchor 30*k* against movement relative to the inner member 92*k*. The spring 342 has an end portion 350 which is fixedly connected with the inner member 92*k*.

When the anchor 30*k* is to be positioned on the inner member 92*k*, the cylindrical axial passage 28*k* through the anchor 30*k* is aligned with the longitudinal central axis of the inner member 92*k* and the point 76*k*. At this time, the suture 32*k* may be connected with the anchor 30*k*. Thus, the outer leg 62*k* of the suture 32*k* extends through the radial passage 238*k* in the anchor 30*k*. Similarly, the inner leg 64*k* extends through the passage 236*k* in the anchor 30*k*. A connector section 66*k* interconnects the two legs 62*k* and 64*k* of the suture 32*k*.

As the trailing end portion 38*k* of the anchor 30*k* is moved past the point 76*k* and onto the cylindrical body of the inner member 92*k*, the trailing end portion 38*k* of the anchor 30*k* engages the projection 346 on the spring 342. The axial force applied against the spring 342 by the trailing end portion 38*k* of the anchor 30*k* deflects the spring 342 into the slot 344. The projection 346 on the spring 342 then engages the open end portion 354 of the passage 236*k*.

Continued application of force against the anchor 30*k* results in the spring 342 again being deflected into the slot 344. As the anchor 30*k* continues to move onto the inner member 92*k*, the projection 346 on the spring 342 snaps into the open end portion 348 of the passage 238*k*. This holds the anchor in the position shown in FIG. 29.

Once the anchor 30*k* has been positioned on the outer end portion of the inner member 92*k*, in the manner illustrated in FIG. 29, the outer and inner legs 62*k* and 64*k* of the suture 32*k* may be positioned in the slot 102*k* in the tubular outer member 94*k*. The legs 62*k* and 64*k* of the suture 32*k* are also positioned in a slot in the handle of the anchor inserter apparatus. The slot (not shown) in the handle of the anchor inserter apparatus 20*k* is aligned with the slot 102*k* in the tubular outer member 94*k*.

Once the anchor 30*k* has been positioned on the outer end portion of the inner member 92*k*, the point 76*k* of the outer member 92*k* may be utilized to pierce relatively soft body tissue. The anchor 30*k* is then separated from the inner member 92*k* and moved into the body tissue by movement of the tubular outer member 94*k* axially outward along the inner member 92*k*. The orientation of the anchor 30*k* is then changed in the same manner as explained in conjunction with the embodiment of the invention illustrated in FIGS. 1–3.

In the embodiment of the invention illustrated in FIG. 29, the spring 342 has a single projection 346 which engages the inner open end portion 348 of the passage 238*k* in the anchor 30*k*. If desired, the projection on the spring could engage the inner open end portion 354 of the passage 236*k* on the anchor 30*k*. If this was to be done, the orientation of the spring 242 in the slot 344 would be changed by 180 so that the projection 346 would be adjacent to the left (as viewed in FIG. 29) end of the slot 344 while the end 350 of the spring would be adjacent to the right end of the slot 344. Alternatively, the spring 342 could be provided with two projections to engage each of the passages 236*k* and 238*k*.

Anchor Retainer

Figure 30:
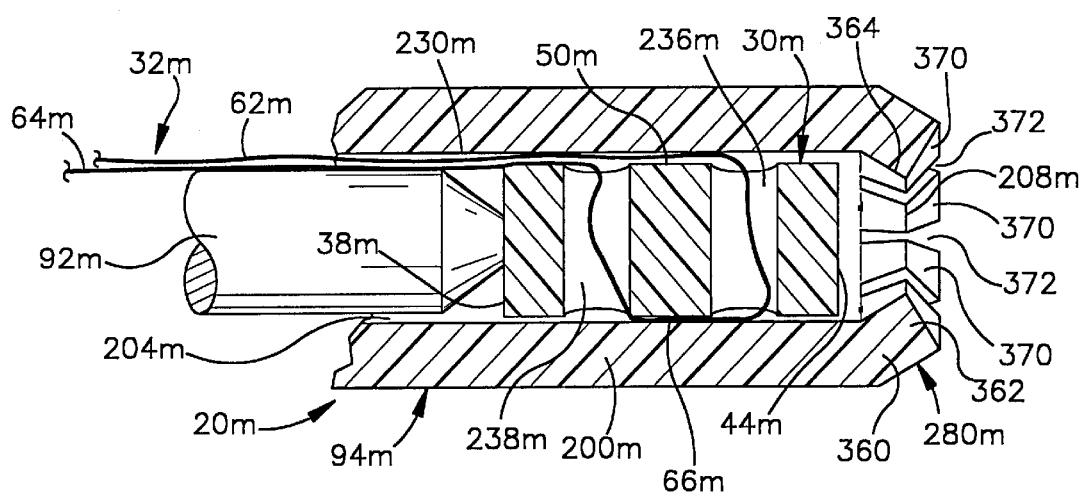
FIG. 30 is a schematic sectional view of another embodiment of the invention, having the same general construction as the embodiment of FIG. 11, and illustrating a contracted end portion of a tubular outer member as an anchor is moved toward the end portion of the tubular outer member.

In the embodiment of the invention illustrated in FIGS. 19–22, the anchor retainer 280 projects radially inward from one side of the tubular outer member 94*e* (FIG. 19). In the embodiment of the invention illustrated in FIG. 30, the anchor retainer has an annular configuration and extends inward from the cylindrical side wall of the tubular outer member for the same distance throughout the extent of the tubular side wall. Since the embodiment of the invention illustrated in FIG. 30 is generally similar to the embodiment of the invention illustrated in FIGS. 1–29, similar numerals will be utilized to designate similar components, the suffix letter "m" being associated with the numerals of FIG. 30 to avoid confusion.

An anchor inserter apparatus 20m includes a cylindrical tubular outer member 94m and a cylindrical inner member 92m which are disposed in a coaxial relationship. In accordance with a feature of this embodiment of the invention, an anchor retainer 280m is provided at one end, that is, the right end as viewed in FIG. 30, of the tubular outer member 94m. The anchor retainer 280m has an annular configuration.

The annular retainer 280m has an axially inner end portion 360 which is connected to a tubular cylindrical body 200m of the tubular outer member 94m. The retainer 280m has an axially outer end portion 362 which defines a circular exit opening 208m having a central axis which is coincident with a longitudinal central axis of the cylindrical body 200m of the tubular outer member 94m. The anchor retainer 280m has an annular inner side surface 364 which tapers radially inward and axially outward. Although the anchor retainer 280m has been illustrated in FIG. 30 as having a plurality of slots to facilitate flexing of the anchor retainer, the slots could be omitted if desired.

When the anchor 30m is to be positioned in the anchor inserter apparatus 20m, the suture anchor 30m is moved through an opening at an end of the tubular outer member 94m opposite from the exit opening 208m. Thus, the anchor 30m is moved through an opening corresponding to the entrance opening 206 adjacent to the handle 22c of the embodiment of the invention illustrated in FIG. 11. At this time, the suture 32m may be connected with the anchor 30m. Thus, an outer leg 62m of the suture 32m extends through a passage 236m formed in the suture anchor 30m. Similarly, the inner leg 64m of the suture 32m extends through a passage 238m formed in the suture anchor 30m. The two legs 62m and 64m of the suture 32m are interconnected by a connector section 66m.

In the embodiment of the invention illustrated in FIG. 30, the tubular outer member 94m has a continuous cylindrical outer side surface. Thus, a slot, corresponding to the slot 102c of FIG. 11, is not formed in the tubular outer member 20m. Therefore, the outer and inner legs 62m and 64m of the suture 32m are received in a cylindrical passage 204m formed in the tubular outer member 94m. The suture legs 62m and 64m extend along an outer side surface of the cylindrical inner member 92m. Of course, if desired, a slot corresponding to the slot 102c of FIG. 11 could be formed in the tubular outer member 94m. If desired, the anchor 30m could be designed for use without the suture 32m.

The pusher member 92m moves the anchor 30m forward, that is toward the right as viewed in FIG. 30, until a leading end portion 44m of the anchor 30m engages the inwardly tapering or sloping side surface 364 of the anchor retainer 280m. When this occurs, the force applied by the inner member 92m against the trailing end portion 38m of the anchor 30m is increased. This increased force deflects the annular anchor retainer 280m radially and axially outward and increases the diameter of the exit opening 208m. Thus, force applied by the leading end portion 44m of the anchor 30m against the slotted annular surface 364 flexes sections 370 radially outward away from the longitudinal central axis of the tubular outer member 94m. As this occurs, the width of slots 372 between the sections 380 increases.

As the anchor 30m is moved toward the right (as viewed in FIG. 30) by the inner member 92m relative to the outer member 94m, the sections 370 of the suture anchor retainer 280m move into engagement with a cylindrical outer side surface 50m on the suture anchor 30m. As the anchor 30m continues to be pushed through the exit opening 208m, the sections 370 of the suture anchor retainer 280m slide along the outer side surface 50m on the suture anchor 30m. When the anchor 30m has been moved to a desired position relative to the tubular outer member 94m, the outward movement of the anchor through the exit opening 208m is interrupted. At this time, the sections 370 of the anchor retainer 280m resiliently grip the cylindrical outer side surface 50m of the anchor 30m to hold the anchor against movement relative to the tubular outer member 94m.

When the anchor 30m is to be positioned relative to body tissue, the tubular outer member 94m and the cylindrical suture anchor 50m are aligned with an opening in the body tissue, in the same manner as is illustrated in FIG. 13. The tubular inner member 92m is then moved toward the right (as viewed in FIG. 30) to push the anchor 30m into the body tissue. The orientation of the anchor 30m relative to the body tissue is then changed in the manner illustrated in FIG. 15 for the anchor inserter apparatus 22c.

It is preferred to move the anchor 30m to a position in which the leading end portion 44m of the anchor extends axially outward from the tubular outer member 94m and the retainer 280m grips the outer side surface 50m of the anchor. However, the anchor 30m could remain completely within the passage 204m in the tubular outer member 94m if desired. If this is to be done, the force applied against the trailing end portion 38m of the anchor 30m by the inner member 92m would press the leading end portion 44m of the suture anchor against the surface 364 without deflecting the sections 370 of the suture retainer 280m. Of course, when the anchor 30m is to be positioned in body tissue, the force applied against the anchor 30m by the inner member 92m would be increased and the sections 370 of the retainer would be deflected in the manner previously explained.

In the embodiment of the invention illustrated in FIG. 30, the tubular outer member 94m is formed of metal. The sections 370 of the anchor retainer 280m are formed by first forming the slots 372 in the outer end of a cylindrical tubular member. The sections are then deflected inward to the positions shown in FIG. 30 to form the annular retainer 280m. It should be understood that the tubular outer member 94m and the retainer 280m could be molded as one piece of polymeric material. If this was done, it is contemplated that it may be preferred to mold the sections 370 of the retainer 280m in the orientation shown in FIG. 30.

The slots 372 separate the sections 370 of the anchor retainer 280m and facilitate resilient deflection of the sections of the anchor retainer by the leading end portion 44m of the anchor. However, the number of slots 372 and sections 370 could be reduced if desired. Thus, only a single slot, or perhaps two or three slots 372, could be formed in the tubular outer member 94m. The resulting section or sections would then be plastically deformed to form the inner side surface 230m of the passage 204m into the frustrum of a cone of the suture anchor retainer 280m. As was previously mentioned, the slots 372 could be completely eliminated if desired.

Anchor Inserter Apparatus

An alternative embodiment of the anchor inserter apparatus is illustrated in FIGS. 31–37. Since the embodiment of the anchor inserter apparatus illustrated in FIGS. 31–37 is generally similar to the embodiment of the suture anchor inserter apparatus illustrated in FIGS. 1–30, similar numerals will be utilized to designate similar components, the suffix letter "n" being added to the numerals of FIGS. 31–37 to avoid confusion.

An anchor inserter apparatus 20n includes a tubular outer member 94n (FIG. 31). The tubular outer member 94n includes a one piece cylindrical tubular body 200n. A cylindrical passage 204n extends axially through the tubular outer member 94n between a circular entrance opening 206n and a circular exit opening 208n. A straight longitudinally extending slot 102n is formed in the tubular outer member 94n and extends between the entrance opening 206n and the exit opening 208n.

A handle 22n includes a cylindrical collar 380 which extends around the tubular outer member 94n. The slot 102n extends through the collar 380. The handle 22n also includes an outwardly extending section 382 which is manually engageable to position the tubular outer member 94n relative to body tissue. The section 382 has a longitudinal central axis which is skewed at an acute angle to the longitudinal central axis of the tubular outer member 94n and the longitudinal central axis of the slot 102n. The longitudinal central axis of the section 382 of the handle 22n intersects the longitudinal central axis of the tubular outer member 94n.

An anchor retainer 280n is disposed adjacent to a leading end portion 242n of the tubular outer member 94n. The illustrated embodiment of the suture anchor retainer 280n includes a projection 304n having the same generally hemispherical configuration as the projection 304g of FIGS. 24 and 25. The projection 304n is disposed diametrically opposite from the slot 102n. The projection 304n has a central axis which extends perpendicular to and intersects the central axes of the passage 204n and slot 102n.

In accordance with a feature of this embodiment of the invention, two inner or pusher members are sequentially used in association with the tubular outer member 94n. Thus, an anchor positioning push rod or inner member 386 (FIG. 32) is utilized to position an anchor relative to the tubular outer member 94n and anchor retainer 280n (FIG. 31). An anchor deployment push rod or inner member 388 (FIG. 33) is subsequently utilized to push the anchor out of the tubular outer member 94n (FIG. 31). The anchor deployment push rod 388 (FIG. 33) is longer than the anchor positioning push rod 386 (FIG. 32).

The two inner members 386 and 388 (FIGS. 32 and 33) are sequentially inserted into the passage 204n (FIG. 31) after the anchor has been inserted into the passage. Thus, when the anchor 30n (FIG. 34) is to be initially positioned in the passage 204n, the anchor positioning push rod 386 is inserted into the passage 204n. A leading end surface 393 (FIG. 32) on the anchor positioning push rod 386 applies force to the trailing portion of the anchor 30m (FIG. 35) to move the anchor along the passage 204n. The anchor 30n is moved to a position in which a trailing end portion of the anchor is disposed within the passage 204n and a leading end portion of the anchor extends outwardly from the tubular outer member 94n (FIG. 36). The anchor positioning push rod 386 is then withdrawn from the passage 204n.

When the anchor 30n is to be positioned relative to body tissue, the deployment push rod 388 (FIG. 33) is inserted into the passage 204n. The anchor deployment push rod 388 is longer than the anchor positioning push rod 386. Therefore, the anchor deployment push rod 388 is effective to move the trailing end portion of the suture anchor out of the passage 204n into body tissue.

The anchor positioning push rod or inner member 386 includes a cylindrical body 392 (FIG. 32). The body 392 has a circular end surface 393. A cylindrical stop or handle section 394 is connected with the cylindrical body 392. The stop or handle section 394 has an annular stop surface 396 which is coaxial with the cylindrical body 392 of the anchor positioning push rod or inner member.

The anchor deployment push rod 388 (FIG. 33) has a construction similar to the anchor positioning push rod 386 (FIG. 32). The anchor deployment push rod (FIG. 33) includes a cylindrical body 398. The cylindrical body 398 (FIG. 33) of the anchor deployment push rod 388 has a length which exceeds the length of the anchor positioning push rod 386 by more than the maximum depth to which an anchor is to be moved into body tissue. A cylindrical stop or handle section 400 is disposed in a coaxial relationship with the cylindrical body 398 of the anchor deployment push rod or inner member 388.

The cylindrical body 398 of the anchor deployment push rod or inner member 388 (FIG. 33) has indicia 404 which cooperates with an annular end surface 408 (FIG. 31) on the tubular outer member 94 to indicate the position of a leading end or pusher surface 410 on the anchor deployment push rod 388 (FIG. 33) relative to the tubular outer member 94. The indicia 404 (FIG. 33) cooperates with the end surface 408 (FIG. 31) on the tubular outer member 94m to indicate the depth to which the anchor deployment push rod or inner member 388 has pushed the anchor 30n (FIG. 36) into body tissue. The inner member 92c of the embodiment of the invention illustrated in FIG. 11 could be provided with indicia corresponding to the indicia 404 if desired.

During assembly of the anchor inserter apparatus 20n, an anchor 30n (FIG. 34) is inserted into the passage 204n in the tubular outer member 94n. At this time, the suture 32n may be connected with the suture anchor 30n and the legs 62n and 64n are aligned with and extend through the slot 102n in the tubular outer member 94n. The anchor 30n has an outside diameter which is smaller than the inside diameter of the portion of the passage 204n ahead of the suture anchor retainer 280n.

The cylindrical body 392 (FIG. 35) of the anchor positioning push rod 386 is inserted into the passage 204n in the tubular outer member 94n. The leading end surface 393 on the anchor positioning push rod 386 pushes the anchor 30n toward the anchor retainer 280n at the leading end portion 242m of the tubular outer member 94n. The leading end portion of the anchor 30n applies force against and resiliently deflects a projection 304n in the anchor retainer 280n (FIGS. 35 and 37).

The projection 304n has the same hemispherical configuration as the projection 304g of FIG. 24. The projection 304n (FIG. 37) is disposed opposite from the slot 102n and has a central axis which extends perpendicular to and intersects parallel central axes of the tubular outer member 94n and the slot 102n. As the projection 304n is resiliently deflected, the width of the slot 102n opposite from the projection increases.

When the anchor 30n has been moved to a desired position relative to the anchor retainer 280n (FIG. 37), the stop surface 396 on the stop section 394 of the inner member 386 (FIG. 36) is in abutting engagement with the end surface 408 on the tubular member 94n. At this time, the anchor 30n is positioned with a leading end portion of the anchor extending outward from the tubular member 94n and with a trailing end portion of the anchor 30n disposed in the passage 204n (FIG. 37). The anchor retainer 280n is effective to firmly grip the anchor 30n when the anchor is in the position shown in FIGS. 36 and 37.

The projection 304n (FIG. 37) is effective to press the anchor 30n against an inner side surface of the passage 204n opposite from the projection 304n. At this time, the tubular outer member 94n is deflected by force applied against the projection 304n and the inner side surface of the passage 204n by the anchor 30n. This deflection results in the width of the slot 102n being greater adjacent to the anchor 30n than at the opposite end of the tubular outer member 94n.

The anchor positioning push rod 386 is then withdrawn from the passage 204n in the tubular outer member 94n. Since the anchor 30n is firmly held by the anchor retainer 280n, the anchor inserter apparatus 20n can be moved from an assembly location to an operating room where the anchor inserter apparatus is to be utilized. The anchor deployment push rod 388 of FIG. 33 is moved to the operating room along with the tubular outer member 94n and the anchor 30n. However, the anchor positioning push rod 386 remains at the assembly location and is used to position another suture anchor relative to another tubular outer member.

At the operating room, the anchor deployment push rod 388 (FIG. 33) is inserted into the passage 204n in the tubular outer member 94n. Once the tubular outer member 94n and the suture anchor 30n have been positioned relative to body tissue, the anchor deployment push rod 388 is pressed against the trailing end of the anchor 30n to force the anchor out of the tubular outer member 94n into body tissue.

As the anchor deployment push rod 388 is inserted into the passage 204n in the tubular outer member 94n, the indicia 404 (FIG. 33) on the anchor deployment push rod cooperates with the end surface of the tubular outer member 94n to indicate the position of the leading end 410 of the anchor deployment push rod 388 relative to the tubular outer member 94n. Thus, the indicia 404 will indicate when the leading end 410 of the anchor deployment push rod has just moved into engagement with the trailing end of the anchor 30n while the anchor 30n is gripped by the anchor retainer 280n. Continued movement of the anchor deployment push rod into the passage 204n in the tubular outer member 94n moves the indicia 404 relative to the end surface 408 on the tubular outer member 94n. When the indicia indicates that the leading end 410 of the push rod deployment member 388 has moved the desired distance into the body tissue, the orientation of the suture anchor 30n relative to the body tissue is changed in the manner illustrated schematically in FIGS. 13–15.

In the foregoing description it has been assumed that the inner members 386 and 388 will be sequentially moved relative to the tubular outer member 94n. However, if desired, the tubular outer member 94n could be moved relative to the inner members 386 and 388. Thus, the tubular outer member 94n could be moved relative to the inner member 386 to position the anchor 30n in engagement with the suture anchor retainer 280n (FIG. 37). Similarly, the tubular outer member 94n could be moved relative to the inner member 388 to separate the suture anchor 30n from the tubular outer member.

In the foregoing description it has been assumed that the anchor 30n would be moved along the passage 204n into engagement with the anchor retainer 280n. However, the anchor 30n could be moved through the opening 208n into engagement with the anchor retainer 280n. If the anchor 30n is moved through the opening 208n into engagement with the suture anchor retainer 280n, the inner member 386 may be positioned in the passage 204n. The end surface 393 on the inner member 386 would then function as a stop to limit the extent of inward (leftward as viewed in FIG. 37) movement of the anchor relative to the tubular outer member 94n.

One specific anchor retainer 280n has been illustrated in FIG. 37. The anchor retainer 280n has the same construction as the suture anchor retainer 280g of FIGS. 24 and 25. However, it is contemplated that the anchor retainer 280n of FIG. 37 could have the same construction as anyone of the anchor retainers previously described herein.

Tubular Outer Member With Insertion Funnel

Figure 38:
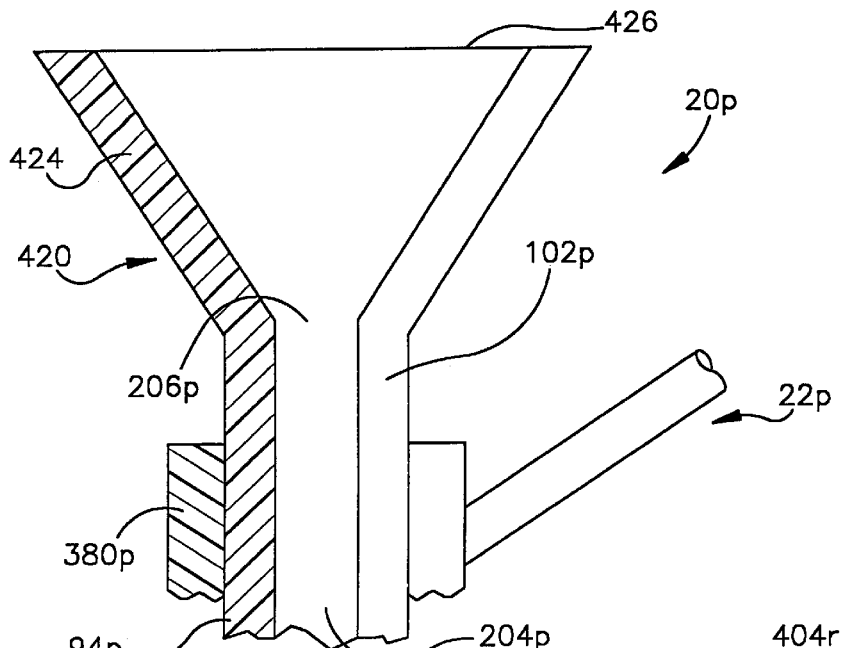
FIG. 38 is a schematic sectional view of another embodiment of the tubular outer member illustrated in FIG. 31 and illustrating an outwardly flaring or funnel-shaped end portion on the tubular outer member.

In the embodiment of the invention illustrated in FIGS. 31–37, the tubular outer member 94n has a cylindrical configuration. In the embodiment of the invention illustrated in FIG. 38, the tubular outer member has an outwardly flaring end portion to facilitate insertion of the anchor into the tubular member. Since the embodiment of the invention illustrated in FIG. 38 is generally similar to the embodiment of the invention illustrated in FIGS. 31–37, similar numerals will utilized to designate similar components, the suffix letter "p" being associated with the numerals of FIG. 38 to avoid confusion.

An anchor insertion apparatus 20p includes a tubular outer member 94p having a cylindrical central passage 204p. A slot 102p extends between opposite end portions of the tubular outer member 94p. The slot 102p also extends through a collar 380p of a handle 22p. In accordance with a feature of this embodiment of the invention, an outwardly flaring end portion or funnel 420 extends outward from the entrance opening 206p to the passage 204p. The funnel 420 has a side wall 424 with a generally conical configuration. The funnel 420 tapers from a relatively large end opening 426 to the entrance opening 206p. The slot 102p extends along the side wall 424 of the funnel 420.

When an anchor is to be moved into the passage 204p in the tubular outer member 94p, the anchor is moved into the funnel 420. A suture, which may be connected with the suture anchor, extends through the portion of the slot 102p disposed in the side wall 424 of the funnel. The anchor is moved downward (as viewed in FIG. 38) through the funnel 420 to the entrance opening 206p to the passage 204p. The funnel 420 guides this movement of the anchor and aligns the suture anchor with the passage 204p. The anchor positioning rod 386 and anchor deployment rod 388 of FIGS. 32 and 33 can be used with the anchor insertion apparatus 20p of FIG. 38.

Indexing of Inner Member

In the embodiment of the invention illustrated in FIGS. 31–37, a relatively short anchor positioning rod 386 is utilized to position an anchor relative to an anchor retainer 280n (FIGS. 36 and 37). A second inner member or deployment push rod 388 is longer than the anchor positioning push rod 386 and is used to move the anchor out of the passage 204n into body tissue. In the embodiment of the invention illustrated in FIGS. 39 and 40, the same inner member is used to position the anchor relative to an anchor retainer and to move the anchor into body tissue. Since the embodiment of the invention illustrated in FIGS. 39 and 40 is generally similar to the embodiment of the invention illustrated in FIGS. 1–38, similar numerals will be utilized to designate similar components, the suffix letter "r" being associated with the numerals of FIGS. 39 and 40 to avoid confusion.

A anchor inserter apparatus 20r includes a cylindrical inner member 92r and a cylindrical tubular outer member 94r. The outer member 94r has the same construction as the outer member 94n of FIG. 31. The outer member 94r has a slot 102r which extends between the circular entrance opening 206r and an exit opening (not shown) corresponding to the exit opening 208n of FIG. 31.

A handle 22r is connected with the end portion of the tubular outer member 94r adjacent to the entrance opening 206r. An anchor retainer (not shown) is disposed adjacent to the exit opening from the tubular outer member 94r. The anchor retainer connected with the tubular outer member 94r has the same construction as illustrated in FIGS. 24, 25, 31 and 37.

Figure 39:
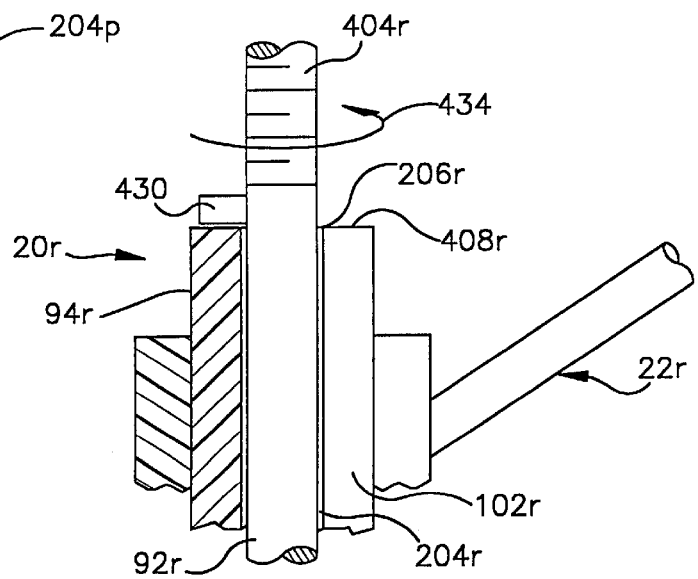
FIG. 39 is a schematic sectional view of another embodiment of the invention and illustrating the manner in which a stop element connected with an inner member engages an end portion of a tubular outer member having a construction similar to the construction of the tubular outer member of FIG. 31.
Figure 40:
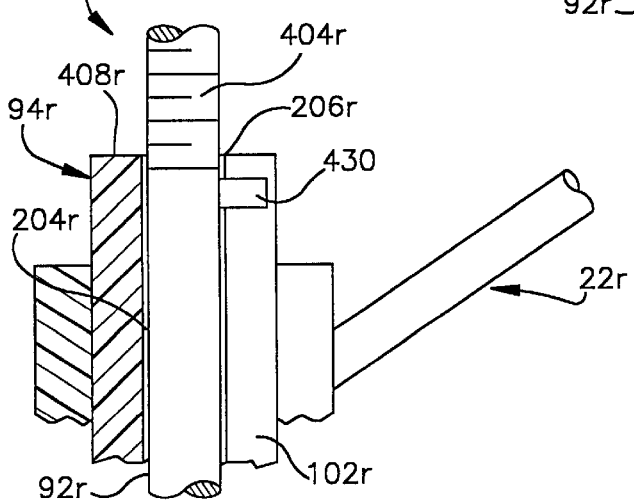
FIG. 40 is a schematic sectional view illustrating the manner in which the stop element moves along a slot in the tubular outer member of FIG. 39 during insertion of an anchor into body tissue.

In accordance with a feature of the embodiment of the invention illustrated in FIGS. 39 and 40, a stop or index pin 430 is connected with the inner member 92r. When the inner member 92r has moved an anchor to a predetermined position relative to an anchor retainer connected with the tubular outer member 94r, in the manner illustrated in FIG. 37 for the anchor 30n, the stop member 430 engages an annular end or stop surface 408r on the tubular outer member 94r (FIG. 39). At this time, the leading end of the inner member 92r is disposed adjacent to an anchor retainer (not shown) connected with the outer end portion of the tubular outer member 94r to position the anchor for engagement by the anchor retainer.

In the embodiment of the invention illustrated in FIGS. 39 and 40, the anchor retainer has the same construction as the anchor retainer 280n of FIG. 37. However, it is contemplated that the anchor retainer could have a construction which is the same as the construction of any one of the anchor retainers illustrated in FIGS. 19–30. Engagement of the stop member 430 with the end surface 408r on the tubular outer member 94r limits telescopic movement of the inner member 92r relative to the tubular outer member 94r. Therefore, the anchor is positioned with a leading end portion of the anchor extending from the tubular outer member 94r and a trailing end portion of the anchor disposed in a passage 204r formed in the tubular outer member 94r. At this time, the trailing end portion of the anchor is gripped by the anchor retainer.

When the anchor is to be positioned relative to body tissue, the inner member 92r is rotated about its longitudinal central axis relative to the tubular outer member 94r, in the manner indicated schematically by an arrow 434 in FIG. 39. As the inner member 92r rotates about the longitudinal central axis of the passage 204r, the stop member 430 is moved into alignment with the slot 102r in the tubular outer member 94r.

To disengage the anchor from the anchor retainer and to move the trailing end portion of the anchor from the passage 204r into body tissue, the inner member 92r is moved along coincident longitudinal central axes of the inner member and the outer member 94r. As this occurs, the stop member 430 moves into the slot 102r (FIG. 40). As the stop member 430 moves along the slot 102r, the inner member 92r applies force against the trailing end portion of the anchor to move the anchor out of the tubular outer member 94r in the manner previously explained in conjunction with the embodiments of the invention illustrated in FIGS. 11–37.

As the inner member 92r is telescopically moved into the outer member 94r, indicia 404r cooperates with the end surface 408r (FIG. 40) to indicate the position of the leading end of the inner member 92r and the anchor relative to the leading end of the outer member 94r. When the indicia 404r indicates that the inner member 92r and anchor have been moved through a desired distance relative to the outer member 94r, the orientation of the anchor is changed relative to the body tissue in the manner illustrated schematically in FIGS. 13–15 for the suture anchor 30c.

Index Recess

In the embodiment of the invention illustrated in FIGS. 39 and 40, the stop member 430 is moved along the slot 102r which extends between opposite ends of the tubular outer member 94r. In the embodiment of the invention illustrated in FIG. 41, an index recess is provided to receive the stop member. Since the embodiment of the invention illustrated in FIG. 41 is generally similar to the embodiment of the invention illustrated in FIGS. 39 and 40, similar numerals will be utilized to designate similar components, the suffix letter "s" being associated with the numerals of FIG. 41 to avoid confusion.

A cylindrical inner member 92s is telescopically received in a passage 204s formed in a cylindrical tubular outer member 94s. A handle 22s is connected with the tubular outer member 94s. The inner member 92s is movable axially along the passage 204s in the tubular outer member 94s until a cylindrical stop member 430s engages an annular stop surface 408s on the tubular outer member 94s.

Engagement of the stop member 430s with the stop surface 408s occurs when the suture anchor has been moved to a position relative to the tubular outer member 94s in which a leading end portion of the suture anchor extends outward from the tubular outer member and a trailing end portion of the suture anchor is disposed in the passage 204s. At this time, an anchor retainer having a construction similar to the construction of any one of the suture retainers illustrated in FIGS. 19–28 engages the anchor to hold it in a predetermined position relative to the tubular outer member 94s. It is believed that it may be desired to utilize an anchor retainer having the same construction as the suture anchor retainer 280n of FIGS. 31 and 37.

Figure 41:
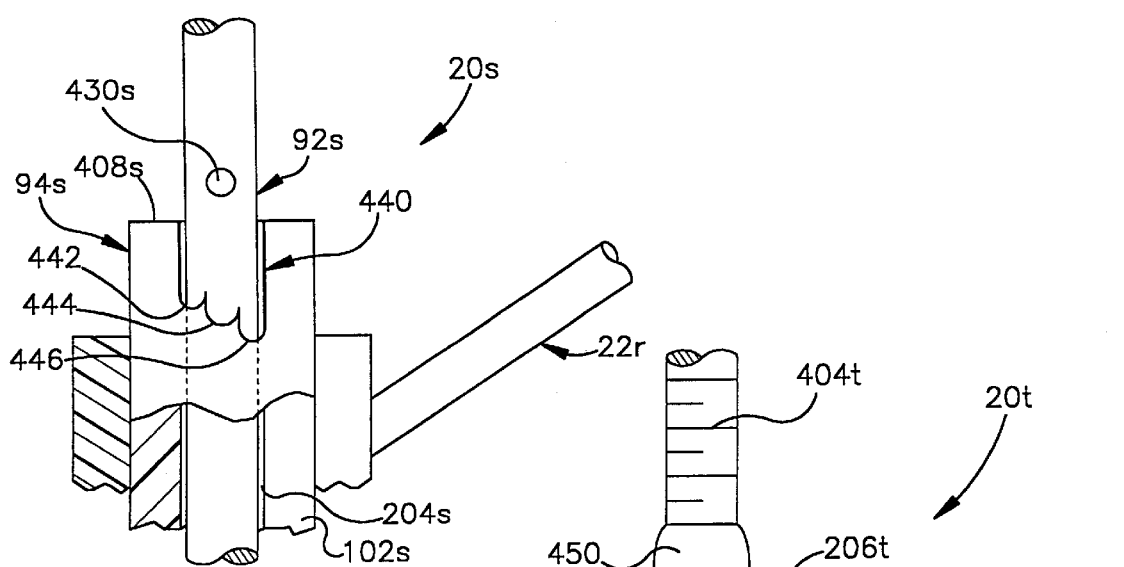
FIG. 41 is a schematic sectional view of another embodiment of the invention and illustrating the relationship between a stop element on an inner member and index recess formed in a tubular outer member having a construction similar to the construction of the tubular outer member of FIG. 31.

In accordance with a feature of the embodiment of the invention illustrated in FIG. 41, an index recess 440 is provided in the tubular outer member 94s to receive the stop member 430. The index recess 440 is provided with a plurality of index surfaces 442, 444, and 446 which correspond to different depths of insertion of an anchor into body tissue. Thus, when the anchor is to be inserted a relatively short distance into the body tissue, the stop member 430s is moved into engagement with the index surface 442 to limit relative movement of the inner member 92s relative to the tubular outer member 94s. If the anchor is to be inserted further into the body tissue, the stop member 430s is moved into engagement with the index surface 444. If the anchor is to be inserted still further into the body tissue, the stop member 430s is moved into engagement with the index surface 446.

The index recess 440 enables the stop member 430s to move to a desired position relative to the tubular outer member 94s without moving along the slot 102s formed in the tubular outer member 94s. In addition, the index recess 440 enables the depth of insertion of an anchor into body tissue to be controlled by engagement of the stop member 430s with any one of the index surfaces 442, 444 or 446.

In the illustrated embodiment of the invention, the index surfaces 442, 444 and 446 are disposed in a single index recess. However, the index surfaces 442, 444 and 446 could be disposed in a plurality of index recesses. Thus, a plurality of different length slots could be formed in the tubular outer member 94s with a different index surface at the end of each slot.

Deflectable Stop Member

In the embodiment of the invention illustrated in FIGS. 39–41, a stop member 430r or 430s is fixedly connected with an inner member. In the embodiment of the invention illustrated in FIG. 42, a stop member is yieldable relative to the inner member. Since the embodiment of the invention illustrated in FIG. 42 is generally similar to the embodiment of the invention illustrated in FIGS. 1–41, similar numerals will be utilized to designate similar components, the suffix letter "s" being associated with the numerals of FIG. 42 to avoid confusion.

A generally cylindrical inner member 92t is received in a passage 204t formed in a cylindrical tubular outer member 94t. A handle 22t is connected with the tubular outer member 94t. A slot 102t extends between openings at opposite ends of the tubular outer member 94t. An anchor retainer (not shown) is disposed adjacent to the leading end of the tubular outer member 94t.

Figure 42:
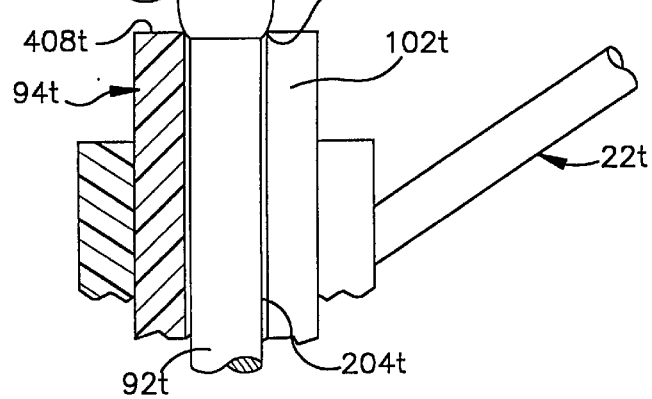
FIG. 42 is a schematic sectional view of another embodiment of the invention, and illustrating the manner in which a resiliently deflectable stop element on an inner member engages an end of a tubular outer member having a construction similar to the construction of the tubular outer member of FIG. 31.

In accordance with a feature of the embodiment of the invention illustrated in FIG. 42, a resiliently deflectable stop 450 is connected with the inner member 92t. The stop 450 is engageable with the entrance opening 206t to limit axial movement of the inner member 92t relative to the outer member 94t in the manner illustrated in FIG. 42. The stop 450 is formed of a resiliently deflectable material which, when axial force is applied against the inner member 92t, is deflected radially inward and enters the passage 204t in the tubular outer member 92t. As this occurs, the inner member 92t moves the suture anchor out of engagement with a suture anchor retainer (not shown) and into body tissue.

Suitable indicia 404t is provided on the inner member 92t. The indicia 404t cooperates with an end surface 408t on the tubular outer member 94t to indicate the position of the inner member 92t relative to the tubular outer member 94t and the body tissue.

Forming of Opening in Body Tissue

When the anchor is to be positioned in hard body tissue, in a manner similar to that illustrated in FIGS. 13–15, a recess or opening is formed in the hard body tissue to receive the suture anchor. Since components of the embodiment of the invention illustrated in FIG. 43 are the same as components of the embodiments of the invention illustrated in FIGS. 1–42, similar numerals will be utilized to identify similar components, the suffix letter "u" being added to the numerals of FIG. 43 to avoid confusion.

Figure 43:
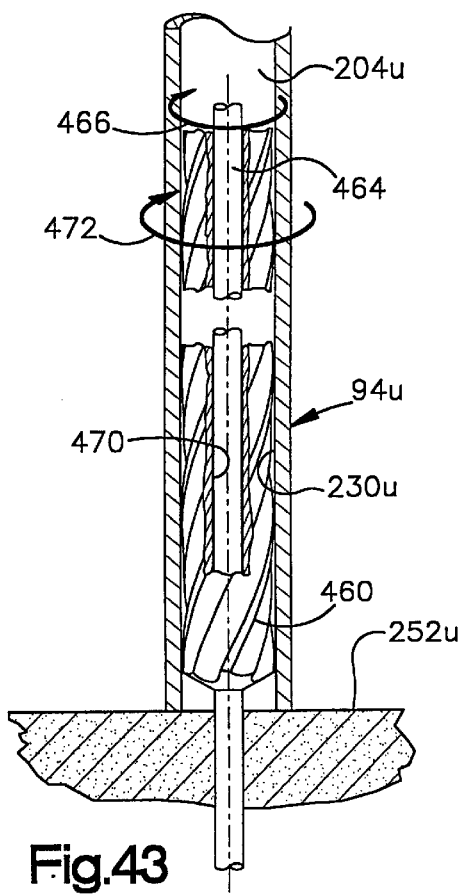
FIG. 43 is a fragmentary schematic sectional view depicting the manner in which a tubular outer member having the same general construction as the tubular outer member of the embodiment of the invention illustrated in FIG. 11, is utilized in association with a thin elongated member to guide movement of a drill relative to body tissue.

In accordance with a feature of the embodiment of the invention illustrated in FIG. 43, the tubular outer member 94u is used to guide movement of a cutting tool, such as a drill 460 relative, to hard body tissue or bone 252u. Thus, the tubular outer member 94u is used for the purpose of guiding movement of the cutting tool. The tubular outer member 94u is also used to guide movement of an inner member and anchor, such as the inner member 92c and anchor 30c of FIG. 11.

When a recess or opening, corresponding to the opening 250 of FIG. 13, is to be formed in the bone 252u (FIG. 43), a thin elongated member 464 is rotated about its central axis, in the manner indicated schematically by an arrow 466 in FIG. 43, by a suitable drill mechanism. As this occurs, the thin elongated member or K-wire 464 is moved axially into the bone. After the thin elongated member 464 has been moved to a desired depth into the bone, the tubular outer member 94u of an anchor inserter apparatus having the same construction as the anchor inserter apparatus 20c of FIG. 11, is axially positioned around the thin elongated member 464.

The drill 460 has a central passage 470 which enables the drill to be slid onto the thin elongated member 464. The tubular outer member 94t is then positioned around the drill and moved into engagement with the bone 252u in the manner illustrated in FIG. 43. The drill 460 is then rotated about the coincident longitudinal central axes of the thin elongated member 464 and the tubular outer member 94u in the manner indicated schematically by an arrow 472 in FIG. 43.

As the drill is rotated, in the manner indicated by the arrow 472 in FIG. 43, the drill is moved axially relative to the stationary thin elongated member 464 and to the stationary tubular outer member 94u. This axial movement of the drill slides the drill along the cylindrical outer side surface of the thin elongated member 464 and along an inner side surface 230u of the tubular outer member. As this occurs, the drill forms an opening in the bone 252u.

Indicia (not shown) may be provided on the drill. This indicia cooperates with the end of the tubular outer member 94u to indicate the depth to which the drill has moved into the bone 252u. The indicia on the drill cooperates with an end surface (not shown) on the tubular outer member 94u in the same manner as in which the indicia 404 (FIG. 33) on the inner member 388 cooperates with the end surface 408 on the tubular outer member. If desired, a stop could be connected with the drill 460 (FIG. 43) and moved into engagement with the end surface on the tubular outer member to limit axial movement of the drill into the bone 252u.

When the drill 460 (FIG. 43) has moved to a desired depth in the bone 252u, the drill is axially withdrawn from the thin elongated member. The thin elongated member extends further into the bone 252u than the distance which the drill enters the bone. Therefore, the thin elongated member 464 remains in place as the drill 460 is withdrawn from the thin elongated member.

The tubular outer member 94t is maintained stationary relative to the bone 252u as the drill 460 is withdrawn from the thin elongated member. The orientation of both the thin elongated member 464 and the tubular outer member 94t are maintained constant relative to the bone 252u after the drill has been withdrawn from the passage 204u in the tubular outer member 94u. The tubular outer member 94u may be held stationary relative to the bone 252u by clamping the portion of the patient containing the bone to a base plate and by fixedly connecting the tubular outer member 94t with the base plate.

Once the opening has been drilled to the desired depth in the bone 252t and the drill 460 disengaged from the thin elongated member 464 and tubular outer member 94t, the anchor is moved along the thin elongated member 464 into the tubular outer member 94u. This results in the anchor being guided into the opening formed in the bone 252u by the thin elongated member. The anchor is moved into the opening formed in the bone by movement of a tubular inner member, corresponding to the inner member 92c of FIG. 11, axially along the thin elongated member and into the tubular outer member 94u.

Conclusion

The present invention relates to a new and improved method and apparatus 20 (FIGS. 1–43) for use in positioning an anchor 30 during assembly of the apparatus. The invention also relates to a new and improved apparatus 20 (FIGS. 1–43) for use in positioning an anchor 30 relative to body tissue during use of the apparatus. The apparatus 20 includes a tubular outer member 94 and an inner member 92 which is received in a passage 204 in the tubular outer member.

A slot 102 may extend between openings 206 and 208 at opposite ends of the tubular outer member 94. During positioning of the anchor 30 relative to body tissue 88 or 252, the slot 102 facilitates visualization of the anchor by a surgeon. Stop surfaces 396, 410, and 430 may be provided in association with the inner and outer members 92 and 94 to facilitate moving the anchor 30 to a desired position relative to the inner and outer members during relative movement between the inner and outer members.

In addition, the apparatus 20 may includes a retainer 280 which holds an anchor 30 in a desired position relative to the apparatus during assembly of the apparatus and during positioning of the anchor relative to body tissue. The retainer 280 is deflected under the influence of force applied against the retainer by the anchor 30 to enable the retainer to grip the anchor and hold the suture anchor in the desired position.

The retainer 280 may engage a recess 300, 236, or 238 in the anchor 30. The recess may be formed by a passage in the anchor. Alternatively, the recess may be formed in an outer side surface of the anchor.

During positioning of the anchor 30 relative to body tissue 88 or 252, the tubular outer member 94 may be utilized as a guide for a drill 460 which forms an opening in the body tissue. After the opening has been formed in the body tissue, the drill 460 is removed from the tubular outer member 94 and the anchor 30 is moved along the tubular outer member 94 into the body tissue.

Having described the invention, the following is claimed:

1. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means.

2. An apparatus as set forth in claim 1 wherein said tubular member includes a side wall having surfaces which at least partially define a slot which extends away from an open end of the passage in the tubular member, said positioner means being connected with a portion of said one of said inner and tubular members opposite from the slot.

3. An apparatus as set forth in claim 1 further including indicia disposed on said inner member adjacent to said tubular member, said indicia on said inner member cooperates with said tubular member to indicate the position of said inner member relative to said tubular member.

4. An apparatus as set forth in claim 1 further including a handle fixedly connected with said tubular member, said inner member being movable along the passage in said tubular member to effect separation of the trailing end portion of the anchor from said tubular member, said positioner means being connected with said tubular member.

5. An apparatus comprising an anchor having a recess, a tubular outer member having a passage in which at least a trailing end portion of said anchor is received, an anchor positioner connected with said tubular outer member, said anchor positioner being engageable with the recess in said anchor to position said anchor relative to said tubular outer member with the trailing end portion of said anchor in the passage in said tubular outer member, and an inner member disposed in the passage in said tubular outer member, said inner member and said tubular outer member being movable relative to each other to disengage said anchor positioner from the recess in said anchor and to separate the trailing end portion of said anchor from the passage in said tubular outer member during positioning of said anchor in body tissue.

6. An apparatus as set forth in claim 5 wherein said anchor has a passage which extends transversely to a longitudinal central axis of said suture anchor, said recess in said anchor being at least partially formed by a portion of said passage in said anchor.

7. An apparatus as set forth in claim 5 wherein said recess in said anchor is formed as a groove which extends completely around said anchor.

8. An apparatus as set forth in claim 5 wherein said anchor has a cylindrical outer side surface and said recess in said anchor has an annular configuration and projects radially inward from said cylindrical outer side surface on said anchor.

9. An apparatus as set forth in claim 5 wherein said anchor has a first portion which is disposed on one side of said anchor and is engaged by said anchor positioner, said recess in said anchor being at least partially disposed in said first portion of said anchor, said anchor having a second portion which is disposed on a side of said anchor opposite from said one side and is at least partially pressed against an inner side of the passage in said tubular outer member by said anchor positioner.

10. An apparatus as set forth in claim 5 wherein said anchor positioner is resiliently deflectable from a first position to a second position by engagement of an end portion of said anchor with said anchor positioner, said anchor positioner being resiliently deflectable from the second position toward the first position upon engagement of said anchor positioner with the recess in said anchor.

11. An apparatus as set forth in claim 5 wherein said recess in said anchor is formed as a ring which extends around said anchor, said anchor positioner being formed as a ring which engages said recess in said anchor when said anchor is disposed in a predetermined position relative to said tubular outer member.

12. An apparatus as set forth in claim 5 wherein said tubular outer member includes a slot which extends from said one end of said tubular outer member toward an opposite end of said tubular outer member.

13. An apparatus as set forth in claim 12 wherein said anchor positioner is integrally formed as one piece with said tubular member and is disposed on a portion of said tubular outer member opposite from said slot.

14. An apparatus as set forth in claim 5 wherein said tubular outer member is axially movable along an outer side surface on said inner member to disengage said anchor positioner from said recess in said anchor and to separate the trailing end portion of said anchor from the passage in said tubular outer member.

15. An apparatus as set forth in claim 5 wherein said inner member is axially movable along an inner side surface on said tubular outer member to disengage said anchor positioner from said recess in said anchor and to separate the trailing end portion of said anchor from the passage in said tubular outer member.

16. An apparatus for use in positioning an anchor relative to body tissue, said apparatus comprising a tubular outer member having a passage in which at least a trailing end portion of the anchor is received, said passage extends from an opening at one end portion of said tubular outer member toward another end portion of said tubular outer member, and an inner member at least partially disposed in the passage in said tubular outer member, said tubular outer member and said inner member being movable relative to each other to separate the trailing end portion of the anchor from the passage in said tubular outer member, at least a portion of said one end portion of said tubular outer member being resiliently deflectable from a first condition to a second condition under the influence of force applied against said one end portion of said tubular outer member by the anchor, said one end portion of said tubular outer member being effective to apply force against the anchor to retain the trailing end portion of the anchor in the passage in said tubular outer member when said tubular outer member is in the second condition, said inner member and said tubular outer member being movable relative to each other to separate the trailing end portion of the anchor from the passage in said tubular outer member.

17. An apparatus as set forth in claim 16 wherein said tubular outer member includes a slot which extends from the opening at the one end portion of said tubular outer member to an opening at the other end portion of the tubular outer member.

18. An apparatus as set forth in claim 16 wherein said inner member is effective to apply force to the anchor to effect movement of the anchor relative to said tubular outer member to deflect said one end portion of said tubular outer member from the first condition to the second condition during relative movement between said tubular outer member and said inner member.

19. An apparatus as set forth in claim 16 wherein at least a portion of the passage in said tubular outer member has a first cross sectional area when said one end portion of said tubular outer member is in the first condition and has a second cross sectional area when said one end portion of said tubular outer member is in the second condition, said second cross sectional area being greater than said first cross sectional area.

20. An apparatus as set forth in claim 16 wherein said tubular outer member includes a slot which extends from the opening at the one end portion of said tubular outer member toward the other end portion of said tubular outer member, at least a portion of the slot in said tubular outer member has a first width when said tubular outer member is in the first condition and has a second width which is larger than the first width when said tubular outer member is in the second condition.

21. An apparatus as set forth in claim 16 wherein said end portion of said tubular outer member has an inner surface area which grips a portion of the anchor to hold the anchor when said one end portion of said tubular outer member is in the second condition.

22. An apparatus as set forth in claim 16 wherein said inner member includes a surface which engages said tubular outer member to block relative movement between said inner member and said tubular outer member when the one end portion of said tubular outer member is in the second condition with the trailing end portion of the anchor in the passage in said tubular outer member and a leading end portion of the anchor extends outward from the one end portion of said tubular outer member.

23. An apparatus as set forth in claim 16 wherein said one end portion of said tubular outer member includes an inner side surface and a projection which extends from said inner side surface toward the longitudinal central axis of said tubular outer member, said projection being disposed in engagement with an outer side surface of the anchor when said one end portion of said tubular outer member is in the second condition.

24. An apparatus as set forth in claim 16 wherein said one end portion of said tubular outer member includes an inner side surface and a projection which extends from said inner side surface toward the longitudinal central axis of said tubular outer member, said projection having surface means for engaging a recess formed in the anchor when said one end portion of said tubular outer member is in the second condition.

25. An apparatus as set forth in claim 16 further including indicia disposed on said inner member adjacent to the other end portion of said tubular outer member, said indicia on said inner member cooperates with the other end portion of said tubular outer member to indicate the position of a leading end portion of said inner member relative to the one end portion of said tubular outer member.

26. An apparatus as set forth in claim 16 wherein said tubular outer member is slidable along an outer side surface on said inner member to separate the trailing end portion of the anchor from the passage in said tubular outer member.

27. An apparatus as set forth in claim 16 wherein said inner member is slidable along an inner side surface of said tubular outer member to separate the trailing end portion of the anchor from the passage in said tubular outer member.

28. A method of positioning an anchor relative to body tissue, said method comprising the steps of guiding movement of a drill relative to the body tissue by moving the drill along a passage in a tubular member during formation of an opening in the body tissue with the drill, removing the drill from the body tissue and the tubular member, inserting the anchor into the passage in the tubular member, and moving the anchor along the passage in the tubular member into the opening in the body tissue.

29. A method as set forth in claim 28 further including the steps of maintaining the tubular member in a first orientation relative to the body tissue during movement of the drill along the passage in the tubular member, and maintaining the tubular member in the first orientation relative to the body tissue during movement of the anchor along the passage in the tubular member into the opening in the body tissue.

30. A method as set forth in claim 28 further including the step of moving a thin elongated member into the body tissue, said step of guiding movement of the drill relative to the body tissue includes inserting the thin elongated member into a passage in the drill and moving the drill along the thin elongated member simultaneously with movement of the drill along the passage in the tubular member.

31. A method as set forth in claim 28 wherein said step of moving the drill along a passage in a tubular member includes moving indicia on the drill relative to the tubular member and interrupting movement of the drill along the passage in the tubular member when the indicia is in a predetermined position relative to the tubular member.

32. A method comprising the steps of providing a tubular member having a passage which extends between first and second end portions of the tubular member, moving an anchor along the passage in the tubular member in a direction away from the first end portion of the tubular member, resiliently deflecting at least a portion of the second end portion of the tubular member under the influence of force transmitted from the anchor to the second end portion of the tubular member, and retaining the anchor against movement relative to the second end portion of the tubular member under the influence of force transmitted from the resiliently deflected portion of the second end portion of the tubular member to the anchor.

33. A method as set forth in claim 32 wherein said step of retaining the anchor against movement relative to the second end portion of the tubular member is performed with a trailing end portion of the anchor in the passage in the tubular member and with a leading end portion of the suture anchor extending outward from the second end portion of the tubular member.

34. A method as set forth in claim 32 further including the step of interrupting movement of the anchor along the passage in the tubular member when the anchor is in a predetermined position relative to the tubular member, said step of resiliently deflecting at least a portion of the second end portion of the tubular member is performed prior to performance of said step of interrupting movement of the suture anchor along the passage in the tubular member.

35. A method as set forth in claim 32 wherein the second end portion of the tubular member includes a slot which extends from an opening in the second end portion of the tubular member toward the first end portion of the tubular member, said step of resiliently deflecting the second end portion of the tubular member includes expanding at least a portion of the slot.

36. A method as set forth in claim 32 wherein said step of resiliently deflecting at least a portion of the second end portion of the tubular member includes engaging a projection which extends inward from an inner side surface of the tubular member toward a longitudinal central axis of the tubular member with a leading end portion of the anchor and moving the projection outward away from the longitudinal central axis of the tubular member.

37. A method as set forth in claim 32 wherein said step of resiliently deflecting at least a portion of the second end portion of the tubular member includes engaging an inner side surface of the tubular member which at least partially defines the passage in the tubular member with a leading end portion of the anchor and moving a portion of the inner side surface of the tubular member outward away from a longitudinal central axis of the tubular member.

38. A method as set forth in claim 32 wherein said steps of moving the anchor along the passage in the tubular member and resiliently deflecting at least a portion of the tubular member include applying force against a trailing end portion of the anchor with a leading end portion of a pusher member and applying force against the tubular member with a leading end portion of the anchor.

39. A method as set forth in claim 32 wherein said step of retaining the anchor against movement relative to the second end portion of the tubular member includes applying force against one side of the anchor and pressing a side of the anchor opposite from the one side against an inner side surface on the tubular member.

40. A method as set forth in claim 32 further including the steps of moving at least a leading end portion of a first pusher member into the passage in the tubular member, said step of deflecting the second end portion of the tubular member under the influence of force transmitted from the anchor to the second end portion of the tubular member includes transmitting force from the leading end portion of the first pusher member to a trailing end portion of the anchor, moving the first pusher member out of the passage in the tubular member, moving at least a leading end portion of a second pusher member into the passage in the tubular member, and moving at least the trailing end portion of the anchor from the passage in the tubular member by transmitting force from the leading end portion of the second pusher member to the trailing end portion of the anchor.

41. A method as set forth in claim 32 wherein a recess is formed in the anchor, said step of retaining the anchor against movement relative to the second end portion of the tubular member includes engaging the recess with the second end portion of the tubular member.

42. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, and, thereafter, holding the anchor against movement relative to the tubular member under the influence of force transmitted from the end portion of the tubular member to the anchor.

43. A method as set forth in claim 42 wherein said step of expanding the end portion of the tubular member includes expanding the end portion of the tubular member from a first condition to a second condition, the portion of the passage in the end portion of the tubular member has a first cross sectional area in a plane extending perpendicular to a longitudinal central axis of the tubular member when the end portion of the tubular member is in the first condition, the portion of the passage in the end portion of the tubular member has a second cross sectional area in a plane extending perpendicular to the longitudinal central axis of the tubular member when the end portion of the tubular member is in the second condition, said second cross sectional area being greater than said first cross sectional area.

44. A method as set forth in claim 42 wherein said step of moving the anchor into a portion of the passage in an end portion of the tubular member includes applying force against a trailing end portion of the anchor and moving the anchor along the passage in the tubular member, said step of expanding the end portion of the tubular member includes transmitting force from the trailing end portion of the anchor through a leading end portion of the anchor to the end portion of the tubular member.

45. A method as set forth in claim 42 wherein said step of holding the anchor against movement relative to the tubular member is performed with one end portion of the anchor in the passage in the tubular member and with another end portion of the anchor extending outward from the end portion of the tubular member.

46. A method as set forth in claim 42 wherein said step of expanding the end portion of the tubular member includes resiliently deflecting at least a portion of the end portion of the tubular member.

47. A method as set forth in claim 42 wherein the end portion of the tubular member includes a slot which extends from an opening in the second end portion of the tubular member toward an opposite end portion of the tubular member, said step of expanding the end portion of the tubular member includes increasing a distance between opposite sides of at least a portion of the slot.

48. A method of positioning an anchor for engagement with body tissue, said method comprising the steps of providing a member having a passage which tapers from a first portion having a first cross sectional area in a plane perpendicular to a central axis of the passage to a second portion having a second cross sectional area in a plane perpendicular to the central axis of the passage, the second cross sectional area being smaller than the fist cross sectional area, moving the anchor into the second portion of the passage and increasing the cross sectional area of the second portion of the passage from the second cross sectional area to a cross sectional area which is greater than the second cross sectional area during performance of said step of moving the anchor into the second portion of the passage.

49. A method as set forth in claim 48 wherein said step of increasing the cross sectional area of the second portion of the passage from the second cross sectional area is performed during performance of said step of moving the anchor into the second portion of the passage.

50. A method as set forth in claim 48 wherein said step of increasing the cross sectional area of the second portion of the passage includes moving a leading end portion of the anchor from the first portion of the passage to the second portion of the passage.

51. A method as set forth in claim 48 further including the step of gripping the anchor with an inner side surface area disposed on the second portion of the passage to retain the anchor against movement relative to the member.

52. A method as set forth in claim 48 wherein the member includes a slot which has a first width when the second portion of the passage has the second cross sectional area, said step of increasing the cross sectional area of the second portion of the passage includes increasing the width of at least a portion of the slot from the first width to a second width which is greater than the first width.

53. A method of positioning an anchor for engagement with body tissue, said method comprising the steps of providing a tubular member having a passage which has a first end portion disposed in a first end portion of the tubular member and a second end portion disposed in a second end portion of the tubular member, moving an anchor into the first end portion of the passage in the tubular member through an opening in the first end portion of the tubular member, applying force against a trailing end portion of the anchor with a pusher member to move the anchor along the passage in the tubular member, and expanding the second end portion of the passage under the influence of force transmitted from the pusher member through a leading end portion of the anchor to the second end portion of the tubular member during movement of the anchor along the passage in the tubular member.

54. A method as set forth in claim 53 wherein said step of applying force against a trailing end portion of the anchor with a pusher member to move the anchor along the passage in the tubular member includes moving the pusher member relative to the tubular member.

55. A method as set forth in claim 53 wherein said step of applying force against a trailing end portion of the anchor with a pusher member to move the anchor the passage in the tubular member includes moving the tubular member relative to the pusher member.

56. A method as set forth in claim 53 wherein said step of expanding the second end portion of the passage includes deflecting at least a portion of the second end portion of the tubular member outward in a direction away from a longitudinal central axis of the tubular member.

57. A method as set forth in claim 53 wherein said step of applying force against a trailing end portion of the anchor with a pusher member to move the anchor along the passage in the tubular member includes moving a surface connected with the pusher member and a surface connected with the tubular member into engagement to block relative movement between the pusher member and tubular member when the anchor is in a predetermined position relative to the tubular member.

58. A method as set forth in claim 57 wherein a slot extends between the first and second end portions of the tubular member, said method further includes the step of rotating the pusher member relative to the tubular member to move the surface on the pusher member into alignment with the slot, and, thereafter, applying force against the trailing end portion of the anchor with the pusher member to move the anchor away from the predetermined position, said step of applying force against the trailing end portion of the anchor with the pusher member to move the anchor away from the predetermined position includes moving the surface connected with the pusher member along the slot in the tubular member.

59. A method as set forth in claim 58 wherein said step of expanding the second end portion of the passage includes increasing the width of a portion of the slot disposed in the second end portion of the tubular member.

60. A method as set forth in claim 53 further including the step of removing the pusher member from the passage in the tubular member with at least a portion of the anchor in the passage in the tubular member, applying force against the trailing end portion of the anchor with a second pusher member to move the anchor out of the passage in the tubular member.

61. A method as set forth in claim 53 further including the step of gripping the anchor with the second end portion of the tubular member during performance of said step of expanding the second end portion of the passage.

62. A method as set forth in claim 53 further including the step of engaging a recess in the anchor with the second portion of the tubular member to hold the anchor against movement relative to the tubular member.

63. A method as set forth in claim 53 wherein said step of expanding the second end portion of the tubular member includes resiliently deflecting at least a portion of the second end portion of the tubular member under the influence of force-transmitted from the anchor.

64. A method as set forth in claim 53 wherein the second end portion of the tubular member includes a slot, said step of expanding the second end portion of the tubular member includes increasing the width of at least a portion of the slot.

65. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, said positioner means includes a surface area which is integrally formed as one piece with said one of said inner and tubular members and projects into the opening in the anchor.

66. An apparatus as set forth in claim 65 wherein said tubular member includes a side wall having surfaces which at least partially define a slot which extends away from an open end of the passage in the tubular member, said positioner means being connected with a portion of said one of said inner and tubular members opposite from the slot.

67. An apparatus as set forth in claim 66 wherein said positioner means includes a projection which extends towards the slot, said projection being movable away from the slot under the influence of force transmitted through the anchor to said projection upon relative movement between said tubular member and said inner member.

68. An apparatus as set forth in claim 66 wherein said tubular member is resiliently deflectable from a first condition in which the slot has a first width and said positioner means is effective to engage the opening in the suture anchor to retain at least a portion of the suture anchor in the passage in said tubular member to a second condition in which the slot has a second width and said positioner means is ineffective to engage the opening in the anchor to retain the anchor in the passage in said tubular member, said second width of the slot being greater than said first width of the slot.

69. An apparatus as set forth in claim 66 further including indicia disposed on said inner member adjacent to said tubular member, said indicia on said inner member cooperates with said tubular member to indicate the position of said inner member relative to said tubular member.

70. An apparatus as set forth in claim 66 further including a handle fixedly connected with said inner member, said tubular member being movable along said inner member to effect separation of the trailing end portion of the anchor from said tubular member.

71. An apparatus as set forth in claim 66 further including a handle fixedly connected with said tubular member, said inner member being movable along the passage in said tubular member to effect separation of the trailing end portion of the anchor from said tubular member, said positioner means being connected with said tubular member.

72. An apparatus as set forth in claim 65 wherein the anchor further includes a surface which is engagable by a suture to interconnect the anchor and the suture.

73. An apparatus as set forth in claim 65 wherein a suture extends into the opening in the anchor, said surface area of said positioner means being engagable with the suture.

74. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, said tubular member includes a side wall having surfaces which at least partially define a slot which extends away from an open end of the passage in the tubular member, said positioner means being connected with a portion of said one of said inner and tubular members opposite from the slot, said positioner means includes a projection which extends towards the slot, said projection being movable away from the slot under the influence of force transmitted through the anchor to said projection upon relative movement between said tubular member and said inner member.

75. An apparatus as set forth in claim 74 further including indicia disposed on said inner member adjacent to said tubular member, said indicia on said inner member cooperates with said tubular member to indicate the position of said inner member relative to said tubular member.

76. An apparatus as set forth in claim 74 wherein said positioner means includes a spring which engages the opening in the anchor, said projection being disposed on said spring.

77. An apparatus as set forth in claim 74 wherein said projection applies force against the anchor to press the anchor against a portion of said one of said inner and tubular members.

78. An apparatus as set forth in claim 74 further including a handle fixedly connected with said inner member, said tubular member being movable along said inner member to effect separation of the trailing end portion of the anchor from said tubular member.

79. An apparatus as set forth in claim 74 further including a handle fixedly connected with said tubular member, said inner member being movable along the passage in said tubular member to effect separation of the trailing end portion of the anchor from said tubular member, said positioner means being connected with said tubular member.

80. An apparatus as set forth in claim 74 wherein the anchor further includes a surface which is engagable by a suture to interconnect the anchor and the suture.

81. An apparatus as set forth in claim 74 wherein a suture is connected with the anchor and is at least partially disposed in the slot in said tubular member.

82. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, said tubular member includes a side wall having surfaces which at least partially define a slot which extends away from an open end of the passage in the tubular member, said positioner means being connected with a portion of said one of said inner and tubular members opposite from the slot, said tubular member is resiliently deflectable from a first condition in which the slot has a first width and said positioner means is effective to engage the opening in the anchor to retain at least a portion of the anchor in the passage in said tubular member to a second condition in which the slot has a second width and said positioner means is ineffective to engage the opening in the anchor to retain the anchor in the passage in said tubular member, said second width of the slot being greater than said first width of the slot.

83. An apparatus as set forth in claim 82 further including indicia disposed on said inner member adjacent to said tubular member, said indicia on said inner member cooperates with said tubular member to indicate the position of said inner member relative to said tubular member.

84. An apparatus as set forth in claim 82 further including a handle fixedly connected with said inner member, said tubular member being movable along said inner member to effect separation of the trailing end portion of the anchor from said tubular member, said positioner means being connected with said inner member.

85. An apparatus as set forth in claim 82 further including a handle fixedly connected with said tubular member, said inner member being movable along the passage in said tubular member to effect separation of the trailing end portion of the anchor from said tubular member, said positioner means being connected with said tubular member.

86. An apparatus as set forth in claim 82 wherein the anchor further includes a surface which is engagable by a suture to interconnect the anchor and the suture.

87. An apparatus as set forth in claim 82 wherein a suture is connected with the anchor and is at least partially disposed in the slot in said tubular member.

88. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, said positioner means includes a spring which engages the opening in the anchor.

89. An apparatus as set forth in claim 88 wherein said tubular member includes a side wall having surfaces which at least partially define a slot which extends away from an open end of the passage in the tubular member, said positioner means being connected with a portion of said one of said inner and tubular members opposite from the slot.

90. An apparatus as set forth in claim 89 wherein said spring extends towards the slot, said projection being movable away from the slot under the influence of force transmitted through the anchor to said spring upon relative movement between said tubular member and said inner member.

91. An apparatus as set forth in claim 89 further including indicia disposed on said inner member adjacent to said tubular member, said indicia on said inner member cooperates with said tubular member to indicate the position of said inner member relative to said tubular member.

92. An apparatus as set forth in claim 88 wherein said spring includes a resiliently deflectable projection which applies force against the anchor to press the anchor against a portion of said one of said inner and tubular members.

93. An apparatus as set forth in claim 88 further including a handle fixedly connected with said inner member, said tubular member being movable along said inner member to effect separation of the trailing end portion of the anchor from said tubular member, said spring being connected with said inner member.

94. An apparatus as set forth in claim 88 further including a handle fixedly connected with said tubular member, said inner member being movable along the passage in said tubular member to effect separation of the trailing end portion of the anchor from said tubular member, said spring being connected with said tubular member.

95. An apparatus as set forth in claim 88 wherein the anchor further includes a surface which is engagable by a suture to interconnect the anchor and the suture.

96. An apparatus as set forth in claim 88 wherein a suture is connected with the anchor, said spring has a surface which engages the suture.

97. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, and positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, said positioner means includes a resiliently deflectable projection which applies force against the anchor to press the anchor against a portion of said one of said inner and outer tubular members.

98. An apparatus as set forth in claim 97 wherein said positioner means includes a surface area which is integrally formed as one piece with said one of said inner and tubular members and projects into the opening in the anchor.

99. An apparatus as set forth in claim 97 wherein said tubular member includes a side wall having surfaces which at least partially define a slot which extends away from an open end of the passage in the tubular member, said projection being connected with a portion of said one of said inner and tubular members opposite from the slot.

100. An apparatus as set forth in claim 99 wherein said projection which extends towards the slot, said projection being movable away from the slot under the influence of force transmitted through the anchor to said projection upon relative movement between said tubular member and said inner member.

101. An apparatus as set forth in claim 99 wherein said tubular member is resiliently deflectable from a first condition in which the slot has a first width to a second condition in which the slot has a second width, said second width of the slot being greater than said first width of the slot.

102. An apparatus as set forth in claim 97 further including indicia disposed on said inner member adjacent to said tubular member, said indicia on said inner member cooperates with said tubular member to indicate the position of said inner member relative to said tubular member.

103. An apparatus as set forth in claim 97 wherein said projection engages the opening in the anchor.

104. An apparatus as set forth in claim 97 further including a handle fixedly connected with said inner member, said tubular member being movable along said inner member to effect separation of the trailing end portion of the suture anchor from said tubular member, said positioner means being connected with said inner member.

105. An apparatus as set forth in claim 97 further including a handle fixedly connected with said tubular member, said inner member being movable along the passage in said tubular member to effect separation of the trailing end portion of the anchor from said tubular member, said positioner means being connected with said tubular member.

106. An apparatus as set forth in claim 97 wherein the anchor further includes a surface which is engagable by a suture.

107. An apparatus as set forth in claim 97 wherein a suture is connected with the anchor, said projection has a surface which engages the suture.

108. An apparatus for use in positioning an anchor relative to body tissue, said apparatus comprising a tubular member, an inner member at least partially disposed in a passage in said tubular member, said tubular member and said inner member being movable relative to each other to separate at least a trailing end portion of the anchor from at least one of said tubular and inner members, positioner means connected with said one of said inner and tubular members for engaging an opening in the anchor to position the anchor relative to said one of said inner and tubular members to hold the anchor against movement relative to said one of said inner and tubular members under the influence of force applied to the opening in the anchor by said positioner means, and a handle fixedly connected with said inner member, said tubular member being movable along said inner member to effect separation of the trailing end portion of the anchor from said tubular member, said positioner means being connected with said inner member.

109. A method of positioning an anchor for engagement with body tissue, said method comprising the steps of providing a tubular member having a passage which extends between opposite end portions of the tubular member, moving the anchor to a predetermined position in which a first end portion of the anchor is disposed in the passage in the tubular member and a second end portion of the anchor extends outward from one end portion of the tubular member, and gripping the anchor with the one end portion of the tubular member to retain the anchor in the predetermined position, said step of gripping the anchor includes resiliently deflecting at least a portion of the one end portion of the tubular member under the influence of force transmitted from one of the end portions of the anchor.

110. A method as set forth in claim 109 wherein said step of gripping the anchor includes engaging a recess in the anchor with the one end portion of the tubular member.

111. A method as set forth in claim 109 wherein the one end portion of the tubular member includes a slot which extends from an opening in the one end portion of the tubular member toward an end portion of the tubular member opposite from the one end portion, said step of gripping the anchor includes moving the anchor through the opening in the one end portion of the tubular member and expanding at least a portion of the slot under the influence of force applied against the one end portion of the tubular member by the anchor.

112. A method as set forth in claim 109 wherein said step of moving the anchor to a predetermined position in which a first end portion of the anchor is disposed in the passage and the second end portion of the anchor extends outward from one end portion of the tubular member includes moving the anchor along the passage in the tubular member with the second end portion of the anchor leading, said step of gripping the anchor with the one end portion of the tubular member to retain the anchor in the predetermined position includes engaging a projection which extends inward from an inner side surface of the tubular member with the second end portion of the anchor and moving the projection outward away from a central axis of the tubular member.

113. A method as set forth in claim 109 wherein said step of moving the anchor to the predetermined position in which the first end portion of the anchor is disposed in the passage in the tubular member and the second end portion of the anchor extends outward from the one end portion of the tubular member is performed with a first leg of a suture extending from the first end portion of the anchor and a second leg of the suture extending from the second end portion of the anchor.

114. A method as set forth in claim 109 wherein said step of resiliently deflecting at least a portion of the one end portion of the tubular member includes resiliently expanding at least a portion of the passage in the tubular member from a first cross sectional area to a second cross sectional area which is greater than the first cross sectional area under the influence of force applied against the tubular member by the anchor.

115. A method of positioning an anchor for engagement with body tissue, said method comprising the steps of providing a tubular member having a passage which extends between opposite end portions of the tubular member, moving the anchor to a predetermined position in which a first end portion of the anchor is disposed in the passage in the tubular member and a second end portion of the anchor extends outward from one end portion of the tubular member, and gripping the anchor with the one end portion of the tubular member to retain the anchor in the predetermined position, said step of gripping the anchor with the one end portion of the tubular member to retain the anchor in the predetermined position includes engaging a recess in the anchor with the one end portion of the tubular member.

116. A method as set forth in claim 115 wherein said step of moving the anchor to the predetermined position in which the first end portion of the anchor is disposed in the tubular member and the second end portion of the anchor extends outward from the one end portion of the tubular member is performed with a first leg of a suture extending from the first end portion of the anchor and a second leg of the suture extending from the second end portion of the anchor.

117. A method as set forth in claim 115 wherein said step of engaging a recess in the anchor with the one end portion of the tubular member includes engaging a recess disposed between the first and second end portions of the anchor.

118. A method of positioning an anchor for engagement with body tissue, said method comprising the steps of providing a tubular member having a passage which extends between opposite end portions of the tubular member, moving the anchor to a predetermined position in which a first end portion of the anchor is disposed in the passage in the tubular member and a second end portion of the anchor extends outward from one end portion of the tubular member, and gripping the anchor with the one end portion of the tubular member to retain the anchor in the predetermined position, the one end portion of the tubular member includes a slot which extends from an opening in the one end portion of the tubular member toward an end portion of the tubular member opposite from the one end portion, said step of gripping the anchor with the one end portion of the tubular member to retain the anchor in the predetermined position includes moving the anchor through the opening in the one end portion of the tubular member and expanding at least a portion of the slot under the influence of force applied against the one end portion of the tubular member by the anchor.

119. A method as set forth in claim 118 wherein a suture is connected with the anchor, said step of expanding at least a portion of the slot is performed with at least a portion of the suture disposed in the slot.

120. A method of positioning an anchor for engagement with body tissue, said method comprising the steps of providing a tubular member having a passage which extends between opposite end portions of the tubular member, moving the anchor to a predetermined position in which a first end portion of the anchor is disposed in the passage in the tubular member and a second end portion of the anchor extends outward from one end portion of the tubular member, and gripping the anchor with the one end portion of the tubular member to retain the anchor in the predetermined position, said step of moving the anchor to a predetermined position in which a first end portion of the anchor is disposed in the passage and the second end portion of the anchor extends outward from one end portion of the tubular member includes moving the anchor along the passage in the tubular member with the second end portion of the anchor leading, said step of gripping the anchor with the one end portion of the tubular member to retain the anchor in the predetermined position includes engaging a projection which extends inward from an inner side surface of the tubular member with the second end portion of the anchor and moving the projection outward away from a central axis of the tubular member.

121. A method as set forth in claim 120 wherein said step of moving the anchor to the predetermined position in which the first end portion of the anchor is disposed in the tubular member and the second end portion of the anchor extends outward from the one end portion of the tubular member is performed with a first leg of a suture extending from the first end portion of the anchor and a second leg of the suture extending from the second end portion of the anchor.

122. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, said step of expanding the end portion of the tubular member includes sliding the anchor along a surface on a portion of the passage disposed in the end portion of the tubular member, and, thereafter, holding the anchor against movement relative to the tubular member under the influence of force transmitted from the end portion of the tubular member to the anchor.

123. A method as set forth in claim 122 wherein said step of expanding the end portion of the tubular member includes expanding the end portion of the tubular member from a first condition to a second condition, the portion of the passage in the end portion of the tubular member has a first cross sectional area in a plane extending perpendicular to a longitudinal central axis of the tubular member when the end portion of the tubular member is in the first condition, the portion of the passage in the end portion of the tubular member has a second cross sectional area in a plane extending perpendicular to the longitudinal central axis of the tubular member when the end portion of the tubular member is in the second condition, said second cross sectional area being greater than said first cross sectional area.

124. A method as set forth in claim 122 wherein said step of moving the anchor into a portion of the passage in an end portion of the tubular member includes applying force against a trailing end portion of the anchor and moving the anchor along the passage in the tubular member, said step of expanding the end portion of the tubular member includes transmitting force from the trailing end portion of the anchor through a leading end portion of the anchor to the surface on the portion of the passage disposed in the end portion of the tubular member.

125. A method as set forth in claim 122 wherein said step of holding the anchor against movement relative to the tubular member includes gripping the anchor with at least a portion of the surface on the portion of the passage disposed in the end portion of the tubular member.

126. A method as set forth in claim 122 wherein the surface on the portion of the passage against which the anchor slides along is skewed at an acute angle to a longitudinal central axis of the tubular member with an end portion of the anchor.

127. A method as set forth in claim 122 wherein said step of holding the anchor against movement relative to the tubular member is performed with one end portion of the anchor in the passage in the tubular member and with another end portion of the anchor extending outward from the end portion of the tubular member.

128. A method as set forth in claim 122 wherein said step of expanding the end portion of the tubular member includes resiliently deflecting at least a portion of the end portion of the tubular member as the anchor slides along the surface on a portion of the passage disposed in the end portion of the tubular member.

129. A method as set forth in claim 122 further including the step of interrupting movement of the anchor in the passage in the tubular member when the anchor is in a predetermined position relative to the tubular member, said step of expanding the end portion of the tubular member is performed prior to performance of said step of interrupting movement of the anchor in the passage in the tubular member.

130. A method as set forth in claim 122 wherein the end portion of the tubular member includes a slot which extends from an opening in the second end portion of the tubular member toward an opposite end portion of the tubular member, said step of expanding the end portion of the tubular member includes increasing a distance between opposite sides of at least a portion of the slot.

131. A method as set forth in claim 122 wherein said step of holding the anchor against movement relative to the tubular member includes applying force against one side of the anchor and pressing a side of the anchor opposite from the one side against an inner side surface on the end portion of the tubular member under the influence of force applied against the one side of the anchor.

132. A method as set forth in claim 122 further including the step of connecting a suture with the anchor.

133. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, and, thereafter, holding the anchor against movement relative to the tubular member under the influence of force transmitted from the end portion of the tubular member to the anchor, said step of holding the anchor against movement relative to the tubular member includes gripping the anchor with at least a portion of the passage disposed in the end portion of the tubular member.

134. A method as set forth in claim 133 wherein said step of expanding the end portion of the tubular member includes pressing the anchor against a surface on a portion of the passage disposed in the end portion of the tubular member.

135. A method as set forth in claim 133 wherein said step of expanding the end portion of the tubular member includes expanding the end portion of the tubular member from a first condition to a second condition, the portion of the passage in the end portion of the tubular member has a first cross sectional area in a plane extending perpendicular to a longitudinal central axis of the tubular member when the end portion of the tubular member is in the first condition, the portion of the passage in the end portion of the tubular member has a second cross sectional area in a plane extending perpendicular to the longitudinal central axis of the tubular member when the end portion of the tubular member is in the second condition, said second cross sectional area being greater than said first cross sectional area.

136. A method as set forth in claim 133 wherein said step of moving the anchor into a portion of the passage in an end portion of the tubular member includes applying force against a trailing end portion of the anchor and moving the anchor along the passage in the tubular member, said step of expanding the end portion of the tubular member includes transmitting force from the trailing end portion of the anchor through a leading end portion of the anchor to the end portion of the tubular member.

137. A method as set forth in claim 133 wherein said step of gripping the anchor with at least a portion of a surface of a portion of the passage disposed in the end portion of the tubular member includes gripping a leading end portion of the anchor.

138. A method as set forth in claim 133 wherein said step of expanding the end portion of the tubular member includes applying force against a surface which is skewed at an acute angle to a longitudinal central axis of the tubular member with an end portion of the anchor.

139. A method as set forth in claim 133 wherein said step of holding the anchor against movement relative to the tubular member is performed with one end portion of the anchor in the passage in the tubular member and with another end portion of the anchor extending outward from the end portion of the tubular member.

140. A method as set forth in claim 133 wherein said step of expanding the end portion of the tubular member includes resiliently deflecting at least a portion of the end portion of the tubular member in which the portion of the passage with which the anchor is gripped is disposed.

141. A method as set forth in claim 133 further including the step of interrupting movement of the anchor in the passage in the tubular member when the anchor is in a predetermined position relative to the tubular member, said step of expanding the end portion of the tubular member is performed prior to performance of said step of interrupting movement of the anchor in the passage in the tubular member.

142. A method as set forth in claim 133 wherein the end portion of the tubular member includes a slot which extends from an opening in the second end portion of the tubular member toward an opposite end portion of the tubular member, said step of expanding the end portion of the tubular member includes increasing a distance between opposite sides of at least a portion of the slot.

143. A method as set forth in claim 133 wherein said step of holding the anchor against movement relative to the tubular member includes applying force against one side of the anchor and pressing a side of the anchor opposite from the one side against an inner side surface on the end portion of the tubular member under the influence of force applied against the one side of the anchor.

144. A method as set forth in claim 133 further including the step of connecting a suture with the anchor.

145. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, said step of expanding the end portion of the tubular member includes applying force against a surface which is skewed at an acute angle to a longitudinal central axis of the tubular member with an end portion of the anchor, and, thereafter, holding the anchor against movement relative to the tubular member under the influence of force transmitted from the end portion of the tubular member to the anchor.

146. A method as set forth in claim 145 wherein said step of expanding the end portion of the tubular member includes sliding the anchor along the surface which is skewed at an acute angle to the longitudinal central axis of the tubular member.

147. A method as set forth in claim 145 wherein said step of expanding the end portion of the tubular member includes expanding the end portion of the tubular member from a first condition to a second condition, the portion of the passage in the end portion of the tubular member has a first cross sectional area in a plane extending perpendicular to the longitudinal central axis of the tubular member when the end portion of the tubular member is in the first condition, the portion of the passage in the end portion of the tubular member has a second cross sectional area in a plane extending perpendicular to the longitudinal central axis of the tubular member when the end portion of the tubular member is in the second condition, said second cross sectional area being greater than said first cross sectional area.

148. A method as set forth in claim 145 wherein said step of moving the anchor into a portion of the passage in an end portion of the tubular member includes applying force against a trailing end portion of the anchor and moving the anchor along the passage in the tubular member, said step of expanding the end portion of the tubular member includes transmitting force from the trailing end portion of the anchor through a leading end portion of the anchor to the surface which is skewed at an acute angle to the longitudinal central axis of the tubular member.

149. A method as set forth in claim 145 wherein said step of holding the anchor against movement relative to the tubular member includes gripping the anchor with at least a portion of a surface of the surface which is skewed at an acute angle to the longitudinal central axis of the tubular member.

150. A method as set forth in claim 145 wherein said step of expanding the end portion of the tubular member includes sliding a leading end portion of the anchor along the surface which is skewed at an acute angle to a longitudinal central axis of the tubular member.

151. A method as set forth in claim 145 wherein said step of holding the anchor against movement relative to the tubular member is performed with one end portion of the anchor in the passage in the tubular member and with another end portion of the anchor extending outward from the end portion of the tubular member.

152. A method as set forth in claim 145 wherein said step of expanding the end portion of the tubular member includes resiliently deflecting at least a portion of the end portion of the tubular member on which the surface which is skewed at an acute angle to the longitudinal central axis of the tubular member is disposed.

153. A method as set forth in claim 145 further including the step of interrupting movement of the anchor in the passage in the tubular member when the anchor is in a predetermined position relative to the tubular member, said step of expanding the end portion of the tubular member is performed prior to performance of said step of interrupting movement of the anchor in the passage in the tubular member.

154. A method as set forth in claim 145 wherein the end portion of the tubular member includes a slot which extends from an opening in the second end portion of the tubular member toward an opposite end portion of the tubular member, said step of expanding the end portion of the tubular member includes increasing a distance between opposite sides of at least a portion of the slot.

155. A method as set forth in claim 145 wherein said step of holding the anchor against movement relative to the tubular member includes applying force against one side of the anchor with the surface which is skewed at an acute angle to a longitudinal central axis of the tubular member and pressing a side of the anchor opposite from the one side against an inner side surface on the end portion of the tubular member under the influence of force applied against the one side of the anchor.

156. A method as set forth in claim 145 further including the step of connecting a suture with the anchor.

157. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, interrupting movement of the anchor in the passage in the tubular member when the anchor is in a predetermined position relative to the tubular member, said step of expanding the end portion of the tubular member is performed prior to performance of said step of interrupting movement of the anchor in the passage in the tubular member, and, thereafter, holding the anchor against movement relative to the tubular member under the influence of force transmitted from the end portion of the tubular member to the anchor.

158. A method as set forth in claim 157 wherein said step of expanding the end portion of the tubular member includes pressing a leading end portion of the anchor against a surface on a portion of the passage disposed in the end portion of the tubular member prior to moving the anchor to the predetermined position relative to the tubular member.

159. A method as set forth in claim 157 wherein said step of expanding the end portion of the tubular member includes expanding the end portion of the tubular member from a first condition to a second condition, the portion of the passage in the end portion of the tubular member has a first cross sectional area in a plane extending perpendicular to a longitudinal central axis of the tubular member when the end portion of the tubular member is in the first condition, the portion of the passage in the end portion of the tubular member has a second cross sectional area in a plane extending perpendicular to the longitudinal central axis of the tubular member when the end portion of the tubular member is in the second condition, said second cross sectional area being greater than said first cross sectional area.

160. A method as set forth in claim 157 wherein said step of moving the anchor into a portion of the passage in an end portion of the tubular member includes applying force against a trailing end portion of the anchor and moving the anchor along the passage in the tubular member, said step of expanding the end portion of the tubular member includes transmitting force from the trailing end portion of the anchor through a leading end portion of the anchor to the end portion of the tubular member.

161. A method as set forth in claim 157 wherein said step of holding the anchor against movement relative to the tubular member includes gripping the anchor with the tubular member while the anchor is in the predetermined position relative to the tubular member.

162. A method as set forth in claim 157 wherein said step of expanding the end portion of the tubular member includes applying force against the tubular member with the anchor as the anchor moves to the predetermined position relative to the tubular member.

163. A method as set forth in claim 157 wherein said step of holding the anchor against movement relative to the tubular member is performed with the anchor in the predetermined position and with one end portion of the anchor in the passage in the tubular member and with another end portion of the anchor extending outward from the end portion of the tubular member.

164. A method as set forth in claim 157 wherein said step of expanding the end portion of the tubular member includes resiliently deflecting at least a portion of the end portion of the tubular member.

165. A method as set forth in claim 157 wherein the end portion of the tubular member includes a slot which extends from an opening in the second end portion of the tubular member toward an opposite end portion of the tubular member, said step of expanding the end portion of the tubular member includes increasing a distance between opposite sides of at least a portion of the slot.

166. A method as set forth in claim 157 wherein said step of holding the anchor against movement relative to the tubular member includes applying force against one side of the anchor and pressing a side of the anchor opposite from the one side against an inner side surface on the end portion of the tubular member under the influence of force applied against the one side of the anchor.

167. A method as set forth in claim 157 further including the step of connecting a suture with the anchor.

168. A method of positioning an anchor for engagement with body tissue, said method comprising the steps of providing a tubular member having a passage, moving the anchor into a portion of the passage in an end portion of the tubular member, expanding the end portion of the tubular member under the influence of force transmitted from the anchor to the end portion of the tubular member as the anchor moves into the portion of the passage disposed in the end portion of the tubular member, and, thereafter, holding the anchor against movement relative to the tubular member under the influence of force transmitted from the end portion of the tubular member to the anchor, step of holding the anchor against movement relative to the tubular member includes applying force against one side of the anchor and pressing a side of the anchor opposite from the one side against an inner side surface on the end portion of the tubular member under the influence of force applied against the one side of the anchor.

169. A method as set forth in claim 168 further including the step of connecting a suture with the anchor.

\* \* \* \* \*